US009493463B2

(12) United States Patent
Tung et al.

(10) Patent No.: US 9,493,463 B2
(45) Date of Patent: *Nov. 15, 2016

(54) SUBSTITUTED XANTHINE DERIVATIVES

(71) Applicant: Concert Pharmaceuticals, Inc., Lexington, MA (US)

(72) Inventors: Roger D. Tung, Lexington, MA (US); Julie F. Liu, Lexington, MA (US); Scott L. Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/713,423

(22) Filed: May 15, 2015

(65) Prior Publication Data

US 2015/0322068 A1    Nov. 12, 2015

Related U.S. Application Data

(63) Continuation of application No. 13/949,888, filed on Jul. 24, 2013, now Pat. No. 9,035,050, which is a continuation of application No. 12/380,579, filed on Feb. 27, 2009, now abandoned.

(60) Provisional application No. 61/198,715, filed on Nov. 7, 2008, provisional application No. 61/134,568, filed on Jul. 11, 2008, provisional application No. 61/067,736, filed on Feb. 29, 2008.

(51) Int. Cl.
*C07D 473/04* (2006.01)
*C07D 473/10* (2006.01)

(52) U.S. Cl.
CPC ........... *C07D 473/10* (2013.01); *C07D 473/04* (2013.01); *C07B 2200/05* (2013.01); *C07B 2200/07* (2013.01)

(58) Field of Classification Search
CPC .............. C07D 473/10; C07D 473/04; C07B 2200/07; C07B 2200/05
See application file for complete search history.

(56) References Cited

U.S. PATENT DOCUMENTS

| 5,112,827 | A | 5/1992 | Saunders et al. |
|---|---|---|---|
| 5,648,357 | A | 7/1997 | Bianco et al. |
| 5,780,476 | A * | 7/1998 | Underiner ............ A61K 31/522 514/263.36 |
| 5,846,514 | A | 12/1998 | Foster et al. |
| 6,020,337 | A | 2/2000 | Leigh et al. |
| 6,221,335 | B1 | 4/2001 | Foster |
| 6,316,458 | B1 | 11/2001 | Nadler et al. |
| 6,420,374 | B1 | 7/2002 | Bianco et al. |
| 6,440,710 | B1 | 8/2002 | Keinan et al. |
| 6,603,008 | B1 | 8/2003 | Ando et al. |
| 7,517,990 | B2 | 4/2009 | Ito et al. |
| 7,598,273 | B2 | 10/2009 | Gant et al. |
| 8,263,601 | B2 | 9/2012 | Tung et al. |
| 8,952,016 | B2 | 2/2015 | Tung et al. |
| 8,987,442 | B2 | 3/2015 | Tung et al. |
| 9,035,050 | B2 | 5/2015 | Tung et al. |
| 2005/0107420 | A1 | 5/2005 | Armstrong et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |
| 2008/0249089 | A1 | 10/2008 | Himmelsbach et al. |
| 2009/0239886 | A1 | 9/2009 | Tung et al. |
| 2011/0053961 | A1 | 3/2011 | Tung et al. |
| 2011/0059995 | A1 | 3/2011 | Tung et al. |
| 2011/0077255 | A1 | 3/2011 | Tung et al. |
| 2012/0202830 | A1 | 8/2012 | Tung et al. |

FOREIGN PATENT DOCUMENTS

| WO | 87/00523 A2 | 1/1987 |
|---|---|---|
| WO | 94/22449 A1 | 10/1994 |
| WO | 95/26325 A2 | 10/1995 |
| WO | 9605854 A2 | 2/1996 |
| WO | 2007041630 A1 | 4/2007 |
| WO | 2007/118651 A1 | 10/2007 |
| WO | 2009/108375 A1 | 9/2009 |
| WO | 2009/108383 A2 | 9/2009 |
| WO | 2011/028835 A1 | 3/2011 |
| WO | 2011/028922 A1 | 3/2011 |

OTHER PUBLICATIONS

Badri, S.,"A review of the potential benefits of pentoxifylline in diabetic and non-diabetic proteinuria." Journal of Pharmacy & Pharmaceutical Sciences 14.1 (2011): 128-137.*
Kania, D. S., "Potential new treatments for diabetic kidney disease." Medical Clinics of North America 97.1 (2013): 115-134.*
Nicklasson, M.,"Stereoselective metabolism of pentoxifylline in vitro and in vivo in humans." Chirality 14.8 (2002): 643-652.*
Smith, R.V.,"Pharmacokinetics of orally administered pentoxifylline in humans." Journal of pharmaceutical sciences 75.1 (1986): 47-52.*
Nicklasson et al., "Stereoselective Metabolism of Pentoxifylline in Vitro and in Vivo in Humans," Chirality 14:643-652 (2002).
Raoul, et al., A Novel Drug Interaction Between the Quinolone Antibiotic Ciprofloxacin and a Chiral Metabolite of Pentoxifylline, Biochemical Pharmacology; 74:639-646 (2007).
Park, et al. "Metabolism of Fluorine-containing Drugs," Annu. Rev. Pharmacol. Toxicol. (41) 443-70 (2001).
Synfine Catalogue "Pentoxifylline-d3" listed in online catalogue dated Oct. 21, 2007; accessed at http://web.archive.org/web/20071021050605/http://synfine.com/products_details.cfm?autoid=604.

(Continued)

*Primary Examiner* — Samantha Shterengarts
*Assistant Examiner* — Matt Mauro
(74) *Attorney, Agent, or Firm* — McCarter & English, LLP; Steven G. Davis; Emily Dertz

(57) ABSTRACT

This invention relates to novel compounds that are substituted xanthine derivatives and pharmaceutically acceptable salts thereof. For example, this invention relates to novel substituted xanthine derivatives that are derivatives of pentoxifylline. This invention also provides compositions comprising one or more compounds of this invention and a carrier and the use of the disclosed compounds and compositions in methods of treating diseases and conditions for which pentoxifylline and related compounds are beneficial.

21 Claims, 6 Drawing Sheets

(56) References Cited

OTHER PUBLICATIONS

Synfine Catalogue "1-(3-carboxypropyl) 3,7-dimethyl Xanthine-d6" listed in online catalogue dated Oct. 21, 2007; accessed at http://web.archive.org/web/20071021050610/http://synfine.com/products_details.cfm?autoid=605.
Synfine Catalogue "Hydroxy Pentoxifylline-d3" listed in online catalogue dated Oct. 21, 2007; accessed at http://web.archive.org/web/20071021050615/http://synfine.com/products_details.cfm?autoid =606.
International Search Report issued in PCT Application No. PCT/US2009/001294 on Jul. 8, 2009.
International Search Report issued in PCT Application No. PCT/US2009/001305 on Aug. 18, 2009.
Davila-Esqueda, M.E., et al., Pentofxifyline Diminishes the Oxidative Damage to Renal Tissue Induced by Streptozotocin in the Rat, Experimental Diab. Res., 5:245-251, 2004.
Friese, Ryan S., et al, Matrix Metalloproteinases: Discrete Elevations in Essential Hypertension and Hypertensive end-Stage Renal Disease, Clin. Exp. Hypertens, 31(7):521-533: Oct. 2009.
Cirillo, Pietro, et al., Systemic Inflammation, Metabolic Syndrome and Progressive Renal Disease, Nephrol Dial Transplant, 24:1384-1387, Feb. 10, 2009.
Tesch, Greg H., et al., Methods in Renal Research, Rodent Models of Streptozoticin-Induced Diabetic Nephropathy, Nephrology, 12:261-266, 2007.
Hewitson, Tim D., et al., Small Animal Models of Kidney Disease: A Review, Methods in Molecular Biology, 466:41-57, 2009.
Latta, Paul P., Pat. App. Lexis 4112, Board of Patent Appeals and Interference, 5pp, Oct. 10, 2007.
Saishin Souyaku Kagaku (The Practice of Medicinal Chemistry), Vl 1, p. 379, 1998.
Diabetic Nephropathy Treatment Overview, http://diabetes.webmd.com/tc/diabetic-nephropathy-treatment-overview, lownloaded from the Internet Jan. 16, 2013.
Written Opinion of the International Searching Authority issued in PCT/US2009/001294 dated Jul. 8, 2009.
Written Opinion of the International Searching Authority issued in PCT/US2009/001305 dated Aug. 18, 2009.
Buteau, Kristen C., Deuterated Drugs: Unexpectedly Nonobvious?, Journal of High Technology Law, X(1):22-74, 2009.
Cell Therapeutics Suffers on Lisofylline Trial Data, Cuts Development, http://www.thepharmaletter.com/file/20592/cell-therepeutics-suffers-on-lisofylline-trial-data-cuts-development.html, downloaded from the Internet Aug. 9, 2011.
Forbes et al., Oxidative Stress as a Major Culprit in Kidney Disease in Diabetes, Diabetes, vol. 57, pp. 1446-1454 (2008).
Sweeney, The Open Critical Care Medicine Journal, 2010, 3, 7-19.
Bolick, D., Lisofylline, a novel antiinflammatory compound, protects mesangial cells from hyperglycemia-and angiotensin II-mediated extracellular matrix deposition, Endocrinology 144. 12(2003):5227-5231.
Blake et al., "Studies with Deuterated Drugs," J Pharm Sci, 1975, 64:367-391.
Fukuto, et al., Determination of the Mechanism of Demethylenation of (Methylenedioxy)phenyl Compounds by Cytochrome P450 Using Deuterium Isotope Effects, J Med Chem, 1991, 34:2871-2876.
Badri, S., A review of the potential benefits of pentoxifylline in a diabetic and non-diabetic proteinuria, Journal of Pharmacy & Pharmaceutical Sciences, 14.1:128-138, 2011.
Kania, D.S., Potential new treatments for diabetic kidney disease, Medical Clinics of North America, 97.1:115-134, 2013.
Smith, R.V., Pharmacokinetics of orally administered pentoxifylline in humans, Journal of Pharmaceutical Sciences, 751:47-52, 1986.
Anderson, R.J., "Recent Advances and developments in the treatment of acute renal failure," Expert Opin. Ther. Patents,vol. 12, No. 5, pp. 645-655, 2002.
Baillie, Thomas A., "The Use of Stable Isotopes in Pharmacological Research", Pharmacological Reviews, vol. 33, No. 2, pp. 81-132, 1981.

Browne, Thomas R., "Stable Isotope Techniques in Early Drug Development: An Economic Evaluation", J. Clin. Pharmacol, vol. 38, pp. 213-220, 1998.
Bursten, et al., "Lisofylline Causes Rapid and Prolonged Suppression of Serum Levels of Free Fatty Acids", The Journal of Pharmacology and Experimental Therapeutics, vol. 284, No. 1, pp. 337-345, 1997.
Cherrah, et al., "Study of Deuterium Isotope Effects on Protein Binding by Gas Chromatography/Mass Spectrometry. Caffeine and Deuterated Isotopomers", Biomedical and Environmental Mass Spectrometry, vol. 14, pp. 653-657, 1987.
Davis, et al., "Microbial models of mammalian metabolism: stereospecificaity of ketone reduction with pentoxifylline", Xenobiotica, vol. 15, No. 12, pp. 1001-1010, 1985.
Dyck, et al., "Effects of Deuterium Substitution on the Catabolism of ?-Phenylethylamine: An in Vivo Study", Journal of Neurochemistry, vol. 46, No. 2, pp. 399-404, 1986.
Ellermann, et al., Effect of pentoxifylline on the ischemic rat kidney monitored by 31P NMR spectroscopy in vivo, Biomed. Biochim. Acta, vol. 47, No. 6, pp. 515-521, 1988.
Fisher, et al., "The complexities inherent in attempts to decrease drug clearance by blocking sites of CYP-mediated metabolism," Current Opinion in Drug Discovery & Development, vol. 9, No. 1, pp. 101-109, 2006.
Foster, Allan B., "Deuterium isotope effects in studies of drug metabolism", TIPS, pp. 524-527, 1984.
Foster, Allan B., "Deuterium Isotope Effects in the Metabolism of Drugs and Xenobiotics: Implications for Drug Design", Advances in Drug Research, vol. 14, pp. 2-40, 1985.
Gouyette, et al., "Synthesis of Deuterium-labelled Elliptinium and its Use in Metabolic Studies", Biomedical and Environmental Mass Spectrometry, vol. 15, pp. 243-247, 1988.
Haskins, N.J., "The Application of Stable Isotopes in Biomedical Research", Biomedical Mass Spectrometry, vol. 9, No. 7, pp. 269-277, 1982.
Honma, et al., "Liberation of Deuterium from the Piperidine Ring during Hydroxylation", Drug Metabolism and Disposition, vol. 15, No. 4, pp. 551-559, 1987.
International Preliminary Report on Patentabilty issued in PCT Application No. PCT/US2009/001294 on Aug. 31, 2010.
International Preliminary Report on Patentabilty issued in PCT Application No. PCT/US2009/001305 on Aug. 31, 2010.
International Search Report issued in PCT Application No. PCT/US2010/047574 on Oct. 14, 2010.
International Search Report issued in PCT Application No. PCT/US2010/047708 on Oct. 22, 2010.
Kushner, et al., "Pharmacological uses and perspectives of heavy water and deuterated compounds", Can. J. Physiol. Pharmacol., vol. 77, pp. 79-88, 1999.
Lee, et al., "Cytochrome P450 Isozymes Involved in Lisofylline Metabolism to Pentoxifylline in Human Liver Microsomes", Drug Metabolism and Disposition, vol. 25, No. 12, pp. 1354-1358, 1997.
Lillibridge, et al., "Metabolism of Lisofylline and Pentoxifylline in Human Liver Microsomes and Cytosol", Drug Metabolism and Disposition, vol. 24, No. 11, pp. 1174-1179, 1996.
Lin et al. "The Renoprotective Potential of Pentoxifylline in Chronic Kidney Disease," J. Chen. Med. Assoc. vol. 68, No. 3, pp. 99-105, 2005.
Paap, et al., "Multiple-Dose Pharmacokinetics of Pentoxifylline and its Metabolites During Renal Insufficiency", The Annals of Pharmacotherapy, vol. 30, pp. 724-729, 1996.
Pieniaszek, et al., "Moricizine Bioavailablity via Simultaneous, Dual, Stable Isotope Administration: Bioequivalence Implications", The Journal of Clinical Pharmacology, vol. 39, pp. 817-825, 1999.
Tonn, et al., Simultaneous Analysis of Diphenhydramine and a Stable Isotope Analog (2H10)Diphenhydramine Using capillary Gas Chromatography with Mass Selective Detection in Biological Fluids from chronically Instrumented Pregnant Ewes, Biological Mass Spectrometry, vol. 22. 633-642, 1993.
TRENTAL FDA label, Aventis Pharmaceuticals Inc., Apr. 2004.
Ward et al. "Pentoxifylline. A review of its pharmacodynamic and pharmacokinetic properties and its therapeutic effects", Drugs, vol. 34, pp. 50-97, 1987.

(56) References Cited

OTHER PUBLICATIONS

Wolen, Robert L., "The Application of Stable Isotopes to Studies of Drug Bioabailablity and Bioequivalence", The Journal of Clinical Pharmacology, vol. 26, pp. 419-424, 1986.
Wyska, et al., "Pharmacokinetic modeling of pentoxifylline and lisofylline after oral and intravenous administration in mice", Journal of Pharmacy and Pharmacology, vol. 59, pp. 495-501, 2007.
Magnusson, et al., Effects of Pentoxifylline and its Metabolites on Platelet Aggregation in Whole Blood from Healthy Humans, European Journal of Pharmacology 581:290-295, 2008.
Written Opinion of the International Searching Authority issued in PCT/US2010/047574 dated Oct. 9, 2010.
Written Opinion of the International Searching Authority issued in PCT/US2010/047708 dated Oct. 9, 2010.
International Preliminary Report on Patentabilty issued in PCT Application No. PCT/US2010/047574 on Mar. 6, 2012.
International Preliminary Report on Patentabilty issued in PCT Application No. PCT/US2010/047708 on Mar. 6, 2012.
Gao, C, MG132 ameliorates kidney lesions by inhibiting the degradation of Smad7 in streptozotocin-induced diabetic nephropathy, Journal of diabetes research 2014 :1-8, 2014: http://dx.doi.org/10.1155/2014/207140; accessed online Nov. 21, 2015.

* cited by examiner

SUBSTITUTED XANTHINE DERIVATIVES

RELATED APPLICATIONS

This application claims the benefit of U.S. Provisional Application No. 61/067,736, filed on Feb. 29, 2008, U.S. Provisional Application No. 61/134,568, filed on Jul. 11, 2008 and U.S. Provisional Application No. 61/198,715, filed on Nov. 7, 2008. The entire teachings of the above applications are incorporated herein by reference.

BACKGROUND OF THE INVENTION

Pentoxifylline, 1-(5-oxohexyl)-3,7-dimethylxanthine, is sold under the name Trental® in the U.S. and Canada. It is currently approved for the treatment of patients with intermittent claudication on the basis of chronic occlusive arterial disease of the limbs. It is also in clinical trials for glomerulonephritis, nephrotic syndrome, nonalcoholic steatohepatitis, Leishmaniasis, cirrhosis, liver failure, Duchenne's muscular dystrophy, HIV infection, late radiation induced injuries, radiation induced lymphedema, alcoholic hepatitis, radiation fibrosis, necrotizing enterocolitis in premature neonates, chronic kidney disease, pulmonary sarcoidosis, recurrent aphthous stomatitis, chronic breast pain in breast cancer patients, brain and central nervous system tumors, and malnutrition-inflammation-cachexia syndrome. Pentoxifylline has also recently garnered attention as a potential treatment for diabetes and disorders associated with diabetes. See Ferrari, E et al., Pharmatherapeutica, 1987, 5(1): 26-39; Raptis, S et al., Acta Diabetol Lat, 1987, 24(3):181-92; and Rahbar, R et al., Clin Chim Acta, 2000, 301(1-2): 65-77.

Pentoxifylline is known to have activity as an inhibitor of phosphodiesterase (PDE; see Meskini, N et al., Biochem. Pharm. 1994, 47(5): 781-788) as well as activity against other biological targets, but its exact mode of action leading to clinical effects is unknown. Pentoxifylline has been shown to improve blood flow properties through hemorheologic effects which lower blood viscosity and improve erythrocyte flexibility. Pentoxifylline also increases leukocyte deformability and inhibits neutrophil adhesion and activation. (See FDA label for pentoxifylline at http://www.fda.gov/cder/foi/nda/99/74-962_Pentoxifylline_prntl-bl.pdf). In addition to improving hemorheologic properties, pentoxifylline is also believed to have anti-inflammatory and anti-fibrotic properties.

The clinical pharmacology of pentoxifylline has been attributed to the parent drug as well as its metabolites, though the sequence of events leading to clinical improvement is still to be defined. Pentoxifylline undergoes rapid first pass metabolism. Peak plasma levels of pentoxifylline and its metabolites are reached within one hour. Structures of pentoxifylline and its various reported metabolites are shown below.

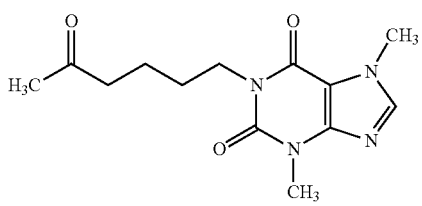

Pentoxifylline

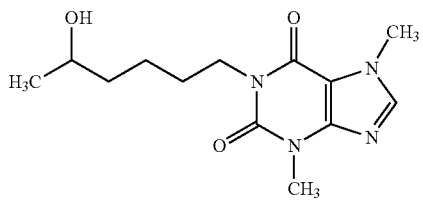
M-1

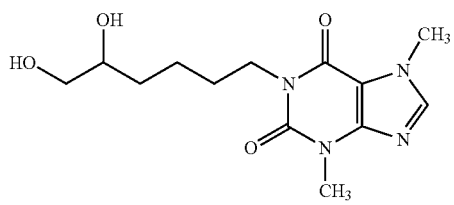
M-2

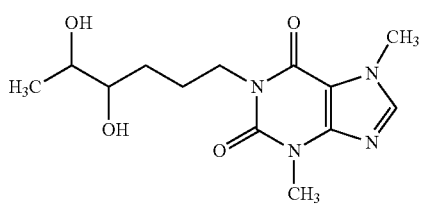
M-3

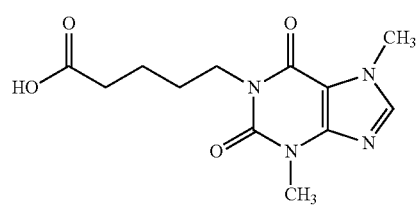
M-4

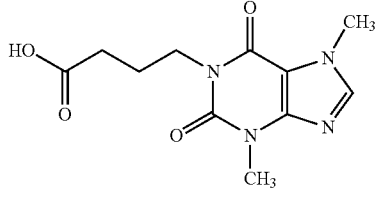
M-5

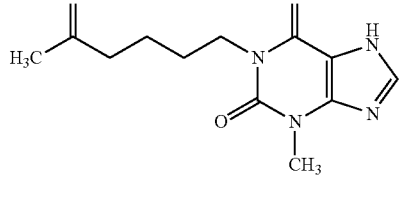
M-6

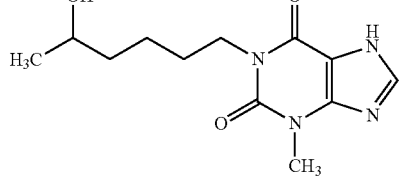
M-7

The major metabolites generated are M-1 and M-5. Plasma levels of these metabolites are five and eight times greater, respectively, than the parent drug. (See FDA label for pentoxifylline at http://www.fda.gov/cder/foi/nda/99/74-962_Pentoxifylline_prntlbl.pdf). The M-1 metabolite has a chiral center and both the (R)- and (S)-enantiomers are formed. During the metabolism of pentoxifylline, an interconversion takes place between the M-1 enantiomers and pentoxifylline. The (S)-enantiomer is the predominant M-1 species (ratio of S:R is reported to be approximately 90:10 or greater) and interconverts more rapidly than the (R)-enantiomer. The minor (R)-M1 metabolite (known as lisofylline) is reported to have novel anti-inflammatory properties.

While active M1 metabolite appears to play a central role in the clinical activity of pentoxifylline, other metabolites may contribute to drug toxicity. Notably, the risk of toxic reactions to pentoxifylline may be greater in patients suffering from renal impairment (http://products.sanofi-aventis.us/trental/trental.pdf). According to product labels, patients with renal impairment who take the drug require the monitoring of renal function. Moreover, at least one product label warns that pentoxifylline should not be administered to patients with severe renal or hepatic impairment. See Trental® Product Monograph, Canada, Dec. 16, 2008. In patients with renal impairment, it was reported that the plasma levels of pentoxifylline and M-1 exhibited a downward trend, while the levels of the M-4 and especially M-5 metabolite increased greatly depending on the degree of impairment. See Paap, Ann. Pharmacother., 1996, 30: 724. Taken together these observations suggest that accumulation of the M5 metabolite may be responsible for the reduced tolerability in patients with renal dysfunction.

Other compounds that are structurally related to pentoxifylline have been reported to be biologically active. Examples of such compounds include albifylline, torbafylline, A-802715, and propentofylline shown below.

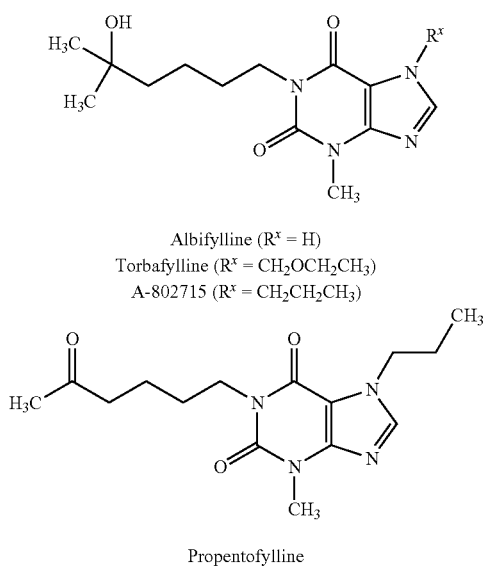

Albifylline ($R^x$ = H)
Torbafylline ($R^x$ = $CH_2OCH_2CH_3$)
A-802715 ($R^x$ = $CH_2CH_2CH_3$)

Propentofylline

Despite the beneficial activities of pentoxifylline, there is a continuing need for new compounds to treat the aforementioned diseases and conditions in a greater patient population while mitigating the risk of toxic reactions and other adverse effects.

SUMMARY OF THE INVENTION

This invention relates to novel compounds that are substituted xanthine derivatives and pharmaceutically acceptable salts thereof. For example, this invention relates to novel substituted xanthine derivatives that are structurally related to pentoxifylline. This invention also provides compositions comprising one or more compounds of this invention and a carrier and the use of the disclosed compounds and compositions in methods of treating diseases and conditions for which pentoxifylline and related compounds are beneficial.

DETAILED DESCRIPTION OF THE INVENTION

Figure 1A:
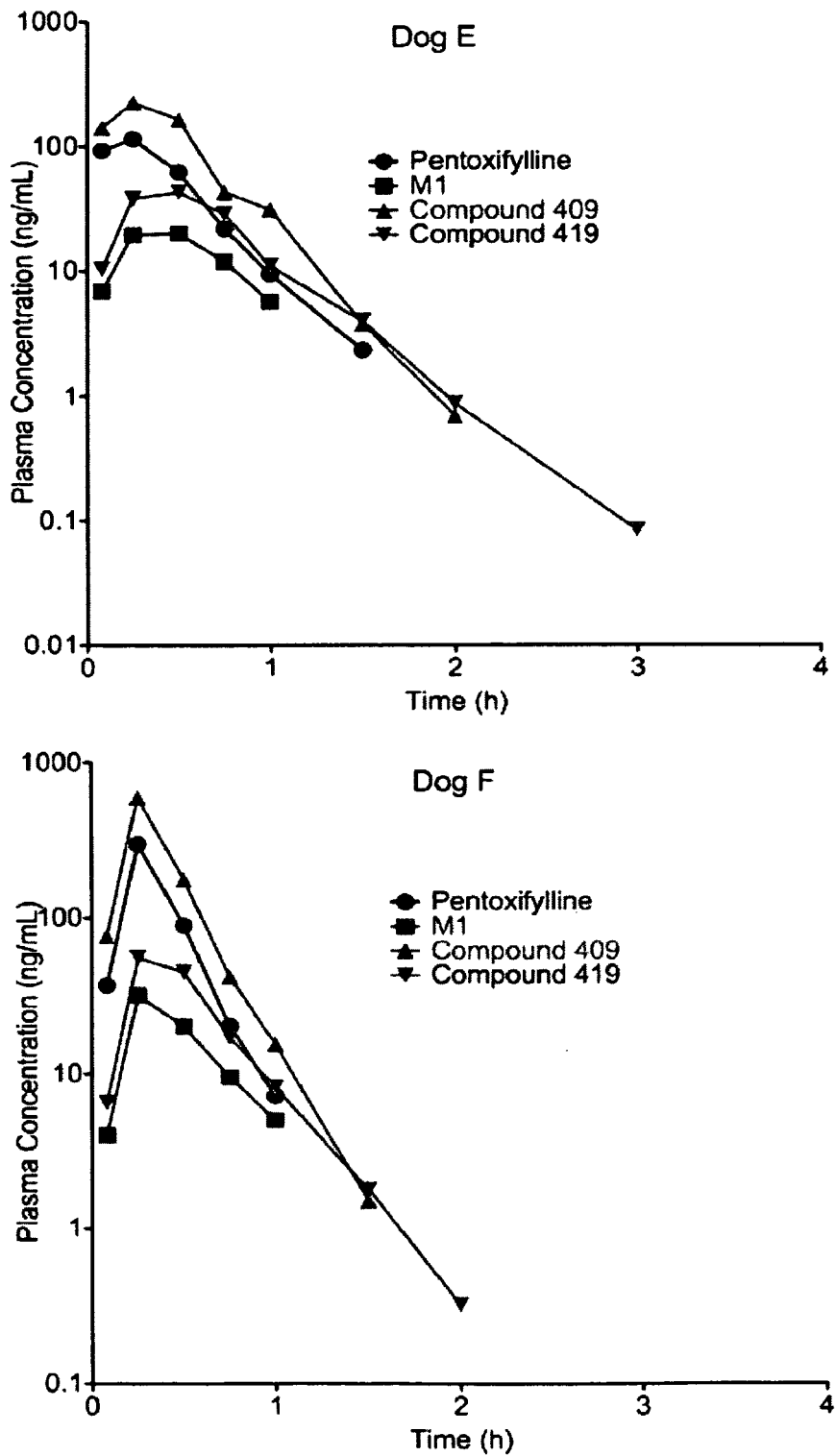
FIGS. 1A and 1B depict the serum levels of a compound of this invention, pentoxifylline and certain of their respective metabolites in four individual dogs following oral administration of a combination of pentoxifylline and that compound of this invention.

The terms "ameliorate" and "treat" are used interchangeably. Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of pentoxifylline will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku, 1994, 66: 15; Gannes L Z et al., Comp Biochem Physiol Mol Integr Physiol, 1998, 119: 725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3340 (50.1% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above, the relative amount of such isotopologues in toto will be less than 49.9% of the compound.

The invention also provides salts of the compounds of the invention. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen sulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The invention also includes solvates and hydrates of the compound of the invention. As used herein, the term "hydrate" means a compound which further includes a stoichiometric or non-stoichiometric amount of water bound by non-covalent intermolecular forces. As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

It is understood that the carbon atom that bears substituents $Y^1$ and $Y^2$ in Formulae A, A1, I and B can be chiral in some instances (when $Y^1$, $Y^2$ and $R^3$ are different from one another) and in other instances it can be achiral (when at least two of $Y^1$, $Y^2$ and $R^3$ are the same). This carbon atom (i.e., the carbon atom bearing $Y^1$ and $Y^2$) is indicated by an "*" in Formulae A, A1, I and B. As such, chiral compounds of this invention can exist as either individual enantiomers, or as racemic or scalemic mixtures of enantiomers. Accordingly, a compound of the present invention will include racemic and scalemic enantiomeric mixtures, as well as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", "", and "t-" each refer to tertiary. "US" refers to the United States of America.

As used herein the term "alkylene" means a straight or branched chain divalent hydrocarbon radical, preferably having from one to six carbon atoms ($C_{1-6}$alkylene). In some embodiments, the alkylene group has from one to four carbon atoms ($C_{1-4}$alkylene). Examples of "alkylene" as used herein include, but are not limited to, methylene (—$CH_2$—), ethylene (—$CH_2CH_2$—), propylene (—$CH_2CH_2CH_2$—), and branched versions thereof such as (—CH($CH_3$)—), —$CH_2$CH($CH_3$)— and the like.

"Halo" means chloro, bromo, fluoro, or iodo.

"Alkyl" means an aliphatic hydrocarbon group which may be straight or branched having 1 to 15 carbon atoms in the chain. Preferred alkyl groups have 1 to 12 carbon atoms in the chain, and more preferably 1 to 6 carbon atoms. Branched means that one or more lower alkyl groups such as methyl, ethyl or propyl are attached to a linear alkyl chain. "Lower alkyl" means about 1 to about 4 carbon atoms in the chain which may be straight or branched. Exemplary alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl; preferred are methyl, difluoromethyl and i-propyl. Alkyl groups may be optionally substituted with one or more groups selected from halo, cyano, hydroxyl, carboxy, alkoxy, alkoxycarbonyl, oxo, amino, alkylamino, dialkylamino, cycloheteroalkyl, alkylcycloheteroalkyl, aryl, alkylaryl, heteroaryl, and alkylheteroaryl. Typically any alkyl or alkoxy moiety of the alkyl substituent group has 1 to 6 carbon atoms.

"Aryl" means an aromatic carbocyclic radical containing 6 to 10 carbon atoms. Exemplary aryl groups include phenyl or naphthyl. Aryl groups may be optionally substituted with one or more groups which may be the same or different, and which are selected from alkyl, aryl, aralkyl, alkoxy, aryloxy, aralkyloxy, halo, and nitro. Typically any alkyl or alkoxy moiety of the aryl substituent group has 1 to 6 carbon atoms.

"Heteroaryl" means a 5- to a 10-membered aromatic monocyclic or multicyclic hydrocarbon ring system in which one or more of the carbon atoms in the ring system is or are element(s) other than carbon, for example nitrogen, oxygen or sulfur. Heteroaryl groups may be optionally substituted with one or more groups which may be the same or different, and which are selected from alkyl, aryl, aralkyl, alkoxy, aryloxy, aralkyloxy, halo, and nitro. Exemplary heteroaryl groups include pyrazinyl, furanyl, thienyl, pyridyl, pyrimidinyl, isoxazolyl, isothiazolyl, pyridazinyl, 1,2,4-triazinyl, quinolinyl, and isoquinolinyl.

"Aralkyl" means an aryl-alkyl group in which the aryl and alkyl components are as previously described. Preferred aralkyls contain a lower alkyl moiety. Exemplary aralkyl groups include benzyl and 2-phenethyl.

"Heteroaralkyl" means a heteroaryl-alkyl group in which the heteroaryl and alkyl components are as previously described.

"Cycloalkyl" means a non-aromatic mono-, multicyclic, or bridged ring system of 3 to 10 carbon atoms. The cycloalkyl group is optionally substituted by one or more halo, or alkyl. Exemplary monocyclic cycloalkyl rings include cyclopentyl, fluorocyclopentyl, cyclohexyl and cycloheptyl.

"Heterocycloalkyl" means a non-aromatic mono-, bi- or tricyclic, or bridged hydrocarbon ring system in which one or more of the atoms in the ring system is or are element(s) other than carbon, for example nitrogen, oxygen or sulfur. Preferred heterocycloalkyl groups contain rings with a ring size of 3-6 ring atoms. Exemplary heterocycloalkyl groups pyrrolidine, piperidine, tetrahydropyran, tetrahydrofuran, tetrahydrothiopyran, and tetrahydrothiofuran.

"Cycloalkylalkyl" means a group in which the cycloalkyl and alkyl components are as previously described.

"Heteroycloalkylalkyl" means a group in which the cycloalkyl and alkyl components are as previously described.

The term "optionally substituted with deuterium" means that one or more hydrogen atoms in the referenced moiety or compound may be replaced with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula A:

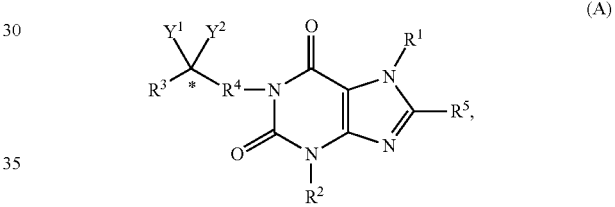

(A)

or a pharmaceutically acceptable salt thereof, wherein:

$R^1$ and $R^2$ are each independently selected from hydrogen, —($C_1$-$C_4$)alkyl, or —($C_1$-$C_4$)alkylene-O—($C_1$-$C_2$)alkyl, wherein the alkyl and alkylene groups at each instance are independently and optionally substituted with deuterium;

$R^3$ is selected from —$CH_3$, —$CH_2D$, —$CHD_2$ and —$CD_3$;

$R^4$ is n-butylene optionally substituted with deuterium;

$R^5$ is selected from hydrogen, deuterium, alkyl, cycloalkyl, heterocycloalkyl, cycloalkylalkyl, heterocycloalkylalkyl, aryl, and heteroaryl, wherein each of the alkyl, cycloalkyl, heterocycloalkyl, cycloalkylalkyl, heterocycloalkylalkyl, aryl, and heteroaryl is optionally substituted and wherein one or more hydrogen atoms in the alkyl, cycloalkyl, heterocycloalkyl, cycloalkylalkyl, heterocycloalkylalkyl, aryl, or heteroaryl or optional substituent thereof is optionally replaced with a corresponding number of deuterium atoms; and either (a) $Y^1$ and $Y^2$ are each fluorine, or are taken together with the carbon to which they are bound to form C=O or (b) $Y^1$ is selected from fluorine and OH; and $Y^2$ is selected from hydrogen, deuterium, —$CH_3$, —$CH_2D$, —$CHD_2$ and —$CD_3$; with the provisos that:

when $Y^1$ and $Y^2$ are taken together with the carbon to which they are bound to form C=O, then at least one of $R^1$, $R^2$, $R^3$, $R^4$, and $R^5$ bears at least one deuterium atom; and when $Y^1$ is OH and $Y^2$ is hydrogen or $CH_3$, then at least one of $R^1$, $R^2$, $R^3$, $R^4$ and $R^5$ bears at least one deuterium atom.

In another embodiment, the compound of Formula A is other than the following:

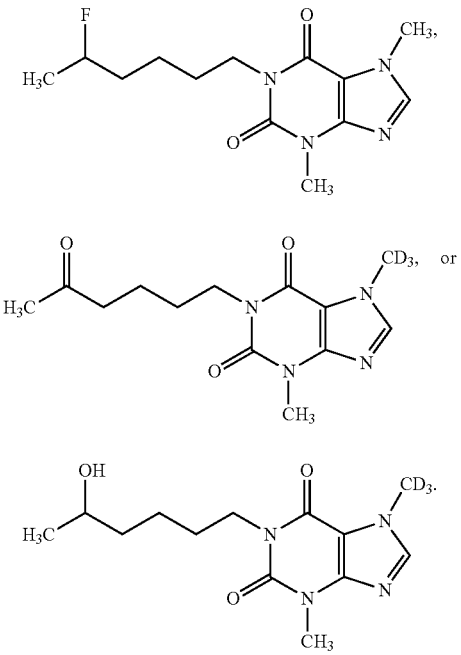

In another embodiment of Formula A, when $R^1$ and $R^2$ are each methyl optionally substituted with deuterium and $R^5$ is hydrogen or deuterium, then either: (i) $Y^1$ is fluoro; (ii) $Y^1$ is OH, and $Y^2$ is selected from —CH$_3$, —CH$_2$D, —CHD$_2$ and —CD$_3$.

In one aspect of this embodiment, the compound is not

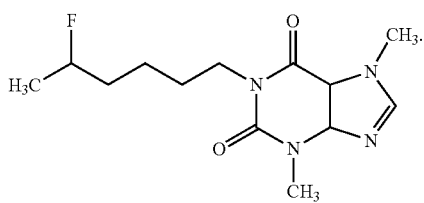

In a more specific aspect of this embodiment, at least one of $Y^2$, $R^1$, $R^2$, $R^3$, and $R^4$ bears at least one deuterium atom.

In still another embodiment of Formula A, $R^1$ and $R^2$ are each methyl optionally substituted with deuterium; $R^5$ is hydrogen or deuterium; and either: (a) $Y^1$ and $Y^2$ are taken together with the carbon atom to which they are bound to form =O, or (b) $Y^1$ is —OH and $Y^2$ is selected from hydrogen and deuterium, with the provisos that:

when $Y^1$ and $Y^2$ are taken together with the carbon to which they are bound to form C=O, then at least one of $R^1$, $R^2$, $R^3$, $R^4$, and $R^5$ bears at least one deuterium atom; and when $Y^1$ is OH, then at least one of $Y^2$, $R^1$, $R^2$, $R^3$, $R^4$ and $R^5$ bears at least one deuterium atom.

In another embodiment of Formula A, $R^5$ is D, the compound having Formula A1:

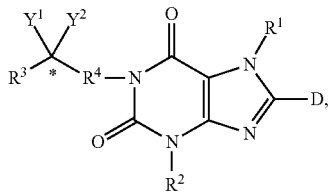

or a salt thereof, wherein $R^1$, $R^2$, $R^3$, $R^4$, $Y^1$ and $Y^2$ are as defined for Formula A.

In one aspect of Formula A1, $R^1$ and $R^2$ are each independently selected from —CH$_3$, —CH$_2$D, —CHD$_2$ and —CD$_3$; $R^3$ is selected from —CH$_3$, —CH$_2$D, —CHD$_2$ and —CD$_3$; $R^4$ is selected from —(CH$_2$)$_4$—, †-(CD$_2$)$_4$-, †-(CD$_2$)$_3$CH$_2$, and †-CD$_2$(CH$_2$)$_3$—, wherein "†" represents the portion of the $R^4$ moiety bound to C($Y^1$)($Y^2$) in the compound; and either (a) $Y^1$ is OH and $Y^2$ is selected from hydrogen and deuterium; or (b) $Y^1$ and $Y^2$ are taken together with the carbon to which they are attached to form C=O.

In a more specific aspect of Formula A1, $R^1$ and $R^2$ are each independently selected from —CH$_3$ and —CD$_3$; $R^3$ is selected from —CH$_3$ and —CD$_3$; $R^4$ is selected from —(CH$_2$)$_4$— and †-CD$_2$(CH$_2$)$_3$—; and either (a) $Y^1$ is OH and $Y^2$ is selected from hydrogen and deuterium; or (b) $Y^1$ and $Y^2$ are taken together with the carbon to which they are attached to form C=O.

In another aspect of Formula A1, $R^1$ and $R^2$ are each independently selected from —CH$_3$ and —CD$_3$; $R^3$ is selected from —CH$_3$ and —CD$_3$; $R^4$ is selected from —(CH$_2$)$_4$— and †-CD$_2$(CH$_2$)$_3$—; and $Y^1$ and $Y^2$ are taken together with the carbon to which they are attached to form C=O.

In another embodiment, the present invention provides a compound of Formula A, wherein $R^5$ is hydrogen, the compound having Formula I:

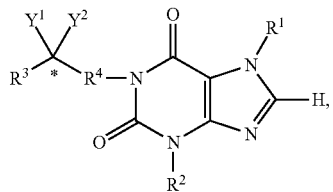

or a salt thereof, wherein:

$R^1$ and $R^2$ are each independently selected from hydrogen, —(C$_1$-C$_4$)alkyl, or —(C$_1$-C$_4$)alkylene-O—(C$_1$-C$_2$)alkyl, wherein the alkyl and alkylene groups at each instance are independently and optionally substituted with deuterium;

$R^3$ is selected from —CH$_3$, —CH$_2$D, —CHD$_2$ and —CD$_3$;

$R^4$ is n-butylene optionally substituted with deuterium; and either (a) $Y^1$ and $Y^2$ are each fluorine, or taken together with the carbon to which they are attached, form C=O; or (b) $Y^1$ is selected from fluorine and OH; and $Y^2$ is selected from hydrogen, deuterium, —CH$_3$, —CH$_2$D, —CHD$_2$ and —CD$_3$, with the provisos that:

when $Y^1$ and $Y^2$ are taken together with the carbon to which they are attached to form C=O, at least one of $R^1$, $R^2$, $R^3$ and $R^4$ bears at least one deuterium atom; and when $Y^1$ is OH and $Y^2$ is hydrogen or —$CH_3$, then at least one of $R^1$, $R^2$, $R^3$ and $R^4$ bears at least one deuterium atom.

In a more specific embodiment of Formula I, $R^1$ and $R^2$ are each independently selected from —$CH_3$, —$CH_2D$, —$CHD_2$ and —$CD_3$; $R^3$ is selected from —$CH_3$, —$CH_2D$, —$CHD_2$ and —$CD_3$; $R^4$ is selected from —$(CH_2)_4$—, —$(CD_2)_4$-, †-$(CD_2)_3CH_2$, and †-$CD_2(CH_2)_3$—, wherein "†" represents the portion of the $R^4$ moiety bound to $C(Y^1)(Y^2)$ in the compound; and either: $Y^1$ is OH and $Y^2$ is selected from hydrogen and deuterium; or $Y^1$ and $Y^2$ are taken together with the carbon to which they are attached to form C=O.

In another aspect of Formula I, $R^1$ and $R^2$ are each independently selected from —$CH_3$ and —$CD_3$; $R^3$ is selected from —$CH_3$ and —$CD_3$; $R^4$ is selected from —$(CH_2)_4$— and †-$CD_2(CH_2)_3$—; and either: $Y^1$ is OH and $Y^2$ is selected from hydrogen and deuterium; or $Y^1$ and $Y^2$ are taken together with the carbon to which they are attached to form C=O.

In another aspect of Formula I, $R^1$ and $R^2$ are each independently selected from —$CH_3$ and —$CD_3$; $R^3$ is selected from —$CH_3$ and —$CD_3$; $R^4$ is selected from —$(CH_2)_4$— and †-$CD_2(CH_2)_3$—; and $Y^1$ and $Y^2$ are taken together with the carbon to which they are attached to form C=O.

In another embodiment, in any of the aspects set forth above, the compound of Formula I is other than the following:

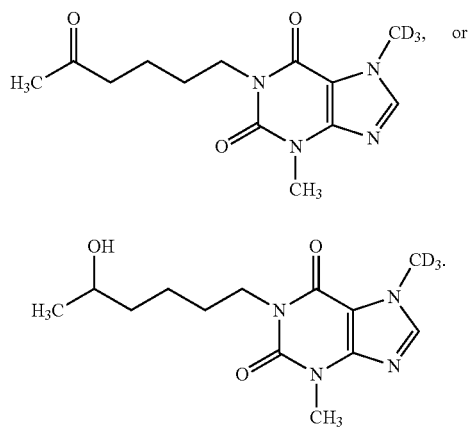

In yet another embodiment, in any of the aspects set forth above, the compound of Formula I is other than the following:

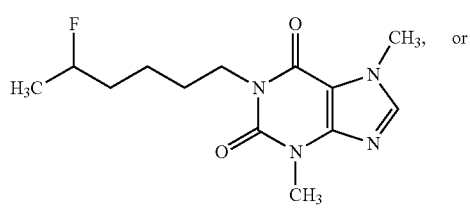

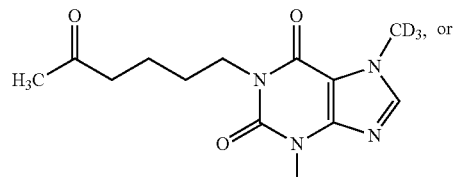

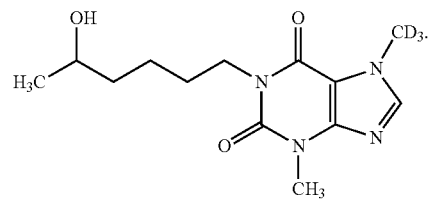

In yet another embodiment, in any of the aspects set forth above, the compound of Formula I is other than the following:

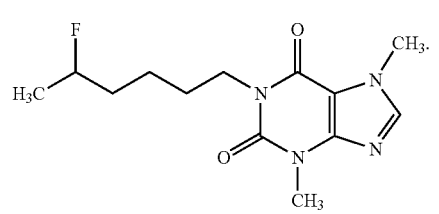

Another embodiment of the present invention provides a compound of Formula II:

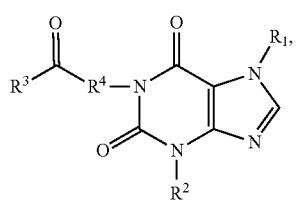

(II)

or a salt thereof, wherein:
$R^1$ and $R^2$ are each independently selected from hydrogen, —$(C_1-C_4)$alkyl, or —$(C_1-C_4)$alkylene-O—$(C_1-C_2)$alkyl, wherein the alkyl and alkylene groups at each instance are independently and optionally substituted with deuterium;
$R^3$ is selected from —$CH_3$, —$CH_2D$, —$CHD_2$ and —$CD_3$;
$R^4$ is n-butylene optionally substituted with deuterium; and
wherein at least one of $R^2$, $R^3$ and $R^4$ bears at least one deuterium atom.

One embodiment relates to a compound of Formula A, A1, I, or II, wherein $R^2$ and $R^3$ are each independently selected from —$CH_3$, —$CH_2D$, —$CHD_2$ and —$CD_3$.

Another embodiment relates to a compound of Formula A, A1, I, or II, wherein $R^2$ and $R^3$ are each independently selected from —$CH_3$, and —$CD_3$.

Another embodiment relates to a compound of Formula A, A1, I, or II, wherein $R^1$ is selected from hydrogen, $(C_1-C_3)$alkyl, and $(C_1-C_2)$alkylene-O$(C_1-C_2)$alkyl.

Another embodiment relates to a compound of Formula A, A1, I, or II, wherein $R^1$ is hydrogen, —$CH_3$, —$CD_3$, —$CH_2CH_2CH_3$, —$CD_2CH_2CH_3$, —$CD_2CD_2CH_3$, —$CD_2CD_2CD_3$, —$CH_2OCH_2CH_3$, —$CH_2OCD_2CH_3$, —$CH_2OCD_2CD_3$, —$CD_2OCH_2CH_3$, —$CD_2OCD_2CH_3$, or —$CD_2OCD_2CD_3$.

Another embodiment relates to a compound of Formula A, wherein $R^5$ is selected from hydrogen, deuterium, alkyl, cycloalkyl, heterocycloalkyl, cycloalkylalkyl, and heterocycloalkylalkyl, wherein each of alkyl, cycloalkyl, heterocycloalkyl, cycloalkylalkyl, and heterocycloalkylalkyl may be optionally substituted.

In other embodiments of Formula A, A1 or I:
a) each methylene unit in $R^4$ is selected from —$CH_2$— and —$CD_2$-; more specifically $R^4$ is selected from —$(CH_2)_4$—, —$(CD_2)_4$-, †-$CD_2(CH_2)_3$— and †-$(CD_2)_3CH_2$—, wherein "†" represents the point where $R^4$ is attached to $C(Y')(Y^2)$ in the compound;
b) when $Y^1$ is F, $Y^2$ is selected from hydrogen, —$CH_3$, —$CH_2D$, —$CHD_2$ and —$CD_3$; or
c) when $Y^1$ is F, $Y^2$ fluorine; or
d) when $Y^1$ and $Y^2$ are not the same and $Y^2$ and $R^3$ are not the same and $Y^1$ and $R^3$ are not the same, the stereochemistry at "*" is represented by:

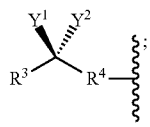

or
e) when $Y^1$ and $Y^2$ are not the same and $Y^2$ and $R^3$ are not the same and $Y^1$ and $R^3$ are not the same, the stereochemistry at "*" is represented by:

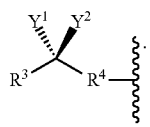

In other embodiments of Formula A, A1 or I, $R^1$ is —$CD_3$; $R^2$ and $R^3$ are —$CH_3$; $Y^1$ and $Y^2$ are taken together to form C=O; and $R^4$ is selected from —$(CH_2)_4$—, —$(CD_2)_4$-, †-$CD_2(CH_2)_3$— and †-$(CD_2)_3CH_2$—.

In other embodiments of Formula A, A1 or I, $R^1$ is —$CD_3$; $R^2$ and $R^3$ are —$CH_3$; $Y^1$ and $Y^2$ are taken together to form C=O; and $R^4$ is selected from —$(CH_2)_4$—, and —$(CD_2)_4$-.

In other embodiments of Formula A, A1 or I, $R^1$ is —$CD_3$; $R^2$ and $R^3$ are —$CH_3$; $R^4$ is —$(CH_2)_4$—; $Y^1$ is fluoro; and $Y^2$ is selected from deuterium, —$CH_2D$, —$CHD_2$ and —$CD_3$.

In other embodiments of Formula A, A1 or I, $R^1$ is —$CD_3$; $R^2$ and $R^3$ are —$CH_3$; $R^4$ is —$(CH_2)_4$—; $Y^1$ is fluoro; and $Y^2$ is fluorine.

In other embodiments of Formula A or A1, $R^1$ is —$CD_3$; $R^2$ and $R^3$ are —$CH_3$; $R^4$ is —$(CH_2)_4$—; $R^5$ is deuterium; $Y^1$ is fluoro; and $Y^2$ is selected from deuterium, —$CH_2D$, —$CHD_2$ and —$CD_3$.

In other embodiments of Formula A or A1, $R^1$ is —$CD_3$; $R^2$ and $R^3$ are —$CH_3$; $R^4$ is —$(CH_2)_4$—; $R^5$ is deuterium; $Y^1$ is fluoro; and $Y^2$ is fluorine.

In other embodiments of Formula A, A1 or I, $Y^1$ is F; $Y^2$ is selected from hydrogen; $R^3$ is —$CH_3$; and $R^4$ is —$(CH_2)_4$—.

In other embodiments of Formula A, A1 or I, $Y^1$ is F; $Y^2$ is fluorine; $R^3$ is —$CH_3$; and $R^4$ is —$(CH_2)_4$—.

One embodiment provides a compound of Formula B:

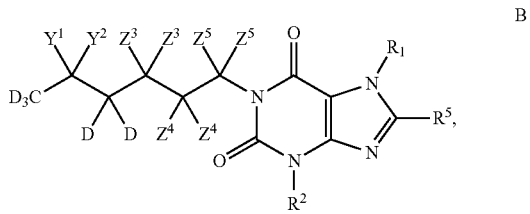

or a pharmaceutically acceptable salt thereof, wherein each of $R^1$ and $R^2$ is independently selected from —$CH_3$ and —$CD_3$; $R^5$ is hydrogen or deuterium; each $Z^3$ is hydrogen or deuterium; each $Z^4$ is hydrogen or deuterium; each $Z^5$ is hydrogen or deuterium; and either (a) $Y^1$ is OH, and $Y^2$ is hydrogen or deuterium, or (b) $Y^1$ and $Y^2$ are taken together with the carbon to which they are attached to form C=O.

One embodiment provides a compound of Formula B, wherein each $Z^3$, $Z^4$ and $Z^5$ is hydrogen. In one aspect, $R^1$ and $R^2$ are each —$CD_3$. In another aspect $R^5$ is deuterium. In another aspect, $Y^1$ and $Y^2$ are taken together with the carbon to which they are attached to form C=O. In still another aspect, $Y^1$ and is OH, and $Y^2$ is hydrogen or deuterium.

Another embodiment provides a compound of Formula B, wherein each $Z^3$, $Z^4$ and $Z^5$ is deuterium. In one aspect, $R^1$ and $R^2$ are each —CD3. In another aspect $R^5$ is deuterium. In another aspect, $Y^1$ and $Y^2$ are taken together with the carbon to which they are attached to form C=O. In still another aspect, $Y^1$ and is OH, and $Y^2$ is hydrogen or deuterium.

Yet another embodiment provides a compound of Formula B, wherein $R^1$ and $R^2$ are each —$CD_3$. In one aspect, $R^5$ is deuterium. In another aspect, each $Z^3$, $Z^4$ and $Z^5$ is hydrogen and $R^5$ is deuterium. In another aspect, each $Z^3$, $Z^4$ and $Z^5$ is deuterium and $R^5$ is deuterium.

A further embodiment provides a compound of Formula B, wherein $Y^1$ and $Y^2$ are taken together with the carbon to which they are attached to form C=O. In one aspect, $R^5$ is deuterium. In another aspect, each $Z^3$, $Z^4$ and $Z^5$ is hydrogen and $R^5$ is deuterium. In another aspect, each $Z^3$, $Z^4$ and $Z^5$ is deuterium and $R^5$ is deuterium. In another aspect, $R^1$ and $R^2$ are each —$CD_3$. In another aspect, $R^1$ and $R^2$ are each —$CD_3$ and $R^5$ is deuterium. In another aspect, $R^1$ and $R^2$ are each —$CD_3$, and each $Z^3$, $Z^4$ and $Z^5$ is deuterium. In another aspect, $R^1$ and $R^2$ are each —$CD_3$, each $Z^3$, $Z^4$ and $Z^5$ is deuterium and $R^5$ is deuterium. In another aspect, $R^1$ and $R^2$ are each —$CD_3$, and each $Z^3$, $Z^4$ and $Z^5$ is hydrogen. In another aspect, $R^1$ and $R^2$ are each —$CD_3$, each $Z^3$, $Z^4$ and $Z^5$ is hydrogen and $R^5$ is deuterium A still further embodiment provides a compound of Formula B, $Y^1$ and is OH, and $Y^2$ is hydrogen or deuterium. In one aspect, $R^5$ is deuterium. In another aspect, each $Z^3$, $Z^4$ and $Z^5$ is hydrogen and $R^5$ is deuterium. In another aspect, each $Z^3$, $Z^4$ and $Z^5$ is deuterium and $R^5$ is deuterium. In another aspect, $R^1$ and $R^2$ are each —$CD_3$. In another aspect, $R^1$ and $R^2$ are each —$CD_3$ and $R^5$ is deuterium. In another aspect, $R^1$ and $R^2$ are each —$CD_3$, and each $Z^3$, $Z^4$ and $Z^5$ is deuterium. In another aspect, $R^1$ and $R^2$ are each —$CD_3$, each $Z^3$, $Z^4$ and $Z^5$ is deuterium and $R^5$ is deuterium. In another aspect, $R^1$ and $R^2$ are each —$CD_3$, and each $Z^3$, $Z^4$ and $Z^5$ is hydrogen. In another aspect, $R^1$ and $R^2$ are each —$CD_3$, each $Z^3$, $Z^4$ and $Z^5$ is hydrogen and $R^5$ is deuterium Another embodiment provides a compound of Formula B, wherein $R^5$ is deuterium.

Another embodiment provides a compound of Formula B, wherein $R^5$ is deuterium, $Z^3$, $Z^4$ and $Z^5$ is hydrogen and $R^1$ is —$CD_3$.

Specific examples of compounds of Formula A, A1, I, or II include those shown in Tables 1-6 (below) or pharmaceutically acceptable salts thereof, wherein "†" represents the portion of the $R^4$ moiety bound to $C(Y^1)(Y^2)$ in the compound. In the tables, compounds designated as "(R)" or "(S)" refer to the stereochemistry at the carbon bearing the $Y^1$ substituent. Compounds lacking either designation and containing a chiral carbon atom bound to $Y^1$ and $Y^2$ are intended to represent a racemic mixture of enantiomers.

TABLE 1

Examples of Specific Compounds of Formula I. Deuterated and/or Fluorinated Analogs of Pentoxifylline and its Metabolites.

| Compound | $R^1$ | $R^2$ | $R^3$ | $R^4$ | $Y^1$ | $Y^2$ |
|---|---|---|---|---|---|---|
| 100 | $CD_3$ | $CH_3$ | $CH_3$ | $(CH_2)_4$ | taken together as =O | |
| 101 | $CD_3$ | $CD_3$ | $CH_3$ | $(CH_2)_4$ | taken together as =O | |
| 102 | $CH_3$ | $CD_3$ | $CH_3$ | $(CH_2)_4$ | taken together as =O | |
| 103 | $CD_3$ | $CD_3$ | $CD_3$ | $(CD_2)_4$ | taken together as =O | |
| 104 | $CH_3$ | $CH_3$ | $CH_3$ | $(CD_2)_4$ | taken together as =O | |
| 105 | $CD_3$ | $CD_3$ | $CD_3$ | $(CD_2)_4$ | taken together as =O | |
| 106 | $CH_3$ | $CD_3$ | $CD_3$ | $(CD_2)_4$ | taken together as =O | |
| 107 | $CH_3$ | $CH_3$ | $CD_3$ | †$CD_2(CH_2)_3$ | taken together as =O | |
| 108 | $CH_3$ | $CH_3$ | $CD_3$ | †$(CD_2)_3CH_2$ | taken together as =O | |
| 109 | $CH_3$ | $CD_3$ | $CD_3$ | †$CD_2(CH_2)_3$ | taken together as =O | |
| 110 | $CD_3$ | $CD_3$ | $CD_3$ | †$(CD_2)_3CH_2$ | taken together as =O | |
| 111 | $CH_3$ | $CD_3$ | $CD_3$ | †$CD_2(CH_2)_3$ | taken together as =O | |
| 112 | $CD_3$ | $CD_3$ | $CD_3$ | †$(CD_2)_3CH_2$ | taken together as =O | |
| 113 | $CD_3$ | $CD_3$ | $CD_3$ | †$CD_2(CH_2)_3$ | taken together as =O | |
| 114 | $CD_3$ | $CD_3$ | $CD_3$ | †$(CD_2)_3CH_2$ | taken together as =O | |
| 115 | $CD_3$ | $CD_3$ | $CH_3$ | $(CH_2)_4$ | OH | H |
| 116 | $CD_3$ | $CH_3$ | $CH_3$ | $(CH_2)_4$ | OH | H |
| 117 | $CH_3$ | $CD_3$ | $CH_3$ | $(CH_2)_4$ | OH | H |
| 118 | $CD_3$ | $CD_3$ | $CD_3$ | †$CD_2(CH_2)_3$ | OH | H |
| 119 | $CD_3$ | $CH_3$ | $CD_3$ | †$CD_2(CH_2)_3$ | OH | H |
| 119(R) | $CD_3$ | $CH_3$ | $CD_3$ | †$CD_2(CH_2)_3$ | (R)OH | H |
| 120 | $CH_3$ | $CD_3$ | $CD_3$ | †$CD_2(CH_2)_3$ | OH | H |
| 121 | $CD_3$ | $CD_3$ | $CD_3$ | †$CD_2(CH_2)_3$ | OH | H |
| 122 | $CD_3$ | $CD_3$ | $CD_3$ | $(CD_2)_4$ | OH | H |
| 123 | $CD_3$ | $CH_3$ | $CD_3$ | $(CD_2)_4$ | OH | H |
| 124 | $CH_3$ | $CD_3$ | $CD_3$ | $(CD_2)_4$ | OH | H |
| 125 | $CH_3$ | $CH$ | $CD_3$ | $(CD_2)_4$ | OH | H |
| 126 | $CD_3$ | $CD_3$ | $CD_3$ | †$(CD_2)_3CH_2$ | OH | H |
| 127 | $CD_3$ | $CH_3$ | $CD_3$ | †$(CD_2)_3CH_2$ | OH | H |
| 128 | $CH_3$ | $CD_3$ | $CD_3$ | †$(CD_2)_3CH_2$ | OH | H |
| 129 | $CH_3$ | $CH_3$ | $CD_3$ | †$(CD_2)_3CH_2$ | OH | H |
| 130 | $CD_3$ | $CD_3$ | $CH_3$ | $(CH_2)_4$ | OH | D |
| 131 | $CD_3$ | $CH_3$ | $CH_3$ | $(CH_2)_4$ | OH | D |
| 131(R) | $CD_3$ | $CH_3$ | $CH_3$ | $(CH_2)_4$ | (R)OH | D |
| 131(S) | $CD_3$ | $CH_3$ | $CH_3$ | $(CH_2)_4$ | (S)OH | D |
| 132 | $CH_3$ | $CD_3$ | $CH_3$ | $(CH_2)_4$ | OH | D |
| 133 | $CH_3$ | $CH_3$ | $CH_3$ | $(CH_2)_4$ | OH | D |
| 133(R) | $CH_3$ | $CH_3$ | $CH_3$ | $(CH_2)_4$ | (R)OH | D |
| 133(S) | $CH_3$ | $CH_3$ | $CH_3$ | $(CH_2)_4$ | (S)OH | D |
| 134 | $CD_3$ | $CH_3$ | $CD_3$ | †$CD_2(CH_2)_3$ | OH | D |
| 135 | $CD_3$ | $CH_3$ | $CD_3$ | †$CD_2(CH_2)_3$ | OH | D |
| 135(R) | $CD_3$ | $CH_3$ | $CD_3$ | †$CD_2(CH_2)_3$ | (R)OH | D |
| 136 | $CH_3$ | $CD_3$ | $CD_3$ | †$CD_2(CH_2)_3$ | OH | D |
| 137 | $CH_3$ | $CH_3$ | $CD_3$ | †$CD_2(CH_2)_3$ | OH | D |
| 138 | $CD_3$ | $CD_3$ | $CD_3$ | $(CD_2)_4$ | OH | D |
| 139 | $CD_3$ | $CH_3$ | $CD_3$ | $(CD_2)_4$ | OH | D |
| 140 | $CH_3$ | $CD_3$ | $CD_3$ | $(CD_2)_4$ | OH | D |
| 141 | $CH_3$ | $CH_3$ | $CD_3$ | $(CD_2)_4$ | OH | D |
| 142 | $CD_3$ | $CD_3$ | $CD_3$ | †$(CD_2)_3CH_2$ | OH | D |
| 143 | $CD_3$ | $CH_3$ | $CD_3$ | †$(CD_2)_3CH_2$ | OH | D |
| 144 | $CH_3$ | $CD_3$ | $CD_3$ | †$(CD_2)_3CH_2$ | OH | D |
| 145 | $CH_3$ | $CH_3$ | $CD_3$ | †$(CD_2)_3CH_2$ | OH | D |
| 146 | $CD_3$ | $CD_3$ | $CH_3$ | $(CH_2)_4$ | F | H |
| 147 | $CD_3$ | $CH_3$ | $CH_3$ | $(CH_2)_4$ | F | H |
| 148 | $CH_3$ | $CD_3$ | $CH_3$ | $(CH_2)_4$ | F | H |
| 149 | $CH_3$ | $CH_3$ | $CH_3$ | $(CH_2)_4$ | F | H |
| 150 | $CD_3$ | $CD_3$ | $CH_3$ | $(CH_2)_4$ | F | F |
| 151 | $CD_3$ | $CH_3$ | $CH_3$ | $(CH_2)_4$ | F | F |
| 152 | $CH_3$ | $CD_3$ | $CH_3$ | $(CH_2)_4$ | F | F |
| 153 | $CH_3$ | $CH_3$ | $CH_3$ | $(CH_2)_4$ | F | F |

Table 1 above shows examples of specific compounds of Formula I. These examples are deuterated and/or fluorinated analogs of pentoxifylline and its metabolites.

TABLE 2

Examples of Specific Compounds of Formula I Where $R^1$ is H and $Y^2$ is $CH_3$ or $CD_3$.

| Compound | $R^1$ | $R^2$ | $R^3$ | $R^4$ | $Y^1$ | $Y^2$ |
|---|---|---|---|---|---|---|
| 200 | H | $CD_3$ | $CH_3$ | $(CH_2)_4$ | OH | $CH_3$ |
| 201 | H | $CD_3$ | $CD_3$ | $(CH_2)_4$ | OH | $CD_3$ |
| 202 | H | $CH_3$ | $CD_3$ | $(CH_2)_4$ | OH | $CD_3$ |
| 203 | H | $CD_3$ | $CD_3$ | †$CD_2(CH_2)_3$ | OH | $CD_3$ |
| 204 | H | $CH_3$ | $CD_3$ | †$CD_2(CH_2)_3$ | OH | $CD_3$ |
| 205 | H | $CD_3$ | $CD_3$ | $(CD_2)_4$ | OH | $CD_3$ |
| 206 | H | $CH_3$ | $CD_3$ | $(CD_2)_4$ | OH | $CD_3$ |
| 207 | H | $CD_3$ | $CH_3$ | $(CH_2)_4$ | F | $CH_3$ |
| 208 | H | $CH_3$ | $CH_3$ | $(CH_2)_4$ | F | $CH_3$ |
| 209 | H | $CD_3$ | $CD_3$ | $(CD_2)_4$ | F | $CD_3$ |
| 210 | H | $CH_3$ | $CD_3$ | $(CD_2)_4$ | F | $CD_3$ |

Table 2 above shows examples of specific compounds of Formula I where $R^1$ is H and $Y^2$ is $CH_3$ or $CD_3$. These compounds include deuterated and fluorinated analogs of Albifylline (HWA-138). Albifylline has been studied for uses that are associated with pentoxifylline.

TABLE 3

Specific Examples of Formula I Where $R^1$ is —$CH_2$—O—$CH_2CH_3$ Optionally Substituted with Deuterium.

| Compound | $R^1$ | $R^2$ | $R^3$ | $R^4$ | $Y^1$ | $Y^2$ |
|---|---|---|---|---|---|---|
| 250 | $CD_2OCD_2CD_3$ | $CD_3$ | $CH_3$ | $(CH_2)_4$ | OH | $CH_3$ |
| 251 | $CD_2OCH_2CH_3$ | $CD_3$ | $CH_3$ | $(CH_2)_4$ | OH | $CH_3$ |
| 252 | $CH_2OCH_2CH_3$ | $CD_3$ | $CH_3$ | $(CH_2)_4$ | OH | $CH_3$ |
| 253 | $CD_2OCD_2CD_3$ | $CH_3$ | $CH_3$ | $(CH_2)_4$ | OH | $CH_3$ |
| 254 | $CD_2OCH_2CH_3$ | $CH_3$ | $CH_3$ | $(CH_2)_4$ | OH | $CH_3$ |
| 255 | $CD_2OCD_2CD_3$ | $CD_3$ | $CD_3$ | $(CH_2)_4$ | OH | $CD_3$ |
| 256 | $CD_2OCH_2CH_3$ | $CD_3$ | $CD_3$ | $(CH_2)_4$ | OH | $CD_3$ |
| 257 | $CH_2OCH_2CH_3$ | $CD_3$ | $CD_3$ | $(CH_2)_4$ | OH | $CD_3$ |
| 258 | $CD_2OCD_2CD_3$ | $CH_3$ | $CD_3$ | $(CH_2)_4$ | OH | $CD_3$ |
| 259 | $CD_2OCH_2CH_3$ | $CH_3$ | $CD_3$ | $(CH_2)_4$ | OH | $CD_3$ |
| 260 | $CH_2OCH_2CH_3$ | $CH_3$ | $CD_3$ | $(CH_2)_4$ | OH | $CD_3$ |
| 261 | $CD_2OCD_2CD_3$ | $CD_3$ | $CD_3$ | †$CD_2(CH_2)_3$ | OH | $CD_3$ |
| 262 | $CD_2OCH_2CH_3$ | $CD_3$ | $CD_3$ | †$CD_2(CH_2)_3$ | OH | $CD_3$ |
| 263 | $CH_2OCH_2CH_3$ | $CD_3$ | $CD_3$ | †$CD_2(CH_2)_3$ | OH | $CD_3$ |
| 264 | $CD_2OCD_2CD_3$ | $CH_3$ | $CD_3$ | †$CD_2(CH_2)_3$ | OH | $CD_3$ |
| 265 | $CD_2OCH_2CH_3$ | $CH_3$ | $CD_3$ | †$CD_2(CH_2)_3$ | OH | $CD_3$ |
| 266 | $CH_2OCH_2CH_3$ | $CH_3$ | $CD_3$ | †$CD_2(CH_2)_3$ | OH | $CD_3$ |
| 267 | $CD_2OCD_2CD_3$ | $CD_3$ | $CD_3$ | $(CD_2)_4$ | OH | $CD_3$ |
| 268 | $CD_2OCH_2CH_3$ | $CD_3$ | $CD_3$ | $(CD_2)_4$ | OH | $CD_3$ |
| 269 | $CH_2OCH_2CH_3$ | $CD_3$ | $CD_3$ | $(CD_2)_4$ | OH | $CD_3$ |
| 270 | $CD_2OCD_2CD_3$ | $CH_3$ | $CD_3$ | $(CD_2)_4$ | OH | $CD_3$ |
| 271 | $CD_2OCH_2CH_3$ | $CH_3$ | $CD_3$ | $(CD_2)_4$ | OH | $CD_3$ |
| 272 | $CH_2OCH_2CH_3$ | $CH_3$ | $CD_3$ | $(CD_2)_4$ | OH | $CD_3$ |
| 273 | $CD_2OCD_2CD_3$ | $CD_3$ | $CH_3$ | $(CH_2)_4$ | F | $CH_3$ |

TABLE 3-continued

Specific Examples of Formula I Where $R^1$ is
—$CH_2$—O—$CH_2CH_3$ Optionally
Substituted with Deuterium.

| Compound | $R^1$ | $R^2$ | $R^3$ | $R^4$ | $Y^1$ | $Y^2$ |
|---|---|---|---|---|---|---|
| 274 | $CD_2OCH_2CH_3$ | $CD_3$ | $CH_3$ | $(CH_2)_4$ | F | $CH_3$ |
| 275 | $CH_2OCH_2CH_3$ | $CD_3$ | $CH_3$ | $(CH_2)_4$ | F | $CH_3$ |
| 276 | $CD_2OCD_2CD_3$ | $CD_3$ | $CH_3$ | $(CH_2)_4$ | F | $CH_3$ |
| 277 | $CD_2OCH_2CH_3$ | $CH_3$ | $CH_3$ | $(CH_2)_4$ | F | $CH_3$ |
| 278 | $CH_2OCH_2CH_3$ | $CH_3$ | $CH_3$ | $(CH_2)_4$ | F | $CH_3$ |
| 279 | $CD_2OCD_2CD_3$ | $CD_3$ | $CD_3$ | $(CD_2)_4$ | F | $CD_3$ |
| 280 | $CD_2OCH_2CH_3$ | $CD_3$ | $CD_3$ | $(CD_2)_4$ | F | $CD_3$ |
| 281 | $CH_2OCH_2CH_3$ | $CD_3$ | $CD_3$ | $(CD_2)_4$ | F | $CD_3$ |
| 282 | $CD_2OCD_2CD_3$ | $CH_3$ | $CD_3$ | $(CD_2)_4$ | F | $CD_3$ |
| 283 | $CD_2OCH_2CH_3$ | $CH_3$ | $CD_3$ | $(CD_2)_4$ | F | $CD_3$ |
| 284 | $CH_2OCH_2CH_3$ | $CH_3$ | $CD_3$ | $(CD_2)_4$ | F | $CD_3$ |

Table 3 above shows examples of specific compounds of Formula I where $R^1$ is —$CH_2$—O—$CH_2CH_3$, optionally substituted with deuterium. In these examples, $Y^1$ is OH or F and $Y^2$ is $CH_3$ or $CD_3$. These compounds include deuterated and fluorinated analogs of torbafylline (HWA-448). Torbafylline has been studied for the treatment of depression, urinary incontinence, irritable bowel syndrome and multiple sclerosis.

TABLE 4

Specific Examples of Formula I Where $R^1$ is
—$CH_2CH_2CH_3$ Optionally Substituted
With Deuterium and $Y^1$ is OH or F.

| Compound | $R^1$ | $R^2$ | $R^3$ | $R^4$ | $Y^1$ | $Y^2$ |
|---|---|---|---|---|---|---|
| 300 | $CD_2CD_2CD_3$ | $CD_3$ | $CH_3$ | $(CH_2)_4$ | OH | $CH_3$ |
| 301 | $CD_2CH_2CH_3$ | $CD_3$ | $CH_3$ | $(CH_2)_4$ | OH | $CH_3$ |
| 302 | $CH_2CH_2CH_3$ | $CD_3$ | $CH_3$ | $(CH_2)_4$ | OH | $CH_3$ |
| 303 | $CD_2CD_2CD_3$ | $CH_3$ | $CH_3$ | $(CH_2)_4$ | OH | $CH_3$ |
| 304 | $CD_2CH_2CH_3$ | $CH_3$ | $CH_3$ | $(CH_2)_4$ | OH | $CH_3$ |
| 305 | $CD_2CD_2CD_3$ | $CD_3$ | $CD_3$ | $(CH_2)_4$ | OH | $CD_3$ |
| 306 | $CD_2CH_2CH_3$ | $CD_3$ | $CD_3$ | $(CH_2)_4$ | OH | $CD_3$ |
| 307 | $CH_2CH_2CH_3$ | $CD_3$ | $CD_3$ | $(CH_2)_4$ | OH | $CD_3$ |
| 308 | $CD_2CD_2CD_3$ | $CH_3$ | $CD_3$ | $(CH_2)_4$ | OH | $CD_3$ |
| 309 | $CD_2CH_2CH_3$ | $CH_3$ | $CD_3$ | $(CH_2)_4$ | OH | $CD_3$ |
| 310 | $CH_2CH_2CH_3$ | $CH_3$ | $CD_3$ | $(CH_2)_4$ | OH | $CD_3$ |
| 311 | $CD_2CD_2CD_3$ | $CD_3$ | $CD_3$ | $^\dagger CD_2(CH_2)_3$ | OH | $CD_3$ |
| 312 | $CD_2CH_2CH_3$ | $CD_3$ | $CD_3$ | $^\dagger CD_2(CH_2)_3$ | OH | $CD_3$ |
| 313 | $CH_2CH_2CH_3$ | $CD_3$ | $CD_3$ | $^\dagger CD_2(CH_2)_3$ | OH | $CD_3$ |
| 314 | $CD_2CD_2CD_3$ | $CH_3$ | $CD_3$ | $^\dagger CD_2(CH_2)_3$ | OH | $CD_3$ |
| 315 | $CD_2CH_2CH_3$ | $CH_3$ | $CD_3$ | $^\dagger CD_2(CH_2)_3$ | OH | $CD_3$ |
| 316 | $CH_2CH_2CH_3$ | $CH_3$ | $CD_3$ | $^\dagger CD_2(CH_2)_3$ | OH | $CD_3$ |
| 317 | $CD_2CD_2CD_3$ | $CD_3$ | $CD_3$ | $(CD_2)_4$ | OH | $CD_3$ |
| 318 | $CD_2CH_2CH_3$ | $CD_3$ | $CD_3$ | $(CD_2)_4$ | OH | $CD_3$ |
| 319 | $CH_2CH_2CH_3$ | $CD_3$ | $CD_3$ | $(CD_2)_4$ | OH | $CD_3$ |
| 320 | $CD_2CD_2CD_3$ | $CH_3$ | $CD_3$ | $(CD_2)_4$ | OH | $CD_3$ |
| 321 | $CD_2CH_2CH_3$ | $CH_3$ | $CD_3$ | $(CD_2)_4$ | OH | $CD_3$ |
| 322 | $CH_2CH_2CH_3$ | $CH_3$ | $CD_3$ | $(CD_2)_4$ | OH | $CD_3$ |
| 323 | $CD_2CD_2CD_3$ | $CD_3$ | $CH_3$ | $(CH_2)_4$ | F | $CH_3$ |
| 324 | $CD_2CH_2CH_3$ | $CD_3$ | $CH_3$ | $(CH_2)_4$ | F | $CH_3$ |
| 325 | $CH_2CH_2CH_3$ | $CD_3$ | $CH_3$ | $(CH_2)_4$ | F | $CH_3$ |
| 326 | $CD_2CD_2CD_3$ | $CH_3$ | $CH_3$ | $(CH_2)_4$ | F | $CH_3$ |
| 327 | $CD_2CH_2CH_3$ | $CH_3$ | $CH_3$ | $(CH_2)_4$ | F | $CH_3$ |
| 328 | $CH_2CH_2CH_3$ | $CH_3$ | $CH_3$ | $(CH_2)_4$ | F | $CH_3$ |
| 329 | $CD_2CD_2CD_3$ | $CD_3$ | $CD_3$ | $(CD_2)_4$ | F | $CD_3$ |
| 330 | $CD_2CH_2CH_3$ | $CD_3$ | $CD_3$ | $(CD_2)_4$ | F | $CD_3$ |
| 331 | $CH_2CH_2CH_3$ | $CD_3$ | $CD_3$ | $(CD_2)_4$ | F | $CD_3$ |
| 332 | $CD_2CD_2CD_3$ | $CH_3$ | $CD_3$ | $(CD_2)_4$ | F | $CD_3$ |
| 333 | $CD_2CH_2CH_3$ | $CH_3$ | $CD_3$ | $(CD_2)_4$ | F | $CD_3$ |
| 334 | $CH_2CH_2CH_3$ | $CH_3$ | $CD_3$ | $(CD_2)_4$ | F | $CD_3$ |

Table 4 above shows examples of specific compounds of Formula I where $R^1$ is —$CH_2CH_2CH_3$ optionally substituted with deuterium. In these examples, $Y^1$ is OH or F and $Y^2$ is $CH_3$ or $CD_3$. These compounds include deuterated and fluorinated analogs of A-802715. A-802715 has been studied for the treatment of septic shock and inhibition of effects of allograft reaction.

TABLE 5

Specific Examples of Formula I where $R^1$ is —$CH_2CH_2CH_3$ Optionally Substituted
With Deuterium and $Y^1$ and $Y^2$ Are Taken Together As =O

| Compound | $R^1$ | $R^2$ | $R^3$ | $R^4$ | $Y^1$ | $Y^2$ |
|---|---|---|---|---|---|---|
| 350 | $CD_2CD_2CD_3$ | $CD_3$ | $CH_3$ | $(CH_2)_4$ | taken together as =O | |
| 351 | $CD_2CH_2CH_3$ | $CD_3$ | $CH_3$ | $(CH_2)_4$ | taken together as =O | |
| 352 | $CH_2CH_2CH_3$ | $CD_3$ | $CH_3$ | $(CH_2)_4$ | taken together as =O | |
| 353 | $CD_2CD_2CD_3$ | $CH_3$ | $CH_3$ | $(CH_2)_4$ | taken together as =O | |
| 354 | $CD_2CH_2CH_3$ | $CH_3$ | $CH_3$ | $(CH_2)_4$ | taken together as =O | |
| 355 | $CD_2CD_2CD_3$ | $CD_3$ | $CD_3$ | $(CH_2)_4$ | taken together as =O | |
| 356 | $CD_2CH_2CH_3$ | $CD_3$ | $CD_3$ | $(CH_2)_4$ | taken together as =O | |
| 357 | $CH_2CH_2CH_3$ | $CD_3$ | $CD_3$ | $(CH_2)_4$ | taken together as =O | |
| 358 | $CD_2CD_2CD_3$ | $CH_3$ | $CD_3$ | $(CH_2)_4$ | taken together as =O | |
| 359 | $CD_2CH_2CH_3$ | $CH_3$ | $CD_3$ | $(CH_2)_4$ | taken together as =O | |
| 360 | $CH_2CH_2CH_3$ | $CH_3$ | $CD_3$ | $(CH_2)_4$ | taken together as =O | |
| 361 | $CD_2CD_2CD_3$ | $CD_3$ | $CD_3$ | $^\dagger CD_2(CH_2)_3$ | taken together as =O | |
| 362 | $CD_2CH_2CH_3$ | $CD_3$ | $CD_3$ | $^\dagger CD_2(CH_2)_3$ | taken together as =O | |
| 363 | $CH_2CH_2CH_3$ | $CD_3$ | $CD_3$ | $^\dagger CD_2(CH_2)_3$ | taken together as =O | |
| 364 | $CD_2CD_2CD_3$ | $CH_3$ | $CD_3$ | $^\dagger CD_2(CH_2)_3$ | taken together as =O | |
| 365 | $CD_2CH_2CH_3$ | $CH_3$ | $CD_3$ | $^\dagger CD_2(CH_2)_3$ | taken together as =O | |
| 366 | $CH_2CH_2CH_3$ | $CH_3$ | $CD_3$ | $^\dagger CD_2(CH_2)_3$ | taken together as =O | |
| 367 | $CD_2CD_2CD_3$ | $CD_3$ | $CD_3$ | $(CD_2)_4$ | taken together as =O | |
| 368 | $CD_2CH_2CH_3$ | $CD_3$ | $CD_3$ | $(CD_2)_4$ | taken together as =O | |
| 369 | $CH_2CH_2CH_3$ | $CD_3$ | $CD_3$ | $(CD_2)_4$ | taken together as =O | |
| 370 | $CD_2CD_2CD_3$ | $CH_3$ | $CD_3$ | $(CD_2)_4$ | taken together as =O | |
| 371 | $CD_2CH_2CH_3$ | $CH_3$ | $CD_3$ | $(CD_2)_4$ | taken together as =O | |
| 372 | $CH_2CH_2CH_3$ | $CH_3$ | $CD_3$ | $(CD_2)_4$ | taken together as =O | |

Table 5 above shows examples of specific compounds of Formula I where $R^1$ is —$CH_2CH_2CH_3$ optionally substituted with deuterium. In these examples, $Y^1$ and $Y^2$ are taken together with their intervening carbon to form a carbonyl. These compounds include deuterated analogs of propentofylline. Propentofylline has been studied for the treatment of Alzheimer's disease, neuropathic pain, traumatic brain injury, dysuria, retinal or optic nerve head damage, and peptic ulcers. It has also been studied for controlling intraocular pressure, stabilization of auto-regulation of cerebral blood flow and inhibition of effects of allograft reaction.

TABLE 6

Examples of Specific Compounds of Formula A. Deuterated and/or Fluorinated Analogs of Pentoxifylline and its Metabolites where $R^5$ is D

| Compound | $R^1$ | $R^2$ | $R^3$ | $R^4$ | $R^5$ | $Y^1$ | $Y^2$ |
|---|---|---|---|---|---|---|---|
| 400 | $CD_3$ | $CH_3$ | $CH_3$ | $(CH_2)_4$ | D | Taken together as =O | |
| 401 | $CD_3$ | $CD_3$ | $CH_3$ | $(CH_2)_4$ | D | Taken together as =O | |
| 402 | $CH_3$ | $CD_3$ | $CH_3$ | $(CH_2)_4$ | D | Taken together as =O | |
| 403 | $CD_3$ | $CH_3$ | $CH_3$ | $(CD_2)_4$ | D | Taken together as =O | |
| 404 | $CH_3$ | $CH_3$ | $CD_3$ | $(CD_2)_4$ | D | Taken together as =O | |
| 405 | $CD_3$ | $CH_3$ | $CD_3$ | $(CD_2)_4$ | D | Taken together as =O | |
| 406 | $CH_3$ | $CD_3$ | $CD_3$ | $(CD_2)_4$ | D | Taken together as =O | |
| 407 | $CH_3$ | $CH_3$ | $CD_3$ | †$CD_2(CH_2)_3$ | D | Taken together as =O | |
| 408 | $CH_3$ | $CH_3$ | $CD_3$ | †$(CD_2)_3CH_2$ | D | Taken together as =O | |
| 409 | $CD_3$ | $CH_3$ | $CD_3$ | †$CD_2(CH_2)_3$ | D | Taken together as =O | |
| 410 | $CD_3$ | $CH_3$ | $CD_3$ | †$(CD_2)_3CH_2$ | D | Taken together as =O | |
| 411 | $CH_3$ | $CD_3$ | $CD_3$ | †$CD_2(CH_2)_3$ | D | Taken together as =O | |
| 412 | $CH_3$ | $CD_3$ | $CD_3$ | †$(CD_2)_3CH_2$ | D | Taken together as =O | |
| 413 | $CD_3$ | $CD_3$ | $CD_3$ | †$CD_2(CH_2)_3$ | D | Taken together as =O | |
| 414 | $CD_3$ | $CD_3$ | $CD_3$ | †$(CD_2)_3CH_2$ | D | Taken together as =O | |
| 415 | $CD_3$ | $CD_3$ | $CH_3$ | $(CH_2)_4$ | D | OH | H |
| 416 | $CD_3$ | $CH_3$ | $CH_3$ | $(CH_2)_4$ | D | OH | H |
| 417 | $CH_3$ | $CD_3$ | $CH_3$ | $(CH_2)_4$ | D | OH | H |
| 418 | $CD_3$ | $CD_3$ | $CD_3$ | †$CD_2(CH_2)_3$ | D | OH | H |
| 419 | $CD_3$ | $CH_3$ | $CD_3$ | †$CD_2(CH_2)_3$ | D | OH | H |
| 419(R) | $CD_3$ | $CH_3$ | $CD_3$ | †$CD_2(CH_2)_3$ | D | (R)OH | H |
| 419(S) | $CD_3$ | $CH_3$ | $CD_3$ | †$CD_2(CH_2)_3$ | D | (S)OH | H |
| 420 | $CD_3$ | $CD_3$ | $CD_3$ | †$CD_2(CH_2)_3$ | D | OH | H |
| 421 | $CH_3$ | $CH_3$ | $CD_3$ | †$CD_2(CH_2)_3$ | D | OH | H |
| 422 | $CD_3$ | $CD_3$ | $CD_3$ | $(CD_2)_4$ | D | OH | H |
| 423 | $CD_3$ | $CH_3$ | $CD_3$ | $(CD_2)_4$ | D | OH | H |
| 424 | $CH_3$ | $CD_3$ | $CD_3$ | $(CD_2)_4$ | D | OH | H |
| 425 | $CH_3$ | $CH_3$ | $CD_3$ | $(CD_2)_4$ | D | OH | H |
| 426 | $CD_3$ | $CD_3$ | $CD_3$ | †$(CD_2)_3CH_2$ | D | OH | H |
| 427 | $CD_3$ | $CH_3$ | $CD_3$ | †$(CD_2)_3CH_2$ | D | OH | H |
| 428 | $CH_3$ | $CD_3$ | $CD_3$ | †$(CD_2)_3CH_2$ | D | OH | H |
| 429 | $CH_3$ | $CH_3$ | $CD_3$ | †$(CD_2)_3CH_2$ | D | OH | H |
| 430 | $CD_3$ | $CD_3$ | $CH_3$ | $(CH_2)_4$ | D | OH | D |
| 431 | $CD_3$ | $CH_3$ | $CH_3$ | $(CH_2)_4$ | D | OH | D |
| 432 | $CH_3$ | $CD_3$ | $CH_3$ | $(CH_2)_4$ | D | OH | D |
| 433 | $CH_3$ | $CH_3$ | $CH_3$ | $(CH_2)_4$ | D | OH | D |
| 434 | $CD_3$ | $CD_3$ | $CD_3$ | †$CD_2(CH_2)_3$ | D | OH | D |
| 435 | $CD_3$ | $CH_3$ | $CD_3$ | †$CD_2(CH_2)_3$ | D | OH | D |
| 435(R) | $CD_3$ | $CH_3$ | $CD_3$ | †$CD_2(CH_2)_3$ | D | (R)OH | D |
| 435(S) | $CD_3$ | $CH_3$ | $CD_3$ | †$CD_2(CH_2)_3$ | D | (S)OH | D |
| 436 | $CH_3$ | $CD_3$ | $CD_3$ | †$CD_2(CH_2)_3$ | D | OH | D |
| 437(R) | $CH_3$ | $CH_3$ | $CD_3$ | †$CD_2(CH_2)_3$ | D | (R)OH | D |
| 437(S) | $CH_3$ | $CH_3$ | $CD_3$ | †$CD_2(CH_2)_3$ | D | (S)OH | D |
| 437 | $CH_3$ | $CH_3$ | $CD_3$ | †$CD_2(CH_2)_3$ | D | OH | D |
| 438 | $CD_3$ | $CD_3$ | $CD_3$ | $(CD_2)_4$ | D | OH | D |
| 439 | $CD_3$ | $CH_3$ | $CD_3$ | $(CD_2)_4$ | D | OH | D |
| 440 | $CH_3$ | $CD_3$ | $CD_3$ | $(CD_2)_4$ | D | OH | D |
| 441 | $CH_3$ | $CH_3$ | $CD_3$ | $(CD_2)_4$ | D | OH | D |
| 442 | $CD_3$ | $CD_3$ | $CD_3$ | †$(CD_2)_3CH_2$ | D | OH | D |
| 443 | $CD_3$ | $CH_3$ | $CD_3$ | †$(CD_2)_3CH_2$ | D | OH | D |
| 444 | $CH_3$ | $CD_3$ | $CD_3$ | †$(CD_2)_3CH_2$ | D | OH | D |
| 445 | $CH_3$ | $CH_3$ | $CD_3$ | †$(CD_2)_3CH_2$ | D | OH | D |
| 446 | $CD_3$ | $CD_3$ | $CH_3$ | $(CH_2)_4$ | D | F | H |
| 447 | $CH_3$ | $CD_3$ | $CH_3$ | $(CH_2)_4$ | D | F | H |
| 448 | $CD_3$ | $CH_3$ | $CH_3$ | $(CH_2)_4$ | D | F | H |
| 449 | $CH_3$ | $CH_3$ | $CH_3$ | $(CH_2)_4$ | D | F | H |
| 450 | $CD_3$ | $CD_3$ | $CH_3$ | $(CH_2)_4$ | D | F | F |
| 451 | $CD_3$ | $CH_3$ | $CH_3$ | $(CH_2)_4$ | D | F | F |
| 452 | $CH_3$ | $CD_3$ | $CH_3$ | $(CH_2)_4$ | D | F | F |
| 453 | $CH_3$ | $CH_3$ | $CH_3$ | $(CH_2)_4$ | D | F | F |

Table 6 above shows examples of specific compounds of Formula A. These examples are deuterated and/or fluorinated analogs of pentoxifylline and its metabolites where $R^5$ is deuterium.

In one aspect of the above embodiment, the compound is not any one of Compounds 100, 116, or 149.
Examples of specific compounds of this invention include the following:
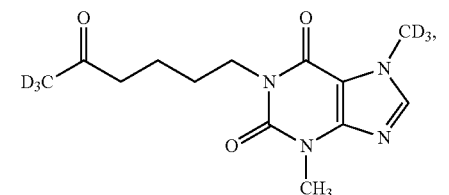
99
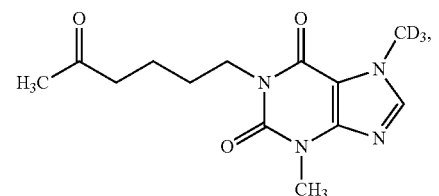
101
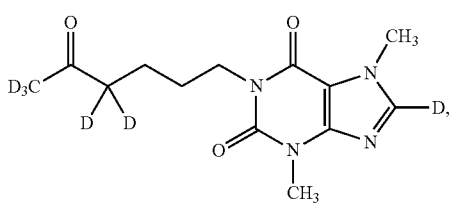
407
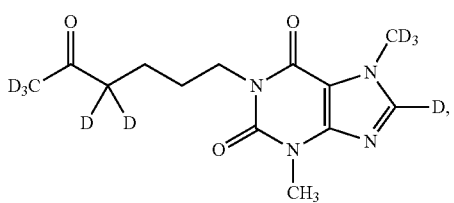
409
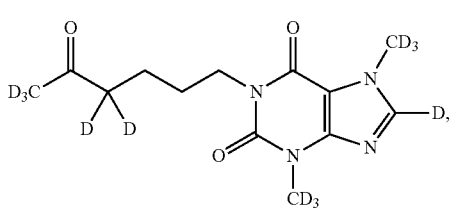
413
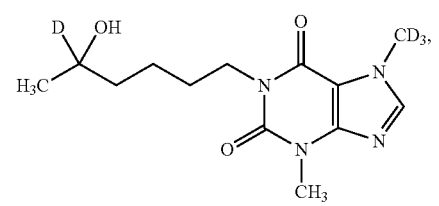
131
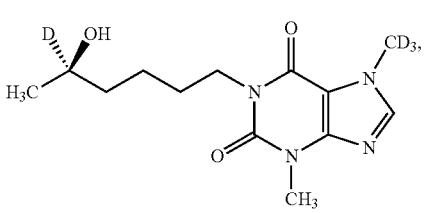
131 (R)
-continued
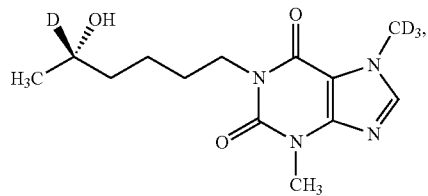
131 (S)
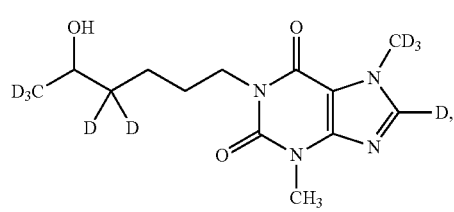
419
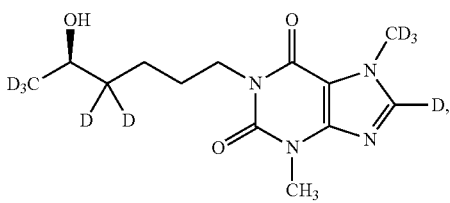
419 (R)
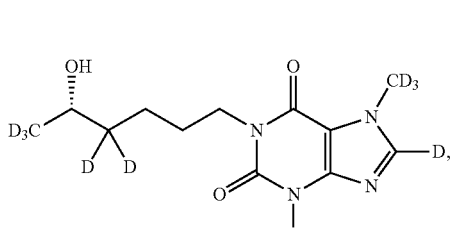
419 (S)
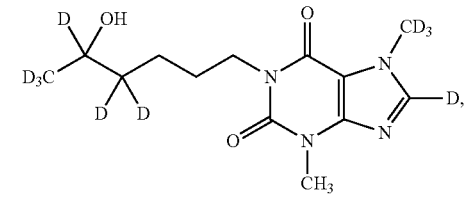
435
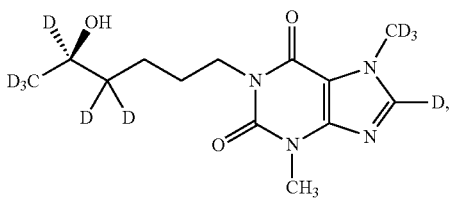
435 (R)
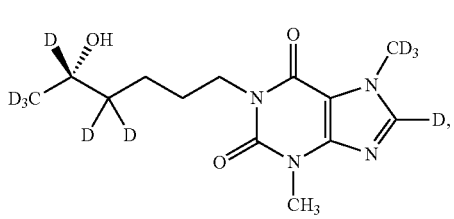
435 (S)

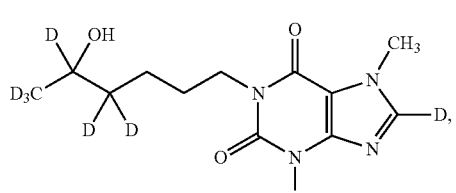

437

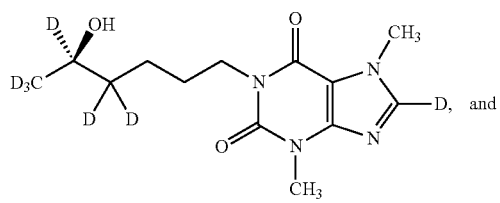

437 (R)

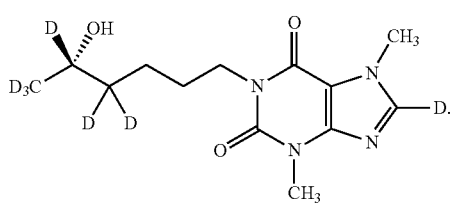

437 (S)

In another set of embodiments, any atom not designated as deuterium in any of the embodiments set forth above is present at its natural isotopic abundance.

The synthesis of compounds of this invention can be achieved by synthetic chemists of ordinary skill. Relevant procedures and intermediates are disclosed, for instance in Sidzhakova, D et al., Farmatsiya, (Sofia, Bulgaria) 1988, 38(4): 1-5; Davis, P J et al., Xenobiotica, 1985, 15(12): 1001-10; Akgun, H et al., J Pharm Sci, 2001, 26(2): 67-71; German Patent publication DD 274334; Czech Patent Nos. CS 237719, CS201558; PCT patent publication WO9531450; and in Japanese Patent publication Nos. JP58150594, JP58134092, JP58038284, JP57200391, JP57098284, JP57085387, JP57062278, JP57080385, JP57056481, JP57024385, JP57011981, JP57024386, JP57024382, JP56077279, JP56032477, JP56007785, JP56010188, JP56010187, JP55122779, and JP55076876.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Methods for synthesizing compounds of Formula I are depicted in the following schemes.

Scheme 1A. Synthesis of Compounds of Formula I

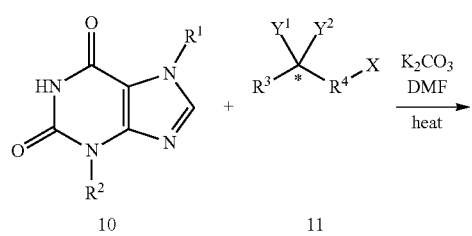

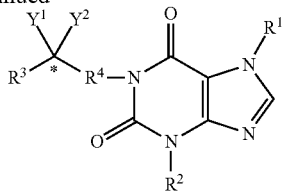

Formula I

As depicted in Scheme 1A, deuterated compound 10 is alkylated with deuterated intermediate 11 (wherein X is chloride, bromide or iodide) in the presence of potassium carbonate to afford compounds of Formula I. Alternatively, sodium hydroxide in aqueous methanol may be employed to afford compounds of Formula I according to the methods of U.S. Pat. No. 4,289,776.

Scheme 1B. Preparation of Compounds Where $Y^1$ = OH From Compounds of Formula II

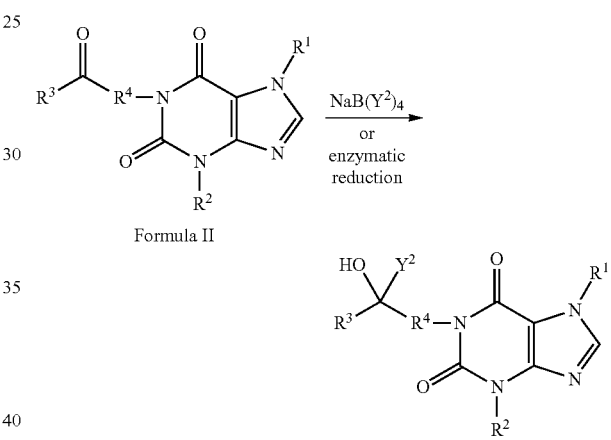

As depicted in Scheme 1B, compounds of Formula II can be used to make compounds where $Y^1$ is OH. Thus, compounds of Formula II are reduced with either sodium borohydride or sodium borodeuteride (commercially available at 99 atom % D) according to the general method of European Patent publication 0330031 to form compounds wherein $Y^1$ is OH and $Y^2$ is hydrogen or deuterium. The enantiomeric alcohol products may be separated, for example through the method of Nicklasson, M et al., Chirality, 2002, 14(8): 643-652. In an alternate method, enzymatic reduction affords an enantiomerically-enriched alcohol product using the methods disclosed in Pekala, E et al., Acta Poloniae Pharmaceutica, 2007, 64(2): 109-113, or in Pekala, E et al., Biotech J, 2007, 2(4): 492-496.

Synthesis of Compound 10

Referring to Scheme 1A, compounds that can be used as compound 10 to make compounds of Formula I are known and include, but are not limited to, the following: theobromine (wherein $R^1$ and $R^2$ are $CH_3$) which is commercially available. Isotopologues of 10 wherein: (a) $R^1$ is —$CD_3$ and $R^2$ is —$CH_3$; (b) $R^1$ is —$CH_3$ and $R^2$ is —$CD_3$; and (c) $R^1$ and $R^2$ are —$CD_3$ are all known. See Benchekroun, Y et al., J Chromatogr B, 1977, 688: 245; Ribon, B et al., Coll INSERM, 1988, 164: 268; and Horning, M G et al., Proc Int Conf Stable Isot 2nd, 1976, 41-54. 3-Methyl-7-propylxanthine, wherein $R^1$ is n-propyl and $R^2$ is —$CH_3$, is commercially available. Compound 10 wherein $R^1$ is $CH_2OCH_3$ and $R^2$ is $CH_3$ is also known. See German patent application DE 3942872A1.

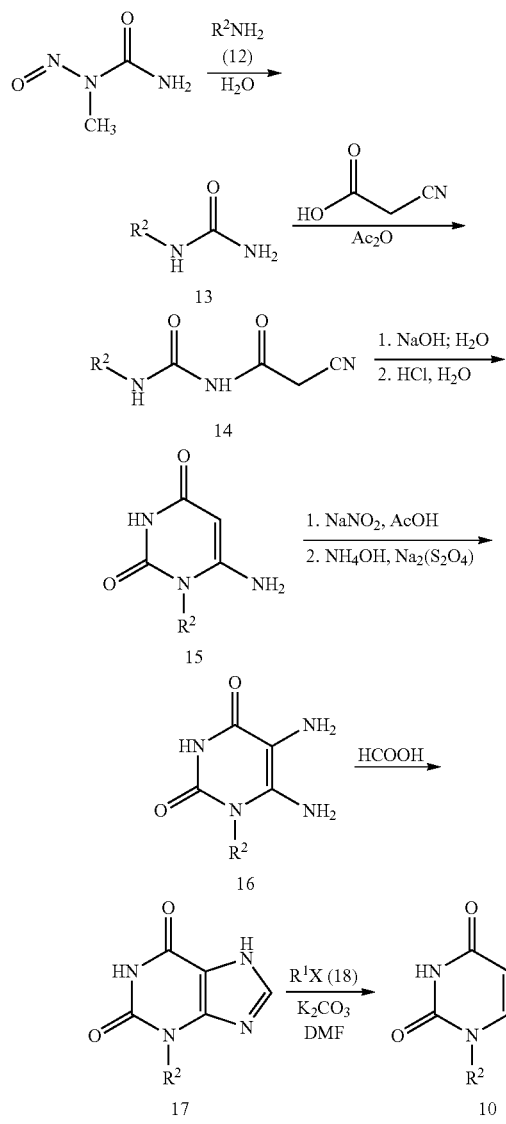

A synthesis of compound 10 is depicted in Scheme 2 starting with commercially-available N-nitroso-N-methylurea. Treatment with appropriately deuterated amine 12 in water affords N-alkylurea 13 following the methods of Boivin, J L et al., Canadian Journal of Chemistry, 1951, 29: 478-81. Urea 13 may be treated with 2-cyanoacetic acid and acetic anhydride to provide cyanoacetamide derivative 14, which is treated first with aqueous NaOH and then with aqueous HCl to provide cyclized pyrimidinedione 15 according to the methods of Dubey, P K et al., Indian Journal of Heterocyclic Chemistry, 2005, 14(4): 301-306. Alternatively, cyanoacetamide 14 may be treated with trimethylsilylchloride and hexamethyldisilazane to afford the cyclized product 15 via the methods of Fulle, F et al., Heterocycles, 2000, 53(2): 347-352.

Following the methods of Merlos, M et al., European Journal of Medicinal Chemistry, 1990, 25(8): 653-8, treatment of pyrimidinedione 15 with sodium nitrite in acetic acid, and then by ammonium hydroxide and sodium dithionite, yields compound 16, which is treated with formic acid to provide purine derivative 17. Following the methods disclosed by Rybar, A et al., in Czech patent application CS 26359581, alkylation of 17 with appropriately deuterated electrophile 18 (X is chloro, bromo, or iodo) in the presence of potassium carbonate and optionally in the presence of additives such as NaBr, KBr, NaI, KI, or iodine, affords compound 10.

Referring to Scheme 2, useful deuterated amine reagents 12 include, but are not limited to, commercially-available compounds such as n-propyl-$d_7$-amine, or known compounds such as 1-propan-1,1-$d_2$-amine (Moritz, F et al., Organic Mass Spectrometry, 1993, 28(3): 207-15). Useful deuterated urea reagents 13 may include, but are not limited to, commercially-available compounds such as N-methyl-$d_3$-urea

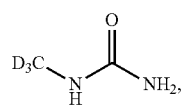

or methylurea-$d_6$

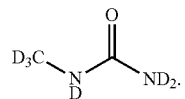

Useful deuterated electrophiles 18 may include, but are not limited to, commercially-available compounds such as iodomethane-$d_3$, or bromomethane-$d_3$, or 1-bromopropane-$d_7$, or 1-bromopropane-1,1-$d_2$, or known compounds such as (chloromethoxy-$d_2$)-ethane (Williams, A G, WO 2002059070A1), or bromomethoxymethane-$d_2$ (Van der Veken, B J et al., Journal of Raman Spectroscopy, 1992, 23(4): 205-23, or (bromomethoxy-$d_2$)-methane-$d_3$ (Van der Veken, B J et al., Journal of Raman Spectroscopy, 1992, 23(4): 205-23. The commercially available deuterated intermediates 12, 13 and 18 mentioned above are available having an isotopic purity of at least 98 atom % D.

Synthesis of Intermediate 11a-$d_5$ (cf. Scheme 1A)

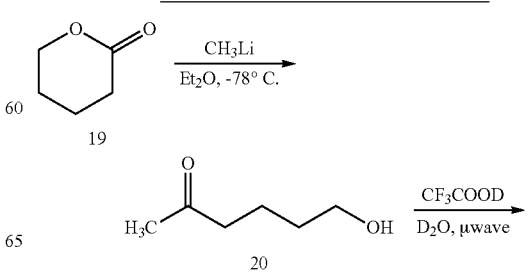

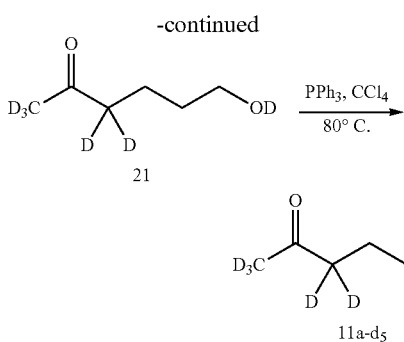

An approach to the preparation of compound 11a-d₅ (cf. Scheme 1A) (wherein $R^3$ is $CD_3$; $R^4$ is $^\dagger$-$CD_2(CH_2)_3$—, and $Y^1$ and $Y^2$ are taken together to form =O), is depicted in Scheme 3. Thus, methyllithium is added to commercially-available delta-valerolactone 19 according to the procedure of Zhang, Q et al., Tetrahedron, 2006, 62(50): 11627-11634 to afford ketone 20. Treatment of 20 with TFA-d₁ (99 atom % D) in D₂O (99 atom % D) under microwave conditions provides deuterated ketone 21 according to the general method of Fodor-Csorba K, Tet Lett, 2002, 43: 3789-3792. The alcohol moiety in 21 is converted to the chloride upon treatment with triphenylphosphine and carbon tetrachloride to yield chloride 11a-d₅ following the general procedures of Clément, J-L, Org Biomol Chem, 2003, 1: 1591-1597.

Scheme 4 depicts a synthesis of compound 11a-d₉ and compound 11a-d₁₁. Thus, commercially-available 4-phenylbutyric acid 22 may be heated in D₂O (99 atom % D) in the presence of Pd/C and hydrogen gas to afford deuterated acid 23 according to the general methods of Esaki, et al., Chem Eur J, 2007, 13: 4052-4063. Addition of deuterated methyllithium in the presence of trimethylsilyl chloride provides ketone 24, according to the general method of Porta, A et al., J Org Chem, 2005, 70(12): 4876-4878. Ketone 24 is converted to acetal 25 by treatment with D₂SO₄ (99 atom % D) and commercially-available ethyleneglycol-d₂ (99 atom % D). Treatment of 25 with NaIO₄ and RuCl₃ according to the general method of Gamier, J-M et al., Tetrahedron: Asymmetry, 2007, 18(12): 1434-1442 provides carboxylic acid 26. Reduction with either LiAlH₄ or LiAlD₄ (98 atom % D) provides the alcohols (not shown), which are then chlorinated using either phosphorus oxychloride or triphenylphosphine and N-chlorosuccinimide (Naidu, S V et al., Tet Lett, 2007, 48(13): 2279-2282), followed by acetal cleavage with D₂SO₄ (Heathcock, C H et al., J Org Chem, 1995, 60(5): 1120-30) to provides chlorides 11a-d₉ and 11a-d₁₁, respectively.

Scheme 4a. Synthesis of Intermediates 11b-(R)

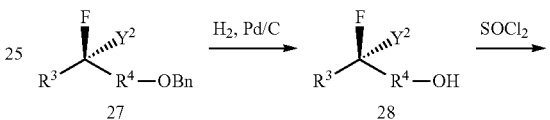

Scheme 4. Synthesis of Intermediates 11a-d₉ and 11a-d₁₁

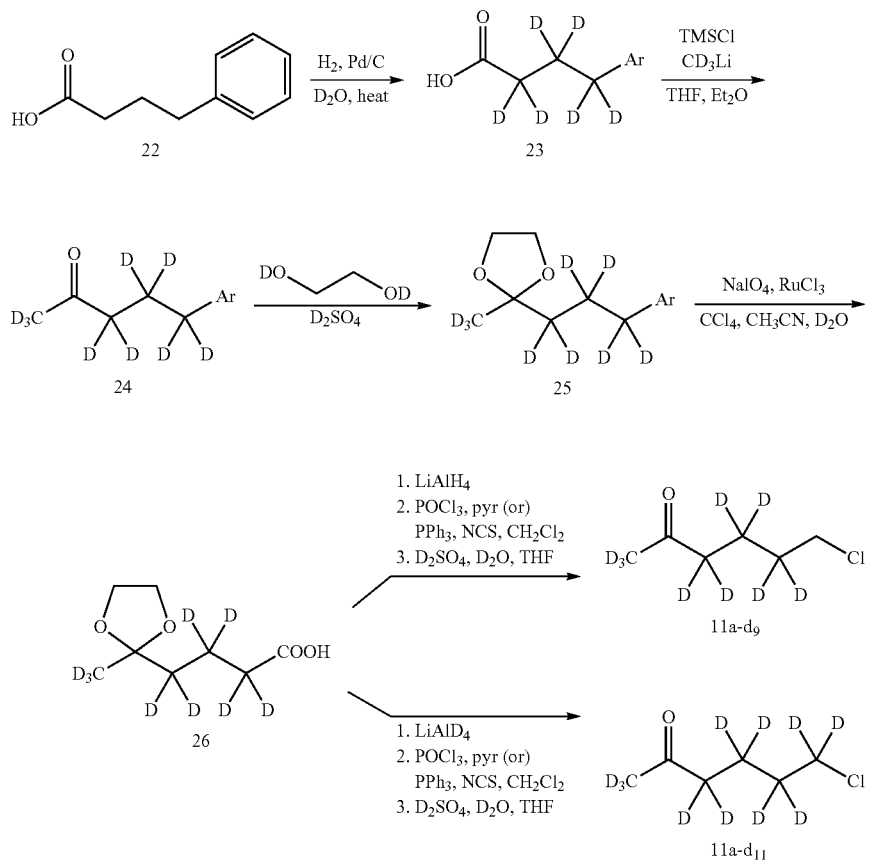

-continued

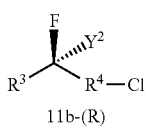

11b-(R)

Scheme 4b. Synthesis of Intermediates 11b-(S)

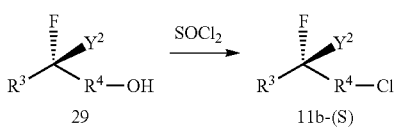

Schemes 4a and 4b depict the synthesis of specific enantiomers of chlorides 11b-(R) (wherein $Y^1$ is fluorine; $Y^2$ is selected from hydrogen and deuterium; and the compound is in the (R) configuration) and 11b-(S) (wherein $Y^1$ is fluorine; $Y^2$ is selected from hydrogen and deuterium; and the compound is in the (S) configuration). In Scheme 4a, a deuterated (or nondeuterated) benzyl-protected alcohol 27, such as known [[[(5R)-5-fluorohexyl]oxy]methyl]-benzene (PCT publication WO2000031003) is deprotected by hydrogenation in the presence of Pd/C to provide alcohol 28. The alcohol is chlorinated with thionyl chloride according to the general procedure of Lacan, G et al., J Label Compd Radiopharm, 2005, 48(9): 635-643 to afford chloride 11b-(R).

In Scheme 4b, a deuterated (or nondeuterated) alcohol 29, such as known (S)-(+)-5-fluorohexanol (Riswoko, A et al., Enantiomer, 2002, 7(1): 33-39) is chlorinated to afford chloride 11b-(S).

Scheme 5. Synthesis of Intermediates 11c and 11e

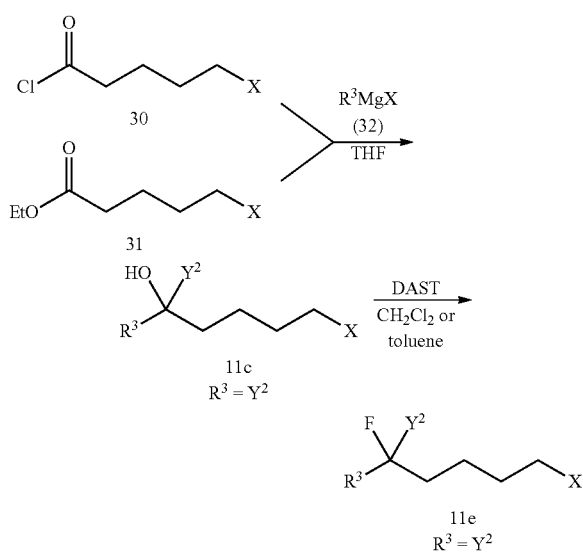

Scheme 5 depicts a synthesis of other intermediates 11c and 11e. Thus, following the methods of either Kutner, Andrzej et al., Journal of Organic Chemistry, 1988, 53(15): 3450-7, or of Larsen, S D et al., Journal of Medicinal Chemistry, 1994, 37(15): 2343-51, compounds 30 or 31 (wherein X is a halide) may be treated with deuterated Grignard reagent 32 to afford intermediate 11c wherein $R^3$ and $Y^2$ are the same, $Y^1$ is OH, and X is a halide. Treatment with diethylaminosulfur trifluoride (DAST) in dichloromethane or toluene provides intermediate 11e wherein $R^3$ and $Y^2$ are the same, $Y^1$ is F, and X is a halide according to the general procedures of either Karst, N A et al., Organic Letters, 2003, 5(25): 4839-4842, or of Kiso, M et al., Carbohydrate Research, 1988, 177: 51-67.

Commercially available halides can be used to make compounds 11 as disclosed in Scheme 5. For example, commercially-available 5-chlorovaleryl chloride, or commercially-available 5-bromovaleryl chloride, or commercially-available ethyl 5-bromovalerate, may be useful as reagents 30 or 31. Referring again to Scheme 5, use of commercially-available methyl-$d_3$-magnesium iodide as Grignard reagent 32 affords electrophile 11 wherein $R^3$ and $Y^2$ are simultaneously $CD_3$.

Scheme 6. Synthesis of Intermediate 11e (X = Br)

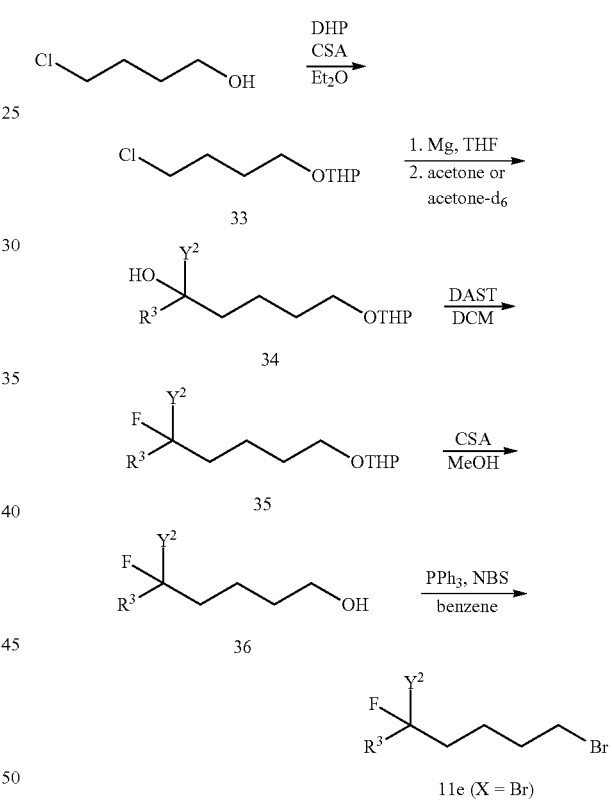

Scheme 6 depicts an alternate synthesis of intermediate 11e, wherein $R^3$ and $Y^2$ are the same and X=Br. Thus, according to the procedures of Hester, J B et al., Journal of Medicinal Chemistry, 2001, 44(7): 1099-1115, commercially-available 4-chloro-1-butanol is protected via treatment with 3,4-dihydro-2H-pyran (DHP) and camphorsulfonic acid (CSA) to provide chloride 33. Generation of the corresponding Grignard reagent with magnesium, followed by addition of acetone ($R^3=Y^2=CH_3$) or acetone-$d_6$ ($Y^2=R^3=CD_3$), affords alcohol 34. Fluorination with diethylaminosulfur trifluoride (DAST) in DCM provides fluoride 35. Deprotection with CSA in MeOH provides alcohol 36, and treatment with N-bromosuccinimide and triphenyl phosphine affords intermediate 11e.

Scheme 7. Alternative Synthesis of Intermediate 11e (X = Br)

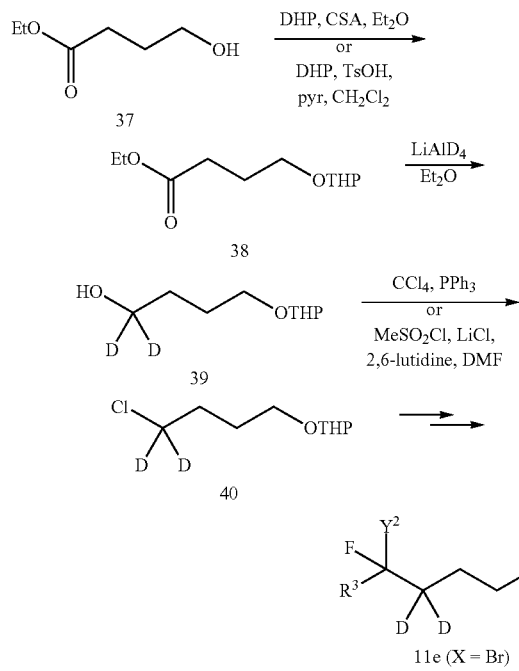

40

11e (X = Br)

Scheme 7 depicts the synthesis of intermediate 11e wherein $R^3$ and $Y^2$ are the same and X=Br. Thus, commercially-available 4-hydroxy-butanoic acid ethyl ester 37 is treated with DHP and CSA, or with DHP, TsOH, and pyridine to provide ester 38. Reduction with LiAlD$_4$ affords deuterated alcohol 39, which is treated with either triphenyl phosphine in CCl$_4$ (Sabitha, G et al., Tetrahedron Letters, 2006, (volume date 2007), 48(2): 313-315) or with methanesulfonyl chloride, lithium chloride, and 2,6-lutidine in DMF (Blaszykowski, C et al., Organic Letters, 2004, 6(21): 3771-3774) to afford chloride 40. Following the same methods as in Scheme 6, chloride 40 may be converted to 11e.

Scheme 8. Synthesis of Intermediate 11e-d$_8$ (X = Br)

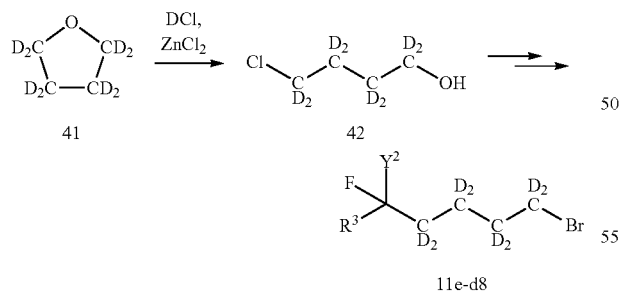

11e-d8

Scheme 8 depicts the synthesis of intermediate 11e-d$_8$ wherein $R^3$ and $Y^2$ are the same and X=Br. Thus, commercially-available THF-d$_8$ 41 may be treated with DCl and ZnCl$_2$ according to the general methods of Yang, A et al., Huagong Shikan, 2002, 16(3): 37-39 to afford known chloride 42 (Alken, Rudolf-Giesbert, WO 2003080598A1). Following the same methods as in Scheme 6, chloride 42 may be converted to 11e-d$_8$.

Scheme 9. Synthesis of Intermediate 11c-d$_8$ (X = Br)

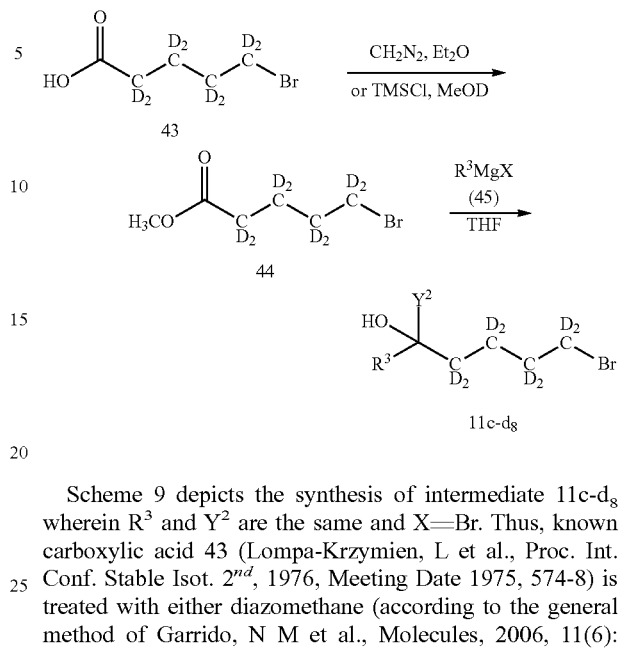

11c-d8

Scheme 9 depicts the synthesis of intermediate 11c-d$_8$ wherein $R^3$ and $Y^2$ are the same and X=Br. Thus, known carboxylic acid 43 (Lompa-Krzymien, L et al., Proc. Int. Conf. Stable Isot. $2^{nd}$, 1976, Meeting Date 1975, 574-8) is treated with either diazomethane (according to the general method of Garrido, N M et al., Molecules, 2006, 11(6): 435-443.) or with trimethylsilyl chloride and methanol-d$_1$ (according to the general method of Doussineau, T et al., Synlett, 2004, (10): 1735-1738) to provide methyl ester 44. As in Scheme 5, treatment of the ester with deuterated Grignard reagent 45 affords intermediate 11c-d$_8$. For example, use of commercially-available methyl-d$_3$-magnesium iodide as Grignard reagent 45 affords 11c-d$_8$ wherein $R^3$ and $Y^2$ are simultaneously CD$_3$.

Scheme 10. Synthesis of Intermediate 11c-d$_2$.

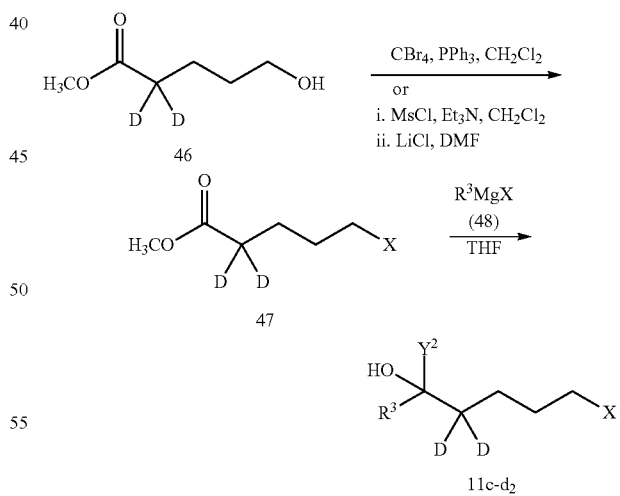

11c-d2

Scheme 10 depicts a preparation of 11c-d$_2$, wherein $R^3$ and $Y^2$ are the same. Thus, known deuterated ester 46 (Feldman, K S et al., Journal of Organic Chemistry, 2000, 65(25): 8659-8668) is treated with carbon tetrabromide and triphenylphosphine (Brueckner, A M et al., European Journal of Organic Chemistry, 2003, (18): 3555-3561) to afford ester 47 wherein X is bromide, or is treated with methanesulfonyl chloride and triethylamine, followed by lithium chloride and DMF (Sagi, K et al., Bioorganic & Medicinal Chemistry, 2005, 13(5): 1487-1496) to afford ester 47 wherein X is chloride. As in Scheme 5, treatment of ester 47 with deuterated Grignard reagent 48 affords 11c-d$_2$. For example, use of commercially-available methyl-d$_3$-magnesium iodide as Grignard reagent 48 affords 11c-d$_2$ wherein R$^3$ and Y$^2$ are simultaneously CD$_3$.

Additional known chlorides that may be utilized as reagent 11 in Scheme 1A include:
1-chloro-5,5-difluoro-hexane (Rybczynski, P J et al., J Med Chemistry, 2004, 47(1): 196-209); 1-chloro-5-fluorohexane (Chambers, R D et al., Tetrahedron, 2006, 62(30): 7162-7167); 6-chloro-2-hexanol (European Patent publication 0412596); (S)-6-chloro-2-hexanol (Keinan, E et al., J Am Chem Soc, 1986, 108(12): 3474-3480); commercially-available (R)-6-chloro-2-hexanol; commercially available 6-chloro-2-hexanone; known 6-chloro-2-methylhexan-2-ol (Kutner, A et al., Journal of Organic Chemistry, 1988, 53(15): 3450-7); known 6-bromo-2-methylhexan-2-ol (Kutner, A et al., Journal of Organic Chemistry, 1988, 53(15): 3450-7); known 1-bromo-5-fluoro-5-methylhexane (Hester, J B et al., Journal of Medicinal Chemistry, 2001, 44(7): 1099-1115).

Scheme 11. Synthesis of Compound of Formula A1

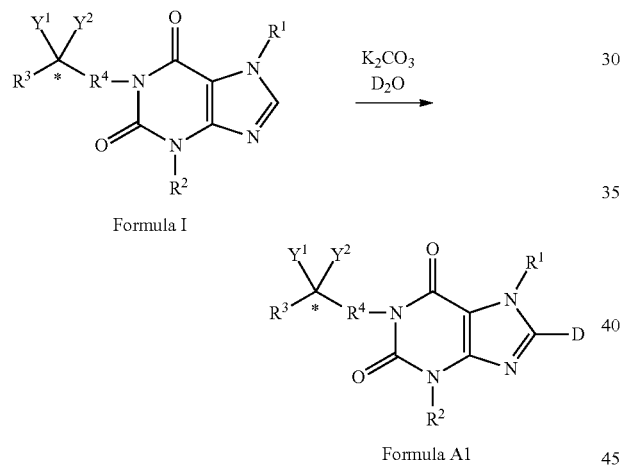

Scheme 11 depicts the synthesis of a compound of Formula A1. Thus, a compound of Formula I is treated with potassium carbonate in D$_2$O to effect a hydrogen-to-deuterium exchange reaction, providing a compound of Formula A1. One skilled in the art will appreciate that additional hydrogen-to-deuterium exchange reactions may also occur elsewhere in the molecule.

Scheme 12. Alternative Synthesis of Compounds of Formula A1

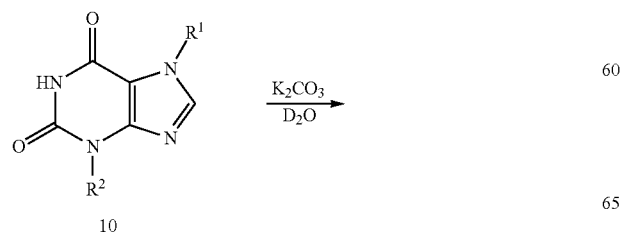

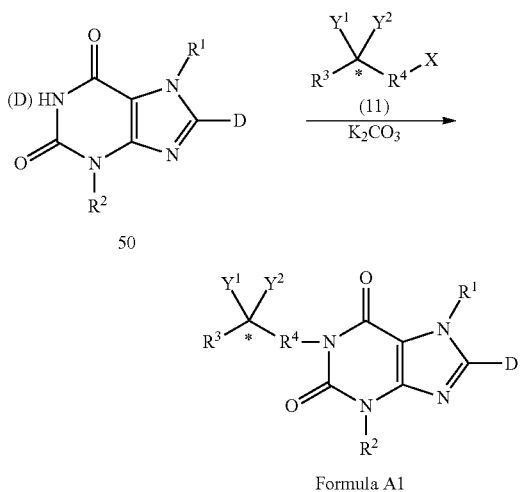

An alternative synthesis of a compound of Formula A1 is depicted in Scheme 12. Thus, intermediate 10 (cf. Scheme 1A) is treated with potassium carbonate in D$_2$O to effect a hydrogen-to-deuterium exchange reaction, providing compound 50 as either the N-D or N—H species. Alkylation with intermediate 11 in the presence of potassium carbonate affords compounds of Formula A1.

A number of novel intermediates can be used to prepare compounds of Formula A. Thus, the invention also provides such a compound which is selected from the following:

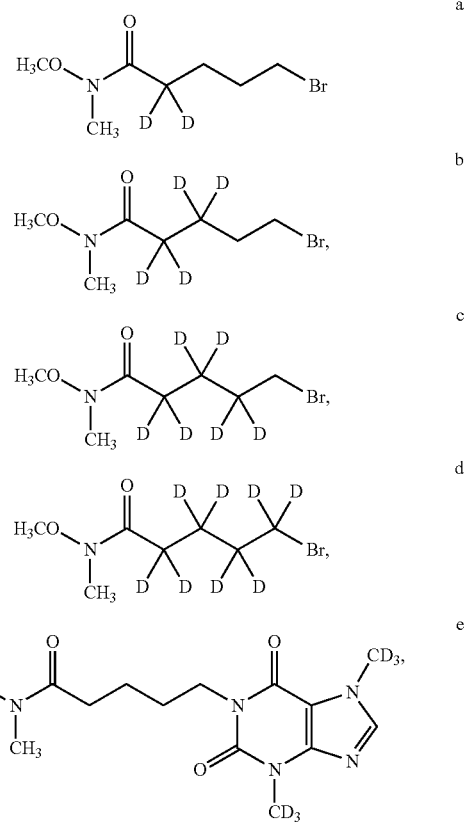

f
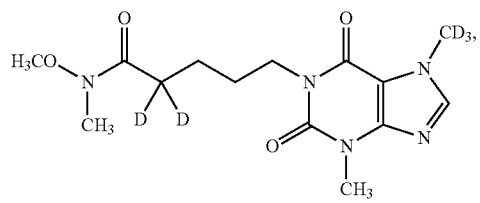

g
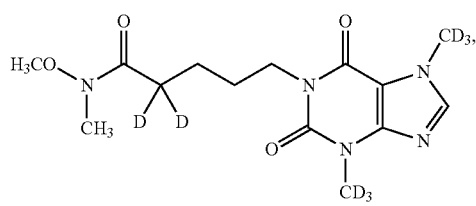

h
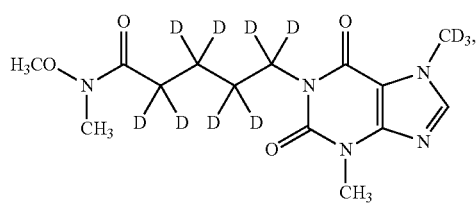

i
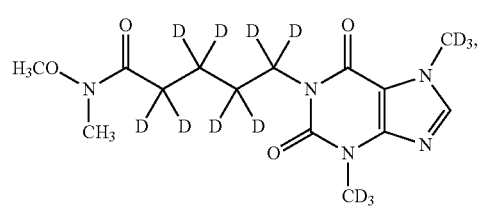

j
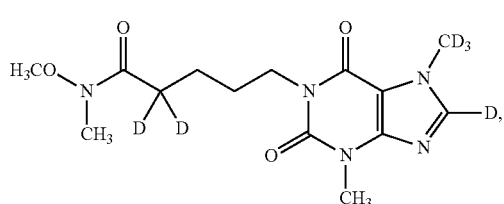

k
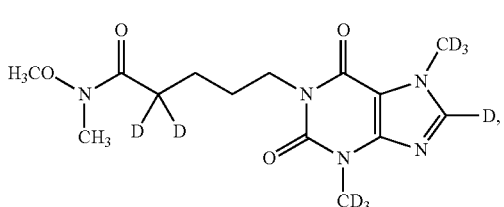

l
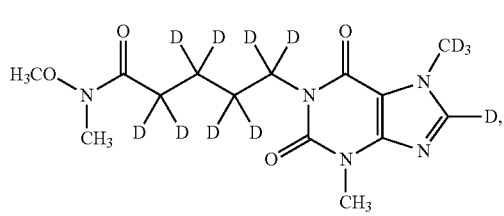

m
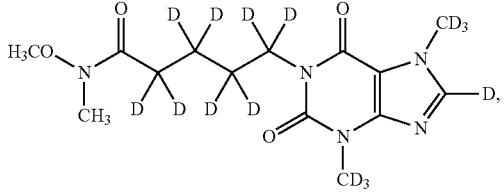

n
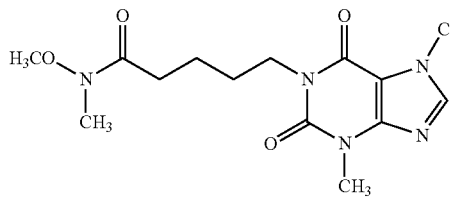

o
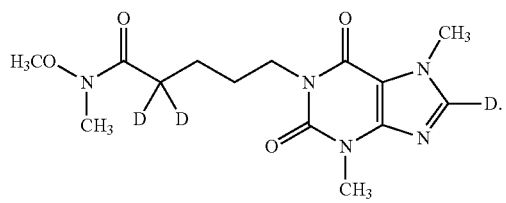

Compounds a-d above may be prepared as generally described in Org. Lett., 2005, 7: 1427-1429 using appropriately-deuterated starting materials. Compounds e-o may be prepared from the appropriate bromides listed above by reference to Scheme 15 shown below.

Certain xanthine intermediates useful for this invention are also novel. Thus, the invention provides a deuterated xanthine intermediate III:

III

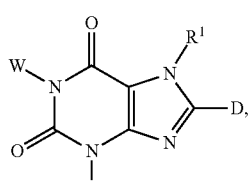

where W is hydrogen or deuterium, and each of $R^1$ and $R^2$ is independently selected from hydrogen, deuterium, $C_{1-3}$ alkyl optionally substituted with deuterium, and $C_{1-3}$ alkoxyalkyl optionally substituted with deuterium. Examples of $R^1$ and $R^2$ $C_{1-3}$ alkyl include —$CH_3$, —$CD_3$, —$CH_2CH_2CH_3$, and —$CD_2CD_2CD_3$. Examples of $C_{1-3}$ alkoxyalkyl include —$CH_2OCH_2CH_3$, —$CD_2OCH_2CH_3$, —$CD_2OCD_2CH_3$, and —$CD_2OCD_2CD_3$.

Specific examples of formula III include the following:

III-a

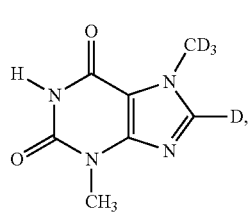

-continued

III-b 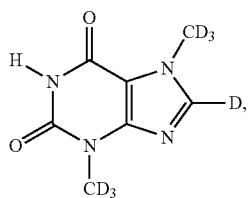

III-c 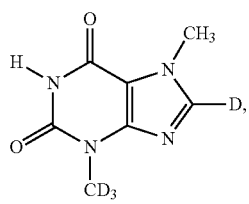

III-d 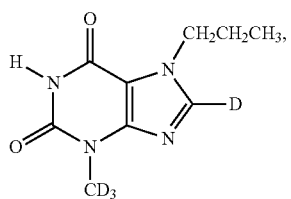

III-e 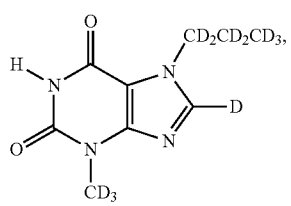

III-f 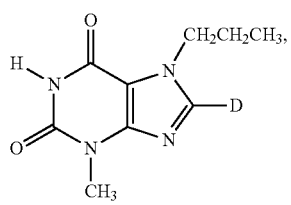

III-g 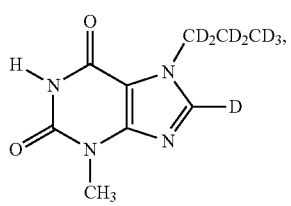

III-h 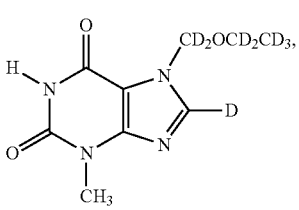

-continued

III-i 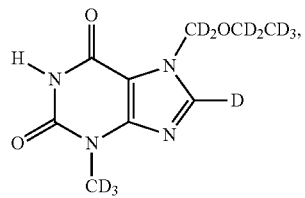

III-j 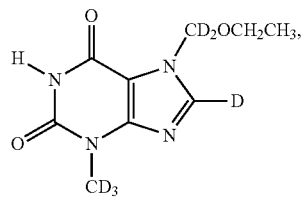

III-k 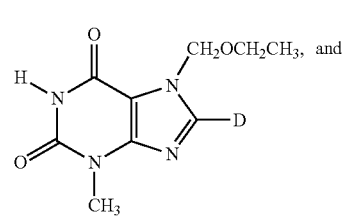

III-l 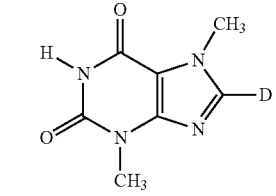

In each of the above examples of formula III, W is hydrogen. In a set of corresponding examples, W is deuterium. Salts of compounds of Formula III are also useful, including salts that are known to be useful with respect to known xanthines. Examples of useful salts include, but are not limited to, the lithium salt, sodium salt, potassium salt, and cesium salt. An example of a particularly useful salt is the potassium salt.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of this invention and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3rd Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of this invention or pharmaceutically acceptable salts thereof; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and *acacia* or tragacanth; and pastilles comprising the active ingredient in an inert basis such as gelatin and glycerin, or sucrose and *acacia*.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz, J D and Zaffaroni, A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as pentoxifylline. Such agents include those indicated as being useful in combination with pentoxifylline, including but not limited to, those described in WO 1997019686, EP 0640342, WO 2003013568, WO 2001032156, WO 2006035418, and WO 1996005838.

Preferably, the second therapeutic agent is an agent useful in the treatment or prevention of a disease or condition selected from peripheral obstructive vascular disease; glomerulonephritis; nephrotic syndrome; nonalcoholic steatohepatitis; Leishmaniasis; cirrhosis; liver failure; Duchenne's muscular dystrophy; late radiation induced injuries; radiation induced lymphedema; radiation-associated necrosis; alcoholic hepatitis; radiation-associated fibrosis; necrotizing enterocolitis in premature neonates; diabetic nephropathy, hypertension-induced renal failure, and other chronic kidney disease; Focal Segmental Glomerulosclerosis; pulmonary sarcoidosis; recurrent aphthous stomatitis; chronic breast pain in breast cancer patients; brain and central nervous system tumors; malnutrition-inflammation-cachexia syndrome; interleukin-1 mediated disease; graft versus host reaction and other allograft reactions; diet-induced fatty liver conditions, atheromatous lesions, fatty liver degeneration and other diet-induced high fat or alcohol-induced tissue-degenerative conditions; human immunodeficiency virus type 1 (HIV-1) and other human retroviral infections; multiple sclerosis; cancer; fibroproliferative diseases; fungal infection; drug-induced nephrotoxicity; collagenous colitis and other diseases and/or conditions characterized by elevated levels of platelet derived growth factor (PDGF) or other inflammatory cytokines; endometriosis; optic neuropathy and CNS impairments associated with acquired immunodeficiency syndrome (AIDS), immune disorder diseases, or multiple sclerosis; autoimmune disease; upper respiratory viral infection; depression; urinary incontinence; irritable bowel syndrome; septic shock; Alzheimers Dementia; neuropathic pain; dysuria; retinal or optic nerve damage; peptic ulcer; insulin-dependent diabetes; non-insulin-dependent diabetes; diabetic nephropathy; metabolic syndrome; obesity; insulin resistance; dyslipidemia; pathological glucose tolerance; hypertension; hyperlipidemia; hyperuricemia; gout; hypercoagulability; and inflammation or injury associated with neutrophil chemotaxis and/or degranulation. The compounds of this invention can also be used to control intraocular pressure or to stabilize auto-regulation of cerebral blood flow in subjects who require such control as determined by medical examination.

In one embodiment, the second therapeutic agent is selected from α-tocopherol and hydroxyurea.

In another embodiment, the second therapeutic agent is useful in the treatment of diabetes or an associated disorder, and is selected from insulin or insulin analogues, glucagon-like-peptide-1 (GLP-1) receptor agonists, sulfonylurea agents, biguanide agents, alpha-glucosidase inhibitors, PPAR agonists, meglitinide agents, dipeptidyl-peptidase (DPP) IV inhibitors, other phosphodiesterase (PDE1, PDE5, PDE9, PDE10 or PDE1) inhibitors, amylin agonists, CoEnzyme A inhibitors, and antiobesity agents.

Specific examples of insulin include, but are not limited to Humulin® (human insulin, rDNA origin), Novolin® (human insulin, rDNA origin), Velosulin® BR (human buffered regular insulin, rDNA origin), Exubera® (human insulin, inhaled), and other forms of inhaled insulin, for instance, as delivered by Mannkind's "Technosphere Insulin System".

Specific examples of insulin analogues include, but are not limited to, novarapid, insulin detemir, insulin lispro, insulin glargine, insulin zinc suspension and Lys-Pro insulin.

Specific examples of Glucagon-Like-Peptide-1 receptor agonists include, but are not limited to BIM-51077 (CAS-No. 275371-94-3), EXENATIDE (CAS-No. 141758-74-9), CJC-1131 (CAS-No. 532951-64-7), LIRAGLUTIDE (CAS-No. 20656-20-2) and ZP-10 (CAS-No. 320367-13-3).

Specific examples of sulfonylurea agents include, but are not limited to, TOLBUTAMIDE (CAS-No. 000064-77-7), TOLAZAMIDE (CAS-No. 001156-19-0), GLIPIZIDE (CAS-No. 029094-61-9), CARBUTAMIDE (CAS-No. 000339-43-5), GLISOXEPIDE (CAS-No. 025046-79-1), GLISENTIDE (CAS-No. 032797-92-5), GLIBORNURIDE (CAS-No. 026944-48-9), GLIBENCLAMIDE (CAS-NO. 010238-21-8), GLIQUIDONE (CAS-No. 033342-05-1), GLIMEPIRIDE (CAS-No. 093479-97-1) and GLICLAZIDE (CAS-No. 021187-98-4).

A specific example of a biguanide agent includes, but is not limited to METFORMIN (CAS-No. 000657-24-9).

Specific examples of alpha-glucosidase-inhibitors include, but are not limited to ACARBOSE (Cas-No. 056180-94-0), MIGLITOL (CAS-No. 072432-03-2) and VOGLIBOSE (CAS-No. 083480-29-9).

Specific examples of PPAR-agonists include, but are not limited to MURAGLITAZAR (CAS-No. 331741-94-7), ROSIGLITAZONE (CAS-NO. 122320-73-4), PIOGLITAZONE (CAS-No. 111025-46-8), RAGAGLITAZAR (CAS-NO. 222834-30-2), FARGLITAZAR (CAS-No. 196808-45-4), TESAGLITAZAR (CAS-No. 251565-85-2), NAVEGLITAZAR (CAS-No. 476436-68-7), NETOGLITAZONE (CAS-NO. 161600-01-7), RIVOGLITAZONE (CAS-NO. 185428-18-6), K-1 11 (CAS-No. 221564-97-2), GW-677954 (CAS-No. 622402-24-8), FK-614 (CAS-No 193012-35-0) and (−)-Halofenate (CAS-No. 024136-23-0). Preferred PPAR-agonists are ROSGLITAZONE and PIOGLITAZONE.

Specific examples of meglitinide agents include, but are not limited to REPAGLINIDE (CAS-No. 135062-02-1), NATEGLINIDE (CAS-No. 105816-04-4) and MITIGLINIDE (CAS-No. 145375-43-5).

Specific examples of DPP IV inhibitors include, but are not limited to SITAGLIPTIN (CAS-No. 486460-32-6), SAXAGLIPTIN (CAS-No. 361442-04-8), VILDAGLIPTIN (CAS-No. 274901-16-5), DENAGLIPTIN (CAS-No. 483369-58-0), P32/98 (CAS-No. 251572-70-0) and NVP-DPP-728 (CAS-No. 247016-69-9).

Specific examples of PDE5 inhibitors include, but are not limited to SILDENAFIL (CAS-No. 139755-83-2), VARDENAFIL (CAS-No. 224785-90-4) and TADALAFIL (CAS-No. 171596-29-5). Examples of PDE1, PDE9, PDE10 or PDE11 inhibitors which may be usefully employed according to the present invention can be found, for example, in US20020160939, WO2003037432, US2004220186, WO2005/003129, WO2005012485, WO2005120514 and WO03077949.

A specific example of an amylin agonist includes, but is not limited to PRAMLINITIDE (CAS-No. 151126-32-8).

A specific example of a Coenzyme A inhibitor includes, but is not limited to ETOMOXIR (CAS-No. 082258-36-4).

Specific examples of anti-obesity drugs include, but are not limited to HMR-1426 (CAS-No. 262376-75-0), CETILISTAT (CAS-No. 282526-98-1) and SIBUTRAMINE (CAS-No. 106650-56-0).

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder. For example, and effective amount is sufficient to reduce or ameliorate the severity, duration or progression of the disorder being treated, prevent the advancement of the disorder being treated, cause the regression of the disorder being treated, or enhance or improve the therapeutic effect(s) of another therapy.

The interrelationship of dosages for animals and humans (based on milligrams per meter squared of body surface) is described in Freireich et al., Cancer Chemother. Rep, 1966, 50: 219. Body surface area may be determined approximately from height and weight of the patient. See, e.g., Scientific Tables, Geigy Pharmaceuticals, Ardsley, N.Y., 1970, 537.

In one embodiment, an effective amount of a compound of this invention is in the range of 20 mg to 2000 mg per treatment. In more specific embodiments the amount is in the range of 40 mg to 1000 mg, or in the range of 100 mg to 800 mg, or more specifically in the range of 200 mg to 400 mg per treatment. Treatment typically is administered from one to three times daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for pentoxifylline.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In one embodiment, the invention provides a method of inhibiting the activity of phosphodiesterase (PDE) in a cell, comprising contacting a cell with one or more compounds of Formula A, A1, I, II or B.

In addition to its PDE inhibitory activity, pentoxifylline is known to suppress the production of a number of other biological agents such as interleukin-1 (IL-1), IL-6, IL-12, TNF-alpha, fibrinogen, and various growth factors. Accordingly, in another embodiment, the invention provides a method of suppressing the production of interleukin-1 (IL-1), IL-6, IL-12, TNF-alpha, fibrinogen, and various growth factors in a cell, comprising contacting a cell with one or more compounds of Formula A, A1, I, II or B.

According to another embodiment, the invention provides a method of treating a disease in a patient in need thereof that is beneficially treated by pentoxifylline comprising the step of administering to said patient an effective amount of a compound of Formula A, A1, I, II or B or a pharmaceutical composition comprising a compound of Formula A, A1, I, II or B and a pharmaceutically acceptable carrier.

Such diseases are well known in the art and are disclosed in, but not limited to the following patents and published applications: WO 1988004928, EP 0493682, U.S. Pat. No. 5,112,827, EP 0484785, WO 1997019686, WO 2003013568, WO 2001032156, WO 1992007566, WO 1998055110, WO 2005023193, U.S. Pat. No. 4,975,432, WO 1993018770, EP 0490181, and WO 1996005836. Such diseases include, but are not limited to, peripheral obstructive vascular disease; glomerulonephritis; nephrotic syndrome; nonalcoholic steatohepatitis; Leishmaniasis; cirrhosis; liver failure; Duchenne's muscular dystrophy; late radiation induced injuries; radiation induced lymphedema; radiation-associated necrosis; alcoholic hepatitis; radiation-associated fibrosis; necrotizing enterocolitis in premature neonates; diabetic nephropathy, hypertension-induced renal failure, and other chronic kidney disease; Focal Segmental Glomerulosclerosis; pulmonary sarcoidosis; recurrent aphthous stomatitis; chronic breast pain in breast cancer patients; brain and central nervous system tumors; malnutrition-inflammation-cachexia syndrome; interleukin-1 mediated disease; graft versus host reaction and other allograft reactions; diet-induced fatty liver conditions, atheromatous lesions, fatty liver degeneration and other diet-induced high fat or alcohol-induced tissue-degenerative conditions; human immunodeficiency virus type 1 (HIV-1) and other human retroviral infections; multiple sclerosis; cancer; fibroproliferative diseases; fungal infection; drug-induced nephrotoxicity; collagenous colitis and other diseases and/or conditions characterized by elevated levels of platelet derived growth factor (PDGF) or other inflammatory cytokines; endometriosis; optic neuropathy and CNS impairments associated with acquired immunodeficiency syndrome (AIDS), immune disorder diseases, or multiple sclerosis; autoimmune disease; upper respiratory viral infection; depression; urinary incontinence; irritable bowel syndrome; septic shock; Alzheimers Dementia; neuropathic pain; dysuria; retinal or optic nerve damage; peptic ulcer; insulin-dependent diabetes; non-insulin-dependent diabetes; diabetic nephropathy; metabolic syndrome; obesity; insulin resistance; dyslipidemia; pathological glucose tolerance; hypertension; hyperlipidemia; hyperuricemia; gout; hypercoagulability; acute alcoholic hepatitis; olfaction disorders; patent ductus arteriosus; and inflammation or injury associated with neutrophil chemotaxis and/or degranulation.

The compounds of Formula A, A1, I, II or B can also be used to control intraocular pressure or to stabilize autoregulation of cerebral blood flow in subjects who require such control as determined by medical examination.

In one particular embodiment, the method of this invention is used to treat a disease or condition in a patient in need thereof selected from intermittent claudication on the basis of chronic occlusive arterial disease of the limbs and other peripheral obstructive vascular diseases; glomerulonephritis; Focal Segmental Glomerulosclerosis; nephrotic syndrome; nonalcoholic steatohepatitis; Leishmaniasis; cirrhosis; liver failure; Duchenne's muscular dystrophy; late radiation induced injuries; radiation induced lymphedema; alcoholic hepatitis; radiation-induced fibrosis; necrotizing enterocolitis in premature neonates; diabetic nephropathy, hypertension-induced renal failure and other chronic kidney diseases; pulmonary sarcoidosis; recurrent aphthous stomatitis; chronic breast pain in breast cancer patients; brain and central nervous system tumors; obesity; acute alcoholic hepatitis; olfaction disorders; endometriosis-associated infertility; malnutrition-inflammation-cachexia syndrome; and patent ductus arteriosus.

In one embodiment, the method of this invention is used to treat diabetic nephropathy, hypertensive nephropathy or intermittent claudication on the basis of chronic occlusive arterial disease of the limbs. In another particular embodiment, the method of this invention is used to treat a disease or condition in a patient in need thereof selected from intermittent claudication on the basis of chronic occlusive arterial disease of the limbs.

In one embodiment, the method of this invention is used to treat chronic kidney disease. The chronic kidney disease may be selected from glomerulonephritis, focal segmental glomerulosclerosis, nephrotic syndrome, reflux uropathy, or polycystic kidney disease.

In one embodiment, the method of this invention is used to treat chronic disease of the liver. The chronic disease of the liver may be selected from nonalcoholic steatohepatitis, fatty liver degeneration or other diet-induced high fat or alcohol-induced tissue-degenerative conditions, cirrhosis, liver failure, or alcoholic hepatitis.

In one embodiment, the method of this invention is used to a diabetes-related disease or condition. This disease may be selected from insulin resistance, retinopathy, diabetic ulcers, radiation-associated necrosis, acute kidney failure or drug-induced nephrotoxicity.

In one embodiment, the method of this invention is used to treat a patient suffering from cystic fibrosis, including those patients suffering from chronic *Pseudomonas* bronchitis.

In one embodiment, the method of this invention is used to aid in wound healing. Examples of types of wounds that may be treated include venous ulcers, diabetic ulcers and pressure ulcers.

In another particular embodiment, the method of this invention is used to treat a disease or condition in a patient in need thereof selected from insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient one or more second therapeutic agents. The choice of second therapeutic agent may be made from any second therapeutic agent known to be useful for co-administration with pentoxifylline. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula A, A1, I, II or B and a second therapeutic agent for treatment of the following conditions (with the particular second therapeutic agent indicated in parentheses following the indication): late radiation induced injuries (α-tocopherol), radiation-induced fibrosis (α-tocopherol), radiation induced lymphedema (α-tocopherol), chronic breast pain in breast cancer patients (α-tocopherol), type 2 diabetic nephropathy (captopril), malnutrition-inflammation-cachexia syndrome (oral nutritional supplement, such as Nepro; and oral anti-inflammatory module, such as Oxepa); and brain and central nervous system tumors (radiation therapy and hydroxyurea).

The combination therapies of this invention also include co-administering a compound of Formula A, A1, I, II or B and a second therapeutic agent for treatment of insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula A, A1, I, II or B alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula A, A1, I, II or B for use in the treatment or prevention in a patient of a disease, disorder or symptom thereof delineated herein.

Diagnostic Methods and Kits

The present invention also provides kits for use to treat peripheral obstructive vascular disease, in particular intermittent claudication on the basis of chronic occlusive arterial disease of the limbs; glomerulonephritis; nephrotic syndrome; nonalcoholic steatohepatitis; Leishmaniasis; cirrhosis; liver failure; Duchenne's muscular dystrophy; late radiation induced injuries; radiation induced lymphedema; alcoholic hepatitis; radiation fibrosis; necrotizing enterocolitis in premature neonates; chronic kidney disease; pulmonary sarcoidosis; recurrent aphthous stomatitis; chronic breast pain in breast cancer patients; brain and central nervous system tumors; malnutrition-inflammation-cachexia syndrome; insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability. These kits comprise (a) a pharmaceutical composition comprising a compound of Formula A, A1, I, II or B or a salt thereof, wherein said pharmaceutical composition is in a container; and (b) instructions describing a method of using the pharmaceutical composition to treat peripheral obstructive vascular disease, in particular intermittent claudication on the basis of chronic occlusive arterial disease of the limbs; glomerulonephritis; nephrotic syndrome; nonalcoholic steatohepatitis; Leishmaniasis; cirrhosis; liver failure; Duchenne's muscular dystrophy; late radiation induced injuries; radiation induced lymphedema; alcoholic hepatitis; radiation fibrosis; necrotizing enterocolitis in premature neonates; chronic kidney disease; pulmonary sarcoidosis; recurrent aphthous stomatitis; chronic breast pain in breast cancer patients; brain and central nervous system tumors; malnutrition-inflammation-cachexia syndrome; insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

SYNTHETIC EXAMPLES

The synthetic examples below provide detailed procedures for making certain compounds of this invention. It will be apparent to one skilled in the art that further compounds of this invention may be prepared through the use of other reagents or intermediates by reference to these procedures and the schemes described above. The prepared compounds were analyzed by NMR, mass spectrometry, and/or elemental analysis as indicated. ¹HNMR were taken on a 300 MHz instrument, which was useful for determining deuterium incorporation. Unless otherwise stated, the absence of an NMR signal as noted in the examples below indicates a level of deuterium incorporation that is at least 90%.

Example 1

Synthesis of 3-Methyl-7-(methyl-d₃)-1-(5-oxohexyl)-1H-purine-2,6(3H,7H)-dione (Compound 100)

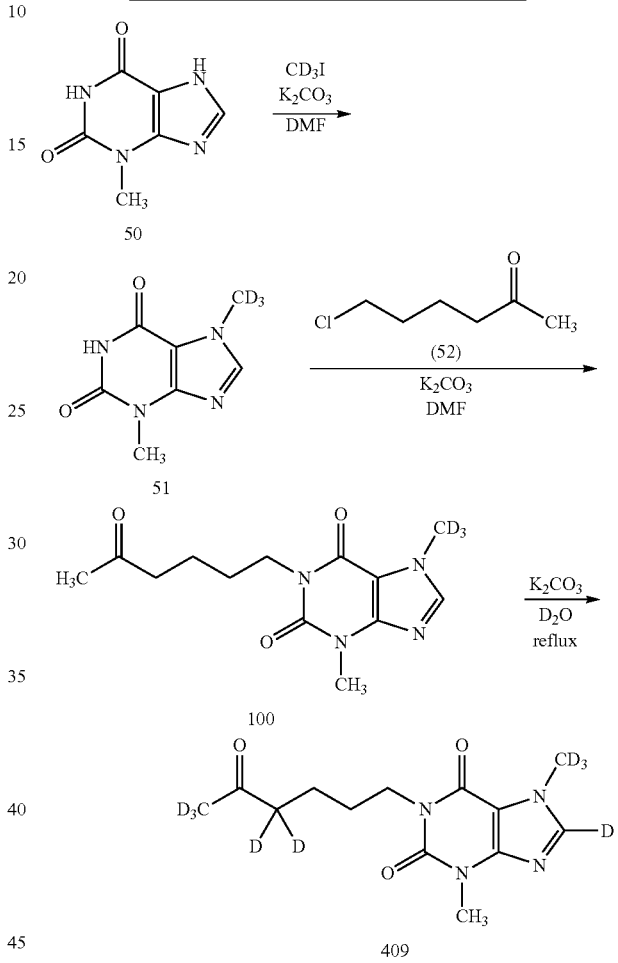

Step 1. 3-Methyl-7-(methyl-d₃)-1H-purine-2,6(3H,7H)-dione (51)

A suspension of 3-methylxanthine 50 (5.0 g, 30.1 mmol, 1 equiv) and powdered K₂CO₃ (5.0 g, 36.0 mmol, 1.2 equiv) in DMF (95 mL) was heated to 60° C. and iodomethane-d₃ (Cambridge Isotopes, 99.5 atom % D, 2.2 mL, 36.0 mmol, 1.2 equiv) was added via syringe. The resulting mixture was heated at 80° C. for 5 hours (h). The reaction mixture was cooled to room temperature (rt) and the DMF was evaporated under reduced pressure. The crude residue was dissolved in 5% aqueous NaOH (50 mL), resulting in a dull yellow solution. The aqueous solution was washed with DCM three times (500 mL total). The aqueous layer was acidified to pH 5 with acetic acid (6 mL), resulting in formation of a tan precipitate. The mixture was cooled in an ice-water bath, and the solids were filtered and washed with cold water. The solid was dried in a vacuum oven to give 2.9 g of 51 as a tan solid. The filtrate was concentrated to approximately 25 mL and a second crop (0.70 g) of 51 was collected by filtration. The total yield of 51 was 3.6 g. The crude material was used without further purification.

Step 2. 3-Methyl-7-(methyl-d₃)-1-(5-oxohexyl)-1H-purine-2,6(3H,7H)-dione (Compound 100)

Crude 51 (1.50 g, 8.2 mmol, 1 equiv) and powdered K₂CO₃ (2.28 g, 16.4 mmol, 2 equiv) were suspended in DMF (30 mL) and heated to 50° C. To the resulting tan suspension was added 6-chloro-2-hexanone (52, 1.2 mL, 9.0 mmol, 1.1 equiv) and the reaction temperature was raised to 130° C. Heating was continued at 130° C. for 2 h, during which time the suspension became finer and darker in color. The reaction mixture was cooled to rt and DMF was evaporated under reduced pressure. The residual tan paste was suspended in EtOAc (250 mL) and filtered to remove insoluble material. The filtrate was concentrated under reduced pressure resulting in a yellow oil. The crude product was purified using an Analogix chromatography system eluting with 100% EtOAc (10 minutes) followed by a gradient of 0 to 25% MeOH/EtOAc over 50 minutes (min). Product fractions were concentrated under reduced pressure to give a slightly yellow oil that solidified after standing for several minutes. The solid was triturated with heptanes (100 mL) and filtered to give 2.00 g of 100 as an off-white solid, mp 101.8-103.0° C. ¹H-NMR (300 MHz, CDCl₃): δ 1.64-1.68 (m, 4H), 2.15 (s, 3H), 2.51 (t, J=7.0, 2H), 3.57 (s, 3H), 4.01 (t, J=7.0, 2H), 7.52 (s, 1H). ¹³C-NMR (75 MHz, CDCl₃): δ 20.95, 27.41, 29.69, 29.98, 40.80, 43.18, 107.63, 141.41, 148.75, 151.45, 155.26, 208.80. HPLC (method: 20 mm C18-RP column—gradient method 2 to 95% ACN+0.1% formic acid in 3.3 min with 1.7 min hold at 95% ACN; Wavelength: 254 nm): retention time: 2.54 min; 98.5% purity. MS (M+H): 282.0. Elemental Analysis (C₁₃H₁₅D₃N₄O₃): Calculated: C=55.50, H=6.45, N=19.92. Found: C=55.58, H=6.48, N=19.76.

Due to the presence of a triplet at 4.01 ppm in the above ¹H-NMR spectrum, determination of the presence or absence of a singlet peak at around 3.99 ppm corresponding to the presence or absence of hydrogens on the N-methyl group at the 7 position (R¹) of the purine ring was not possible.

Example 2

Synthesis of 8-d₁-3-methyl-7-(methyl-d₃)-1-(6-d₃-4-d₂-5-oxohexyl)-1H-purine-2,6(3H,7H)-dione (Compound 409)

8-d₁-3-methyl-7-(methyl-d₃)-1-(6-d₃-4-d₂-5-oxo-hexyl)-1H-purine-2,6(3H,7H)-dione (Compound 409)

A suspension of 100 (1.80 g, 6.4 mmol, 1 equiv) and powdered K₂CO₃ (0.23 g, 1.7 mmol, 0.25 equiv) in D₂O (Cambridge Isotope Labs, 99 atom % D) (45 mL) was stirred under reflux conditions for 24 h during which time the suspension became a slightly yellow solution. The reaction mixture was cooled to rt, saturated with sodium chloride, and extracted four times with dichloromethane (400 mL total). The combined organic solution was dried over Na₂SO₄, filtered, and evaporated under reduced pressure to provide 1.7 g of a slightly yellow oil that solidified upon standing. The crude material was re-subjected to the hydrogen/deuterium exchange conditions described above with fresh K₂CO₃ and D₂O. After an identical workup, the off-white solid was triturated with hexanes (100 mL) and filtered to give 1.61 g of 409 as an off white solid, mp 99.6-99.8° C. ¹H-NMR (300 MHz, CDCl₃): δ 1.64-1.69 (m, 4H), 3.57 (s, 3H), 4.01 (t, J=7.0, 2H). ¹³C-NMR (75 MHz, CDCl₃): δ 21.05, 27.61, 29.90, 41.02, 107.83, 148.99, 151.69, 155.50, 209.28. HPLC (method: Waters Atlantis T3 2.1×50 mm 3 µm C18-RP column—gradient method 5-95% ACN+0.1% formic acid in 14 min (1.0 mL/min) with 4 min hold at 95% ACN; Wavelength: 254 nm): retention time: 3.26 min; 98% purity. MS (M+H): 288.3. Elemental Analysis (C₁₃H₉D₉N₄O₃): Calculated: C=54.35, H=6.31, N=19.50. Found: C=54.36, H=6.32, N=19.10.

Notable in the ¹H-NMR spectrum above was the absence of the following peaks: a singlet at around 2.15 ppm indicating an absence of methyl ketone hydrogens; a triplet at around 2.51 ppm indicating an absence of methylene ketone hydrogens; and a singlet at around 7.52 ppm indicating an absence of hydrogen at the number 8 position on the purine ring. Due to the presence of a triplet at 4.01 ppm in the above ¹H-NMR spectrum, determination of the presence or absence of a singlet peak at around 3.99 ppm corresponding to the presence or absence of hydrogens on the N-methyl group at the 7 position (R¹) of the purine ring was not possible.

Example 3

Synthesis of 3,7-Di(methyl-d₃)-1-(5-oxohexyl)-1H-purine-2,6(3H,7H)-dione (Compound 101)

Scheme 14. Preparation of Compounds 101 and 413.

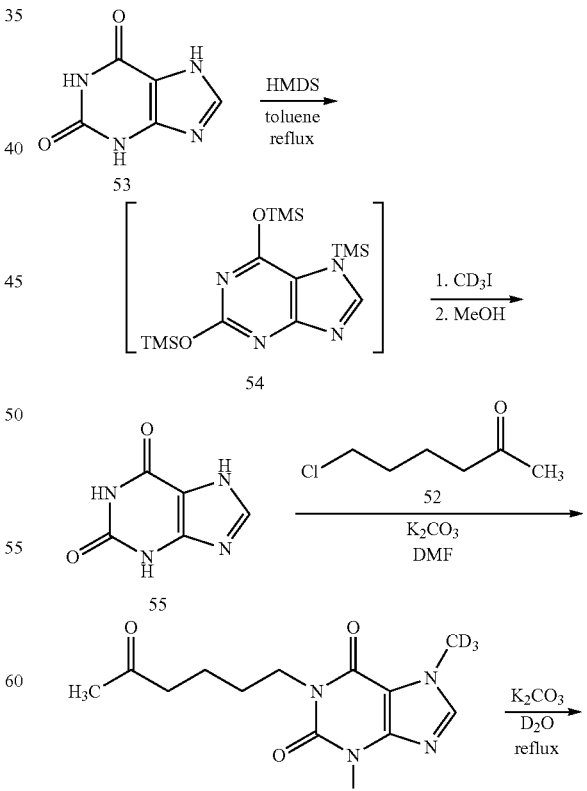

-continued

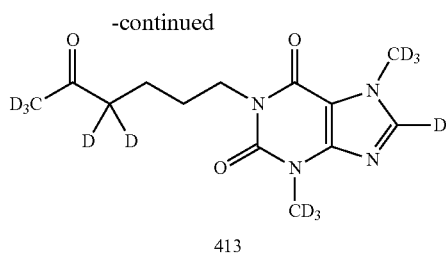

413

Step 1. 3,7-Di(methyl-$d_3$)-1H-purine-2,6(3H,7H)-dione (55)

A suspension of xanthine 53 (2.00 g, 13.2 mmol, 1.0 equiv) and hexamethyldisilazane (32 mL) in toluene (60 mL) was heated to reflux and stirred for 4 days. The reaction mixture was cooled to room temperature, diluted with additional toluene (50 mL) and filtered through Celite to remove any unreacted starting material. The filtrate was evaporated to dryness under reduced pressure to produce 54 as a white solid (4.1 g). A portion of this material (3.00 g) was placed in a 100 mL sealed tube reaction vessel, followed by the addition of toluene (60 mL) and $CD_3I$ (4 mL, Cambridge Isotopes, 99.5 atom % D). The reaction mixture was heated in a 120° C. oil bath and stirred for 24 hours, during which time the reaction mixture turned yellow and a solid formed. The reaction mixture was cooled to room temperature, resulting in the entire reaction mixture solidifying to a yellow solid. The mixture was diluted with acetone (30 mL) and MeOH (5 mL) and filtered under a stream of $N_2$. The solids were washed with acetone (100 mL) which removed the yellow color to afford an off-white solid. The solid was dried on the filter under a stream of $N_2$ to give a mixture of 55 and monoalkylated side product, 7-(methyl-$d_3$)-xanthine in a roughly 1:1 ratio. Total mass recovery was 2.6 g (42% crude yield). Due to the poor solubility of this mixture, it was carried forward without further purification.

Step 2. 3,7-Di(methyl-$d_3$)-1-(5-oxohexyl)-1H-purine-2,6(3H,7H)-dione (Compound 101)

A suspension of crude 55 (2.50 g, 13.4 mmol, 1.0 equiv) and powdered $K_2CO_3$ (2.20 g, 16 mmol, 1.2 equiv) in DMF (50 mL) was heated to 60° C. To the resulting tan suspension was added 6-chloro-2-hexanone 52 (2.0 mL, 14.8 mmol, 1.1 equiv) and the mixture was heated to 140° C. Heating was continued at 140° C. for 4 hours during which time the suspension became finer and darker in color. The reaction mixture was cooled to room temperature and the DMF was evaporated under reduced pressure. The resulting tan paste was suspended in 1:1 dichloromethane/ethyl acetate (200 mL) and filtered to remove insoluble material. The filtrate was concentrated under reduced pressure giving a yellowish-brown oil (3.0 g). This crude reaction product was adsorbed onto silica gel and dry-loaded onto a silica gel column packed with 100% dichloromethane. The column was eluted with a gradient of 0-5% MeOH/dichloromethane. Fractions containing product were concentrated under reduced pressure to give 0.75 g of a yellow oil. LCMS showed the material to be about 90% pure. The yellow oil was further purified using an Analogix chromatography system eluting initially with 60% EtOAc/heptanes followed by a gradient of 60-100% EtOAc/heptanes over 20 min. The desired product eluted at about 20 minutes. Fractions containing product were concentrated under reduced pressure to give 0.55 g (16%) of Compound 101 as a slightly yellow oil which solidified upon standing. $^1$H-NMR (300 MHz, $CDCl_3$): δ 1.64-1.69 (m, 4H), 2.15 (s, 3H), 2.51 (t, J=7.0, 2H), 4.02 (t, J=7.0, 2H), 7.51 (s, 1H). $^{13}$C-NMR (75 MHz, $CDCl_3$): δ 20.97, 27.43, 29.97, 40.80, 43.19, 107.64, 141.40, 148.78, 151.48, 155.29, 208.77. HPLC (method: Waters Atlantis T3 2.1×50 mm 3 μm C18-RP column—gradient method 5-95% ACN+0.1% formic acid in 14 min (1.0 mL/min) with 4 min hold at 95% ACN+0.1% formic acid; Wavelength: 305 nm): retention time: 3.24 min; 98.6% purity. MS (M+H): 285.3, (M+Na): 307.2. Elemental Analysis ($C_{13}H_{12}D_6N_4O_3$): Calculated: C=54.92, H=6.38, N=19.71. Found: C=54.90, H=6.40, N=19.50.

Notable in the $^1$H-NMR spectrum above was the absence of a singlet at around 3.57 ppm indicating an absence of N-methyl hydrogens at the 3 position of the purine ring. Due to the presence of a triplet at 4.01 ppm in the above $^1$H-NMR spectrum, determination of the presence or absence of a singlet peak at around 3.99 ppm corresponding to the presence or absence of hydrogens on the N-methyl group at the 7 position ($R^1$) of the purine ring was not possible.

Example 4

Synthesis of 8-$d_1$-3,7-Di(methyl-$d_3$)-1-(4,4,6,6,6-$d_5$-5-oxohexyl)-1H-purine-2,6(3H,7H)-dione (Compound 413)

8-$d_1$-3,7-Di(methyl-$d_3$)-1-(4-$d_2$-6-$d_3$-5-oxohexyl)-1H-purine-2,6(3H,7H)-dione (Compound 413)

A suspension of Compound 101 (0.60 g, 2.1 mmol, 1.0 equiv) and powdered $K_2CO_3$ (0.10 g, 0.72 mmol, 0.30 equiv) in $D_2O$ (15 mL, Cambridge Isotopes, 99 atom % D) was heated and stirred at reflux for 16 hours during which time the suspension became a slightly yellow solution. The reaction mixture was cooled to room temperature, saturated with sodium chloride, and extracted four times with dichloromethane (200 mL). The combined organic extracts were dried over $Na_2SO_4$, filtered, and concentrated under reduced pressure to provide 0.53 g of a slightly yellow oil that solidified upon standing. The crude reaction product was re-subjected to the above reaction conditions with fresh powdered $K_2CO_3$ and $D_2O$. After an identical workup, the off-white solid was triturated with hexanes (50 mL) and filtered to give 0.45 g (74%) of Compound 413 as an off-white solid, mp 99.2-99.3° C. $^1$H-NMR (300 MHz, $CDCl_3$): δ 1.64-1.71 (m, 4H), 4.01 (t, J=7.0, 2H). $^{13}$C-NMR (75 MHz, $CDCl_3$): δ 20.85, 27.41, 40.81, 107.63, 148.80, 151.50, 155.31, 209.09. HPLC (method: Waters Atlantis T3 2.1×50 mm 3 μm C18-RP column—gradient method 5-95% ACN+0.1% formic acid in 14 minutes (1.0 mL/min) with a 4 minute hold at 95% ACN+0.1% formic acid; Wavelength: 254 nm): retention time: 3.25 min; 98.7% purity. MS (M+H): 291.3, (M+Na): 313.2. Elemental Analysis ($C_{13}H_6D_{12}N_4O_3$): Calculated: C=53.78, H=6.25, N=19.30. Found: C=53.76, H=6.39, N=19.11.

Notable in the $^1$H-NMR spectrum above was the absence of the following peaks: a singlet at around 2.15 ppm indicating an absence of methyl ketone hydrogens; a triplet at around 2.51 ppm indicating an absence of methylene ketone hydrogens; a singlet around 3.57 ppm indicating an absence of N-methyl hydrogens at the 3 position on the purine ring; and a singlet at around 7.51 ppm indicating an absence of hydrogen at the number 8 position on the purine ring. Due to the presence of a triplet at 4.01 ppm in the above $^1$H-NMR spectrum, determination of the presence or absence of a singlet peak at around 3.99 ppm corresponding to the presence or absence of hydrogens on the N-methyl group at the 7 position (R[1]) of the purine ring was not possible.

Example 5

Synthesis of 3-Methyl-7-(methyl-d₃)-1-(6,6,6-d₃-5-oxohexyl)-1H-purine-2,6(3H,7H)-dione (Compound 99)

Scheme 15. Preparation of Compound 99.

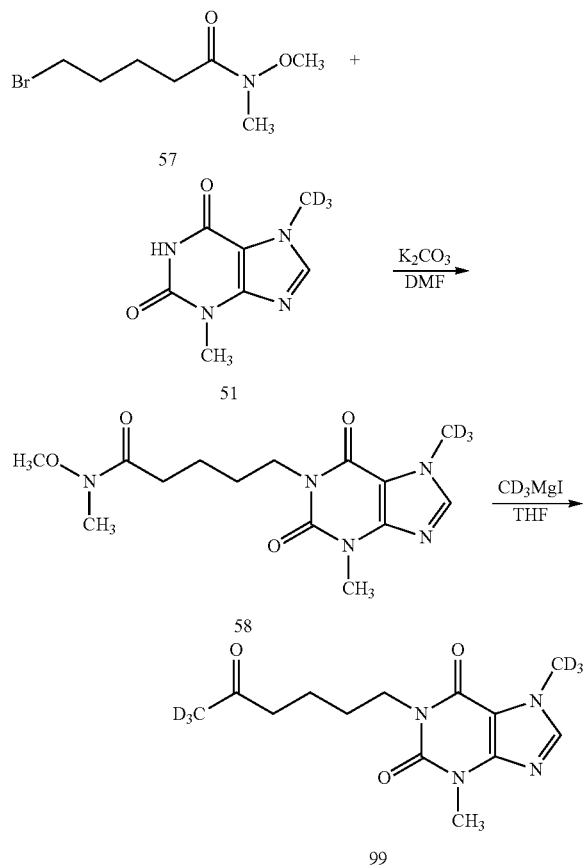

Step 1. 5-(3-Methyl-7-(methyl-d₃)-2,3,6,7-tetrahydro-1H-purin-1-yl)-N-methoxy-N-methylpentanamide (58)

A suspension of 51 (1.50 g, 8.2 mmol, 1.0 equiv, see Example 1 for preparation) and powdered K₂CO₃ (1.80 g, 12.9 mmol, 1.6 equiv) in DMF (40 mL) was heated to 60° C. 5-Bromo-N-methoxy-N-methylpentanamide 57 (2.21 g, 9.8 mmol, 1.2 equiv, prepared as outlined in Org. Lett., 2005, 7: 1427-1429) was added and the mixture was heated at 110° C. for 4 hours during which time the suspended solid became finer and tan in color. The reaction mixture was cooled to room temperature and DMF was evaporated under reduced pressure. The resulting tan paste was suspended in 1:1 CH₂Cl₂:ethyl acetate (250 mL) and the suspension was filtered to remove insoluble material. The filtrate was concentrated under reduced pressure to a yellow oil. This crude reaction product was purified using an Analogix automated chromatography system eluting with 100% CH₂Cl₂ for 8 minutes followed by a gradient of 0-5% MeOH/CH₂Cl₂ over 40 minutes. The desired product eluted at approximately 24 minutes. Fractions containing product were concentrated under reduced pressure to a slightly yellow oil. ¹H NMR of the oil indicated it contained approximately 10% unreacted 51. A second purification on an Analogix automated chromatography system eluting with 100% CH₂Cl₂ for 10 minutes followed by a gradient of 0-5% MeOH/CH₂Cl₂ over 50 minutes allowed for removal of the impurity. Fractions containing product were concentrated under reduced pressure to a slightly yellow oil that crystallized as an off-white solid on standing. The solid was triturated with heptanes (100 mL) and filtered to give 1.29 g (49%) of 58 as an off-white solid.

Step 2. 3-Methyl-7-(methyl-d₃)-1-(6,6,6-d₃-5-oxohexyl)-1H-purine-2,6(3H,7H)-dione (Compound 99)

A suspension of 58 (0.72 g, 2.2 mmol, 1.0 equiv) in THF (20 mL) was cooled to 2° C. and 1M CD₃MgI in ether (2.4 mL, 2.4 mmol, 1.1 equiv, Aldrich >99 atom % D) was added drop-wise via syringe at a rate to maintain the temperature below 5° C. During the addition, the mixture became a fine, slightly yellow suspension. When addition was complete, the reaction mixture was warmed to room temperature and was stirred for 3 hours. The mixture was cooled to 2° C. and an additional portion of CD₃MgI solution (0.4 mL, 0.4 mmol) was added. The mixture was allowed to warm to room temperature and was stirred an additional 3 hours. The reaction was quenched with 1N HCl (4 mL) and diluted with H₂O (10 mL) resulting in a slightly yellow solution that was extracted with CH₂Cl₂ (3×, 200 mL). The combined organic extracts were dried over Na₂SO₄, filtered, and concentrated under reduced pressure to a yellow oil. The crude product was purified using an Analogix automated chromatography system eluting with 100% CH₂Cl₂ for 8 minutes and then a gradient of 0-5% MeOH/CH₂Cl₂ over 40 minutes. The desired product elutes first at about 22 minutes, followed by unreacted starting material. Fractions containing the desired product were concentrated under reduced pressure to a yellow oil that solidified upon standing. The solid was triturated with hexane (25 mL) and collected via vacuum filtration to give 0.33 g (53%) of Compound 99 as a white solid, mp 93.7-94.4° C. Fractions containing unreacted starting material were also collected and concentrated to give 0.21 g of 58 as a clear, colorless oil. The recovered material was re-subjected to the above alkylation reaction to give, after workup and purification, an additional 0.06 g (33%, 62% overall based on total starting material) of Compound 99, mp 93.3-94.0° C. ¹H-NMR (300 MHz, CDCl₃): δ 1.64-1.68 (m, 4H), 2.50 (t, J=7.0, 2H), 3.58 (s, 3H), 4.02 (t, J=7.0, 2H), 7.51 (s, 1H). ¹³C-NMR (75 MHz, CDCl₃): δ 21.16, 27.65, 29.91, 41.03, 43.41, 107.87, 141.62, 149.00, 151.69, 155.50, 209.12. HPLC (method: Waters Atlantis T3 2.1×50 mm 3 μm C18-RP column—gradient method 5-95% ACN+0.1% formic acid in 14 min (1.0 mL/min) with 4 min hold at 95% ACN+0.1% formic acid; Wavelength: 305 nm): retention time: 3.24 min; 99.0% purity. MS (M+H): 285.3, (M+Na): 307.2. Elemental Analysis (C₁₃H₁₂D₆N₄O₃): Calculated: C=54.92, H=6.38, N=19.71. Found: C=54.85, H=6.36, N=19.49.

Notable in the ¹H-NMR spectrum above was the absence of a singlet at around 2.15 ppm indicating an absence of methyl ketone hydrogens. Due to the presence of a triplet at 4.01 ppm in the above ¹H-NMR spectrum, determination of the presence or absence of a singlet peak at around 3.99 ppm corresponding to the presence or absence of hydrogens on the N-methyl group at the 7 position ($R^1$) of the purine ring was not possible.

Example 6

Synthesis of (±)8-$d_1$-1-(4,4,6,6,6-$d_5$-5-Hydroxyhexyl)-3-methyl-7-(methyl-$d_3$)-1H-purine-2,6(3H,7H)-dione (Compound 419)

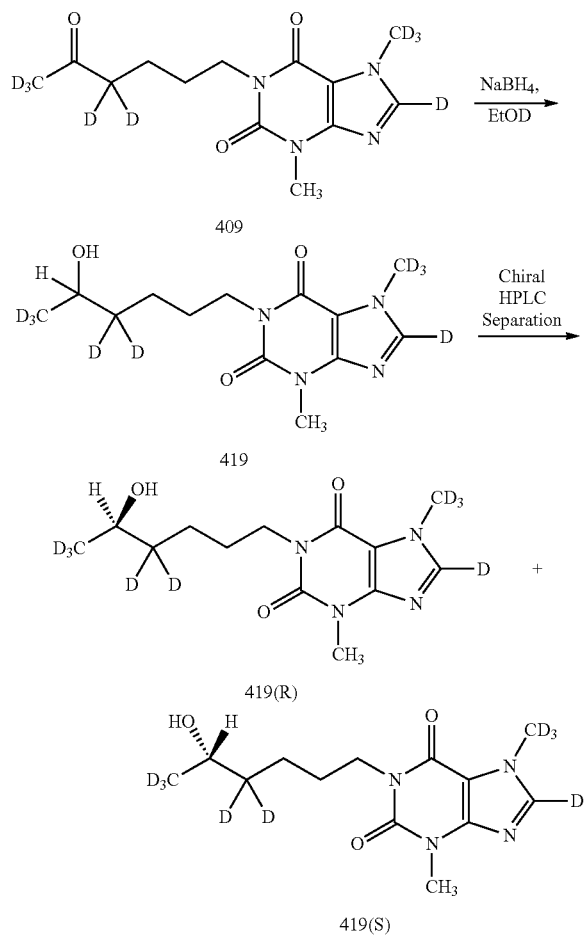

(±)8-$d_1$-1-(4,4,6,6,6-$d_5$-5-Hydroxyhexyl)-3-methyl-7-(methyl-$d_3$)-1H-purine-2,6(3H,7H)-dione (Compound 419)

Compound 409 (0.50 g, 1.7 mmol, 1.0 equiv, see Example 2) was dissolved in EtOD (13 mL, Aldrich 99.5 atom % D) and NaBH$_4$ (0.07 g, 1.9 mmol, 1.1 equiv) was added. An increase in temperature from 24 to 28° C. was observed. The reaction was stirred 2 hours at room temperature, then was quenched by the addition of D$_2$O (30 mL, Cambridge Isotope Labs, 99 atom % D). A white suspension formed that was extracted with MTBE (4×, 200 mL total). The combined organic extracts were dried over Na$_2$SO$_4$, filtered, and concentrated under reduced pressure to a clear, colorless oil (0.45 g). The crude product was purified by silica gel chromatography eluting first with 1% MeOH/CH$_2$Cl$_2$ followed by a gradient of 1-5% MeOH/CH$_2$Cl$_2$. Fractions containing product were concentrated under reduced pressure to give (0.41 g, 83%) of Compound 419 as a clear colorless oil that solidified on standing.

Example 7

Chiral Separation of (R)-8-$d_1$-1-(4,4,6,6,6-$d_5$-5-Hydroxyhexyl)-3-methyl-7-(methyl-$d_3$)-1H-purine-2,6(3H,7H)-dione (Compound 419(R)) and (S)-8-$d_1$-1-(4,4,6,6,6-$d_5$-5-Hydroxyhexyl)-3-methyl-7-(methyl-$d_3$)-1H-purine-2,6(3H,7H)-dione (Compound 419(S))

Separation of Enantiomers of Compound 419.

Compound 419 obtained from Example 6 above (0.38 g) was dissolved in a minimal amount of iPrOH (6 mL, HPLC grade, heating required) and diluted with hexane (4 mL, HPLC grade). Enantiomeric separation was achieved using a Waters HPLC system equipped with a preparative Daicel Chiralpak AD column (20×250 mm). For the first minute of the run, the mobile phase was 80% hexane and 20% iPrOH along with 0.1% diethylamine. After the first minute a gradient to 75% hexane and 25% iPrOH along with 0.1% diethylamine over 15 minutes was used, followed by holding at this solvent ratio for 17 minutes at a flow rate of 18 mL/min. This method resulted in baseline separation with 419(R) eluting first (21.0 min), followed by 419(S) (24.1 min). Fractions containing each enantiomer were concentrated under reduced pressure to give 0.16 g each of 419(R) (mp 107.8-108.8° C.) and 419(S) (mp 108.3-108.4° C.) as off-white solids.

A). (R)-8-$d_1$-1-(4,4,6,6,6-$d_5$-5-Hydroxyhexyl)-3-methyl-7-(methyl-$d_3$)-1H-purine-2,6(3H,7H)-dione (Compound 419(R))

$^1$H-NMR (300 MHz, CDCl$_3$): δ 1.36-1.50 (m, 2H), 1.60-1.74 (m, 3H), 3.58 (s, 3H), 3.80 (s, 1H), 4.02 (t, J=7.3, 2H). $^{13}$C-NMR (75 MHz, CDCl$_3$): δ 22.70, 27.86, 29.71, 41.14, 67.66, 107.66, 148.78, 151.54, 155.40. HPLC (method: Waters Atlantis T3 2.1×50 mm 3 μM C18-RP column—gradient method 5-95% ACN+0.1% formic acid in 14 min (1.0 mL/min) with 4 min hold at 95% ACN+0.1% formic acid; Wavelength: 254 nm): retention time: 3.26 min; 99.9% purity. Chiral HPLC (method: Chiralpak AD 25 cm column—isocratic method 78% hexane/22% isopropanol/0.01% diethylamine for 40 min at 1.00 mL/min; Wavelength: 254 nm): retention time: 27.51 min (major enantiomer); 31.19 min (expected for minor enantiomer): >99.9% ee purity. MS (M+H): 290.1, (M+Na): 312.3. Elemental Analysis (C$_{13}$H$_{11}$D$_9$N$_4$O$_3$): Calculated: C=53.97, H=6.97, N=19.36. Found: C=54.39, H=7.11, N=18.98.

Notable in the $^1$H-NMR spectrum above was the absence of the following peaks: a peak at around 1.19 ppm indicating an absence of methyl hydrogens alpha to the hydroxyl group; and a singlet at around 7.51 ppm indicating an absence of hydrogen at the number 8 position on the purine ring. Due to the presence of a multiplet at 1.36-1.50 ppm and a triplet at 4.01 ppm in the above $^1$H-NMR spectrum, determination of the presence or absence a peak at 1.51 ppm corresponding to the presence or absence of methylene hydrogens alpha to the hydroxyl group and of a singlet peak at around 3.99 ppm corresponding to the presence or absence of hydrogens on the N-methyl group at the 7 position ($R^1$) of the purine ring was not possible.

B). (S)-8-$d_1$-1-(4,4,6,6,6-$d_5$-5-Hydroxyhexyl)-3-methyl-7-(methyl-d?)-1H-purine-2,6(3H,7H)-dione (Compound 419(S))

$^1$H-NMR (300 MHz, CDCl$_3$): δ 1.41-1.48 (m, 2H), 1.64-1.72 (m, 3H), 3.58 (s, 3H), 3.79 (s, 1H), 4.02 (t, J=7.4, 2H). $^{13}$C-NMR (75 MHz, CDCl$_3$): δ 22.70, 27.86, 29.71, 41.15, 67.66, 107.67, 148.78, 151.54, 155.41. HPLC (method: Waters Atlantis T3 2.1×50 mm 3 μm C18-RP column—gradient method 5-95% ACN+0.1% formic acid in 14 min (1.0 mL/min) with 4 min hold at 95% ACN+0.1% formic acid; Wavelength: 254 nm): retention time: 3.26 min; 99.9% purity. Chiral HPLC (method: Chiralpak AD 25 cm column—isocratic method 78% hexane/22% isopropanol/0.01% diethylamine for 40 min at 1.00 mL/min; Wavelength: 254 nm): retention time: 31.19 min (major enantiomer); 27.51 min (expected for minor enantiomer): >99.9% ee purity. MS (M+H): 290.1, (M+Na): 312.3. Elemental Analysis (C$_{13}$H$_{11}$D$_9$N$_4$O$_3$): Calculated: C=53.97, H=6.97, N=19.36. Found: C=54.35, H=7.28, N=18.75.

Notable in the $^1$H-NMR spectrum above was the absence of the following peaks: a peak at around 1.19 ppm indicating an absence of methyl hydrogens alpha to the hydroxyl group; and a singlet at around 7.51 ppm indicating an absence of hydrogen at the number 8 position on the purine ring. Due to the presence of a multiplet at 1.36-1.50 ppm and a triplet at 4.01 ppm in the above $^1$H-NMR spectrum, determination of the presence or absence a peak at 1.51 ppm corresponding to the presence or absence of methylene hydrogens alpha to the hydroxyl group and of a singlet peak at around 3.99 ppm corresponding to the presence or absence of hydrogens on the N-methyl group at the 7 position ($R^1$) of the purine ring was not possible.

Example 8

Synthesis of (±)8-$d_1$-1-(4,4,5,6,6,6-$d_6$-5-Hydroxyhexyl)-3-methyl-7-(methyl-4)-1H-purine-2,6(3H,7H)-dione (Compound 435)

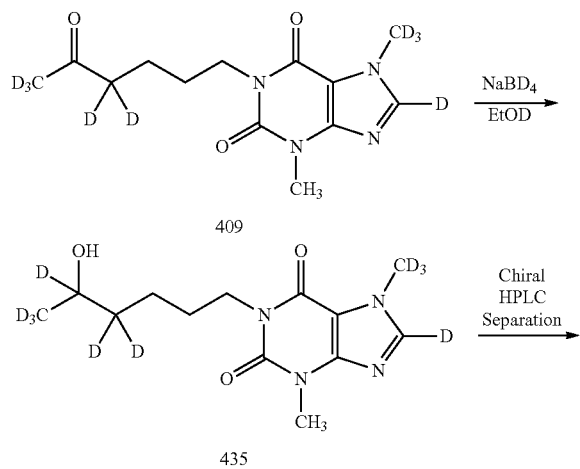

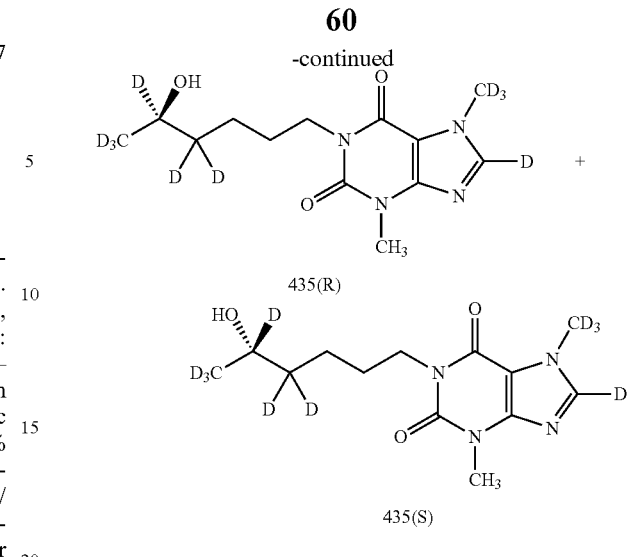

(±)8-$d_1$-1-(4,4,5,6,6,6-$d_6$-5-Hydroxyhexyl)-3-methyl-7-(methyl-$d_3$)-1H-purine-2,6(3H,7H)-dione (Compound 435)

To a solution of Compound 409 (0.50 g, 1.7 mmol, 1.0 equiv) in EtOD (13 mL, Aldrich 99.5 atom % D) was added NaBD$_4$ (0.08 g, 1.9 mmol, 1.1 equiv, Cambridge Isotope Labs, 99 atom % D). An increase in temperature from 24 to 27° C. was observed. The reaction was stirred 2 hours at room temperature then was quenched by the addition of D$_2$O (30 mL) (Cambridge Isotope, 99 atom % D). A white suspension formed that was extracted with MTBE (4×, 200 mL total). The combined organic extracts were dried over Na$_2$SO$_4$, filtered, and concentrated under reduced pressure to a clear, colorless oil (0.45 g). The crude product was purified by silica gel chromatography eluting first with 1% MeOH/CH$_2$Cl$_2$ followed by a gradient of 1-5% MeOH/CH$_2$Cl$_2$. Fractions containing product were concentrated under reduced pressure to give 0.40 g (81%) of Compound 435 as a clear colorless oil that solidified on standing.

Example 9

Chiral Separation of (R)-8-$d_1$-1-(4,4,5,6,6,6-$d_6$-5-Hydroxyhexyl)-3-methyl-7-(methyl-$d_3$)-1H-purine-2,6(3H,7H)-dione (Compound 435(R)) and (S)-8-$d_1$-1-(4,4,5,6,6,6-$d_6$-5-Hydroxyhexyl)-3-methyl-7-(methyl-$d_3$)-1H-purine-2,6(3H,7H)-dione (Compound 435(S))

Separation of Enantiomers of Compound 435.

Compound 435 obtained from Example 8 above (0.32 g) was dissolved in a minimal amount of iPrOH (5 mL, HPLC grade, heating was required) and diluted with hexane (4 mL, HPLC grade). Enantiomer separation was achieved using a Waters HPLC system equipped with a preparative Daicel Chiralpak AD column (20×250 mm). For the first minute of the run, the mobile phase was 80% hexane and 20% iPrOH along with 0.1% diethylamine. After the first minute a gradient to 75% hexane and 25% iPrOH along with 0.1% diethylamine over 15 minutes was used, followed by holding at this solvent ratio for 17 minutes at a flow rate of 18 mL/min. This method resulted in baseline separation with Compound 435(R) eluting first (21.9 min), followed by Compound 435(S) (25.2 min). Fractions containing each enantiomer were concentrated under reduced pressure to give 0.12 g each of 435(R) (mp 108.0-108.1° C.) and 435(S) (mp 107.6-107.7° C.) as off-white solids.

A). (R)-8-d$_1$-1-(4,4,5,6,6,6-d$_6$-5-Hydroxyhexyl)-3-methyl-7-(methyl-d$_3$)-1H-purine-2,6(3H,7H)-dione (Compound 435(R))

$^1$H-NMR (300 MHz, CDCl$_3$): δ 1.40-1.48 (m, 3H), 1.66-1.70 (m, 2H), 3.58 (s, 3H), 4.02 (t, J=7.5, 2H). $^{13}$C-NMR (75 MHz, CDCl$_3$): δ 22.66, 27.86, 29.71, 41.15, 107.67, 148.80, 151.54, 155.41. HPLC (method: Waters Atlantis T3 2.1×50 mm 3 µm C18-RP column—gradient method 5-95% ACN+ 0.1% formic acid in 14 min (1.0 mL/min) with 4 min hold at 95% ACN+0.1% formic acid; Wavelength: 254 nm): retention time: 3.25 min; 99.8% purity. Chiral HPLC (method: Chiralpak AD 25 cm column—isocratic method 78% hexane/22% isopropanol/0.01% diethylamine for 40 min at 1.00 mL/min; Wavelength: 254 nm): retention time: 27.24 min (major enantiomer); 31.11 min (expected for minor enantiomer): >99.9% ee purity. MS (M+H): 291.3, (M+Na): 313.2. Elemental Analysis (C$_{13}$H$_{10}$D$_{10}$N$_4$O$_3$): Calculated: C=53.78, H=6.94, N=19.30. Found: C=54.01, H=7.07, N=18.90.

Notable in the $^1$H-NMR spectrum above was the absence of the following peaks: a peak at around 1.19 ppm indicating an absence of methyl hydrogens alpha to the hydroxyl group; a peak at around 3.80 ppm indicating an absence of hydrogen at the methinyl hydroxyl position; and a singlet at around 7.51 ppm indicating an absence of hydrogen at the number 8 position on the purine ring. Due to the presence of a multiplet at 1.36-1.50 ppm and a triplet at 4.01 ppm in the above $^1$H-NMR spectrum, determination of the presence or absence a peak at 1.51 ppm corresponding to the presence or absence of methylene hydrogens alpha to the hydroxyl group and of a singlet peak at around 3.99 ppm corresponding to the presence or absence of hydrogens on the N-methyl group at the 7 position (R$^1$) of the purine ring was not possible.

B). (S)-8-d$_1$-1-(4,4,5,6,6,6-d$_6$-5-Hydroxyhexyl)-3-methyl-7-(methyl-4)-1H-purine-2,6(3H,7H)-dione (Compound 435(S))

$^1$H-NMR (300 MHz, CDCl$_3$): δ 1.41-1.48 (m, 3H), 1.62-1.72 (m, 2H), 3.58 (s, 3H), 4.03 (t, J=7.4, 2H). $^{13}$C-NMR (75 MHz, CDCl$_3$): δ 22.69, 27.90, 29.70, 41.17, 107.69, 148.82, 151.58, 155.43. HPLC (method: Waters Atlantis T3 2.1×50 mm 3 µm C18-RP column—gradient method 5-95% ACN+ 0.1% formic acid in 14 min (1.0 mL/min) with 4 min hold at 95% ACN+0.1% formic acid; Wavelength: 254 nm): retention time: 3.25 min; 99.5% purity. Chiral HPLC (method: Chiralpak AD 25 cm column—isocratic method 78% hexane/22% isopropanol/0.01% diethylamine for 40 min at 1.00 mL/min; Wavelength: 254 nm): retention time: 31.11 min (major enantiomer); 27.24 min (expected for minor enantiomer): >99.9% ee purity. MS (M+H): 291.3, (M+Na): 313.2. Elemental Analysis (C$_{13}$H$_{10}$D$_{10}$N$_4$O$_3$): Calculated: C=53.78, H=6.94, N=19.30. Found: C=54.01, H=7.11, N=18.78.

Notable in the $^1$H-NMR spectrum above was the absence of the following peaks: a peak at around 1.19 ppm indicating an absence of methyl hydrogens alpha to the hydroxyl group; a peak at around 3.80 ppm indicating an absence of hydrogen at the methinyl hydroxyl position; and a singlet at around 7.51 ppm indicating an absence of hydrogen at the number 8 position on the purine ring. Due to the presence of a multiplet at 1.36-1.50 ppm and a triplet at 4.01 ppm in the above $^1$H-NMR spectrum, determination of the presence or absence a peak at 1.51 ppm corresponding to the presence or absence of methylene hydrogens alpha to the hydroxyl group and of a singlet peak at around 3.99 ppm corresponding to the presence or absence of hydrogens on the N-methyl group at the 7 position (R$^1$) of the purine ring was not possible.

Example 10

Synthesis of 8-d$_1$-3,7-Dimethyl-1-(4,4,6,6,6-d$_5$-5-oxohexyl)-1H-purine-2,6(3H,7H)-dione (Compound 407)

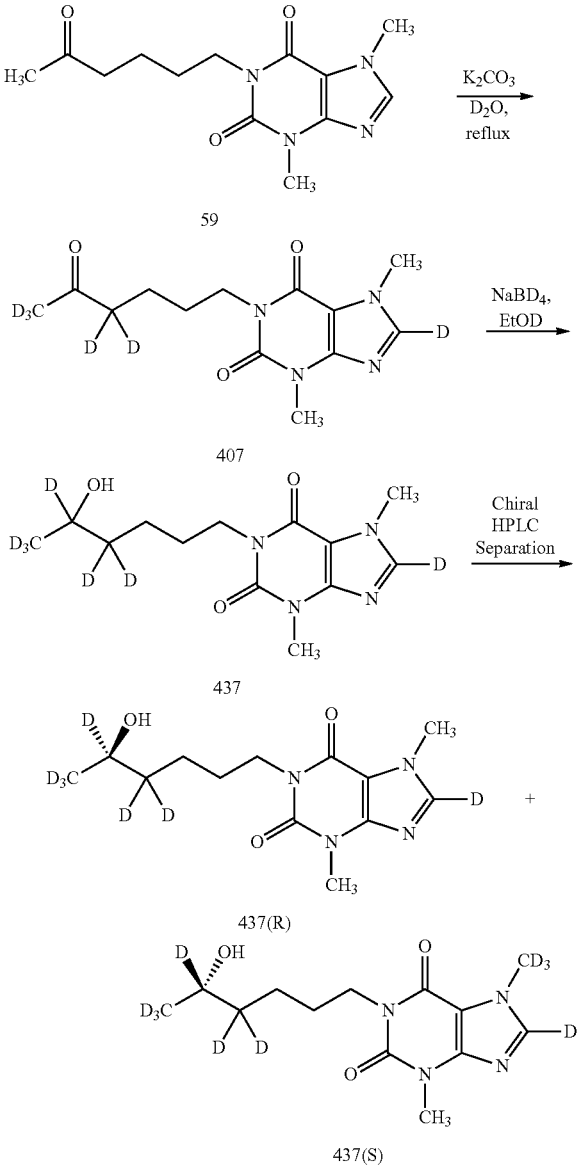

Scheme 18. Preparation of Compounds 407, 437, 437(R), and 437(S).

8-d$_1$-3,7-Dimethyl-1-(4,4,6,6,6-d$_5$-5-oxohexyl)-1H-purine-2,6(3H,7H)-dione (Compound 407). A mixture of commercially-available 59 (7.95 g, 28.6 mmol) and potassium carbonate (990 mg, 7.2 mmol) in D$_2$O (195 mL, Cambridge Isotopes, 99.9 atom % D) was heated to reflux for 24 hours. The suspended solid dissolved gradually giving a yellow solution. The solution was cooled to approximately 40° C. and was concentrated under reduced pressure to a tan solid. The solid was dissolved in $D_2O$ (195 mL) and the solution was heated to reflux for another 24 hours. The solution was cooled to room temperature and concentrated under reduced pressure to a tan solid. Ethyl acetate (200 mL) was added and the mixture was stirred 0.5 hours at approximately 40° C. The insoluble materials were filtered off and the filtrate was concentrated under reduced pressure to a pale yellow solid, which was triturated with MTBE (40 mL) to give 7.5 g (93%) of Compound 407 as an off-white solid. $^1$H-NMR (300 MHz, $CDCl_3$): δ 1.64-1.68 (m, 4H), 3.57 (s, 3H), 3.99 (s, 3H), 3.99-4.04 (m, 2H). $^{13}$C-NMR (75 MHz, $CDCl_3$): δ 20.84, 27.40, 29.69, 33.57, 40.81, 107.62, 148.77, 151.48, 155.28, 209.07. HPLC (method: Waters Atlantis T3 2.1×50 mm 3 μm C18-RP column—gradient method 5-95% ACN+ 0.1% formic acid in 14 min (1.0 mL/min) with 4 min hold at 95% ACN+0.1% formic acid; Wavelength: 305 nm): retention time: 3.24 min; 99.9% purity. MS (M+H): 285.3, (M+Na): 307.2. Elemental Analysis ($C_{13}H_{12}D_6N_4O_3$): Calculated: C=54.92, H=6.38, N=19.71. Found: C=54.89, H=6.38, N=19.70.

Notable in the $^1$H-NMR spectrum above was the absence of the following peaks: a singlet at around 2.15 ppm indicating an absence of methyl ketone hydrogens; a triplet at around 2.51 ppm indicating an absence of methylene ketone hydrogens; and a singlet at around 7.52 ppm indicating an absence of hydrogen at the number 8 position on the purine ring.

Example 11

Synthesis of (±)8-$d_1$-1-(4,4,5,6,6,6-$d_6$-5-Hydroxyhexyl)-3,7-dimethyl-1H-purine-2,6(3H,7H)-dione (Compound 437)

(±)8-$d_1$-1-(4,4,5,6,6,6-$d_6$-5-Hydroxyhexyl)-3,7-dimethyl-1H-purine-2,6(3H,7H)-dione (Compound 437)

Sodium borodeuteride (1.06 g, 25.3 mmol, Cambridge Isotopes, 99 atom % D) was added to a suspension of 407 (6.5 g, 22.9 mmol) in ethanol-$d_1$ (65 mL, Aldrich, 99.5 atom % D) at 0° C. The mixture was warmed to room temperature and stirred until a clear solution had developed (approximately 1 hour). The reaction was quenched with a saturated solution of ammonium chloride-$d_4$ (Cambridge Isotopes, 98 atom % D) in $D_2O$ (8 mL, Cambridge Isotope, 99.9 atom % D), ethanol-$d_1$ was evaporated under reduced pressure and the residue was extracted with EtOAc (160 mL). The organic phase was washed with $D_2O$ (20 mL), dried over sodium sulfate, filtered and concentrated under reduced pressure to give 4.8 g (73%) of Compound 437 as a pale yellow solid.

Example 12

Chiral Separation of (R)-8-$d_1$-1-(4,4,5,6,6,6-$d_6$-5-Hydroxyhexyl)-3,7-dimethyl-1H-purine-2,6(3H,7H)-dione (Compound 437(R)) and (S)-8-$d_1$-1-(4,4,5,6,6,6-$d_6$-5-Hydroxyhexyl)-3,7-dimethyl-1H-purine-2,6(3H,7H)-dione (Compound 437(S))

Separation of Enantiomers of Compound 437.

Compound 437 obtained from Example 11 above (1.60 g) was dissolved in iPrOH (20 mL, HPLC grade, heating required). Enantiomeric separation was achieved using a Waters HPLC system equipped with a preparative Chiralpak AD column (20×250 mm Daicel, 10 μM) with a preparative Chiralpak AD guard column (20×50 mm Daicel, 10 μM) preceding it. For the first minute of the run, the sample was eluted with 20% iPrOH/hexanes (henceforth, with 0.1% diethylamine as co-eluent) while ramping up from a flow rate of 15 mL/min to 18 mL/min. Over the next 15 minutes, the sample was eluted at a flow rate of 18 mL/min with a gradient of 20% to 25% iPrOH/hexanes. For the next 19 minutes the sample was eluted at a flow rate of 18 mL/min with 25% iPrOH/hexanes. Over the next 0.5 minutes, the sample was eluted at a flow rate of 18 mL/min with a gradient of 25% to 20% iPrOH/hexanes. For the next 4.5 minutes, the sample was eluted at a flow rate of 18 mL/min with 20% iPrOH/hexanes. This elution method resulted in baseline separation of Compound 437(R) eluting first (retention time approximately 29 min) and Compound 437(S) eluting second (retention time approximately 33 min). Fractions containing each enantiomer were collected and concentrated under reduced pressure to give 340 mg of 437(R) (mp 112.0-114.5° C.) and 375 mg of 437(S) (mp 111.9-112.3° C.) as off-white solids. [Note: only 1.0 g of 437 was injected from the solution prepared above.]

A. (R)-8-$d_1$-1-(4,4,5,6,6,6-$d_6$-5-Hydroxyhexyl)-3,7-dimethyl-1H-purine-2,6(3H,7H)-dione (Compound 437(R))

$^1$H-NMR (300 MHz, $CDCl_3$): δ 1.36-1.50 (m, 2H), 1.54 (s, 1H), 1.64-1.74 (m, 2H), 3.58 (s, 3H), 3.99 (s, 3H), 4.00-4.05 (m, 2H). $^{13}$C-NMR (75 MHz, $CDCl_3$): δ 22.66, 27.86, 29.70, 33.59, 41.14, 107.65, 148.76, 151.52, 155.40. HPLC (method: Waters Atlantis T3 2.1×50 mm 3 μm C18-RP column—gradient method 5-95% ACN+0.1% formic acid in 14 min (1.0 mL/min) with 4 min hold at 95% ACN+0.1% formic acid; Wavelength: 305 nm): retention time: 3.28 min; 99.9% purity. Chiral HPLC (method: Chiralpak AD 25 cm column—isocratic method 78% hexane/22% isopropanol/0.01% diethylamine for 40 min at 1.00 mL/min; Wavelength: 254 nm): retention time: 25.20 min (major enantiomer); 28.39 min (expected for minor enantiomer): >99.9% ee purity. MS (M+H): 288.3, (M+Na): 310.2. Elemental Analysis ($C_{13}H_{13}D_7N_4O_3$): Calculated: C=54.34, H=7.02, N=19.50. Found: C=54.32, H=7.23, N=19.35.

Notable in the $^1$H-NMR spectrum above was the absence of the following peaks: a peak at around 1.19 ppm indicating an absence of methyl hydrogens alpha to the hydroxyl group; a peak at around 3.80 ppm indicating an absence of hydrogen at the methinyl hydroxyl position; and a singlet peak at around 7.51 ppm indicating an absence of hydrogen at the number 8 position on the purine ring. Due to the presence of a multiplet at 1.36-1.50 ppm in the above $^1$H-NMR spectrum, determination of the presence or absence a peak at 1.51 ppm corresponding to the presence or absence of methylene hydrogens alpha to the hydroxyl group was not possible.

B. (S)-8-$d_1$-1-(4,4,5,6,6,6-$d_6$-5-Hydroxyhexyl)-3,7-dimethyl-1H-purine-2,6(3H,7H)-dione (Compound 437(S))

$^1$H-NMR (300 MHz, $CDCl_3$): δ 1.38-1.48 (m, 2H), 1.55 (s, 1H), 1.64-1.72 (m, 2H), 3.58 (s, 3H), 3.99 (s, 3H), 4.00-4.05 (m, 2H). $^{13}$C-NMR (75 MHz, $CDCl_3$): δ 22.65, 27.84, 29.71, 33.59, 41.13, 107.64, 148.75, 151.52, 155.39. HPLC (method: Waters Atlantis T3 2.1×50 mm 3 μm C18-RP column—gradient method 5-95% ACN+0.1% formic acid in 14 min (1.0 mL/min) with 4 min hold at 95% ACN+0.1% formic acid; Wavelength: 305 nm): retention time: 3.27 min; 99.9% purity. Chiral HPLC (method: Chiralpak AD 25 cm column—isocratic method 78% hexane/22% isopropanol/0.01% diethylamine for 40 min at 1.00 mL/min; Wavelength: 254 nm): retention time: 28.39 min (major enantiomer); 25.20 min (expected for minor enantiomer): >99.9% ee purity. MS (M+H): 288.3, (M+Na): 310.2. Elemental Analysis ($C_{13}H_{13}D_7N_4O_3$): Calculated: C=54.34, H=7.02, N=19.50. Found: C=54.33, H=7.30, N=19.36.

Notable in the $^1$H-NMR spectrum above was the absence of the following peaks: a peak at around 1.19 ppm indicating an absence of methyl hydrogens alpha to the hydroxyl group; a peak at around 3.80 ppm indicating an absence of hydrogen at the methinyl hydroxyl position; and a singlet peak at around 7.51 ppm indicating an absence of hydrogen at the number 8 position on the purine ring. Due to the presence of a multiplet at 1.36-1.50 ppm in the above $^1$H-NMR spectrum, determination of the presence or absence a peak at 1.51 ppm corresponding to the presence or absence of methylene hydrogens alpha to the hydroxyl group was not possible.

Example 13

Synthesis of (±)1-(5-$d_1$-5-Hydroxyhexyl)-3-methyl-7-(methyl-$d_3$)-1H-purine-2,6(3H,7H)-dione (Compound 131)

Scheme 19. Preparation of Compounds 131, 131(R), and 131(S).

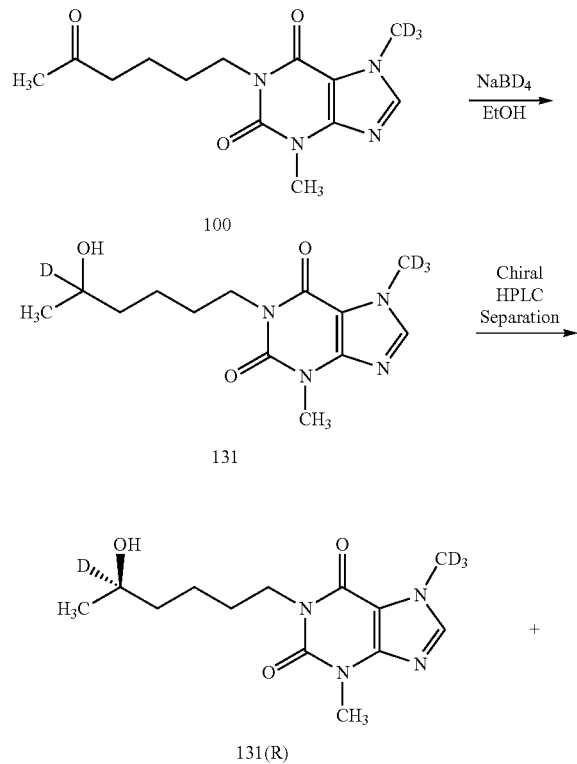

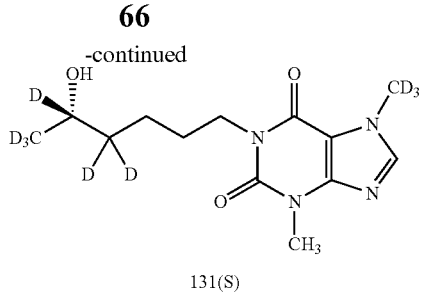

131(S)

(±)1-(5-$d_1$-5-Hydroxyhexyl)-3-methyl-7-(methyl-$d_3$)-1H-purine-2,6(3H,7H)-dione (Compound 131)

Following the same general method as for the synthesis of Compound 437 above, Compound 100 (see Example 1) was treated with NaBD$_4$ in EtOH to afford Compound 131.

Example 14

Chiral Separation of (R)-1-(5-$d_1$-5-Hydroxyhexyl)-3-methyl-7-(methyl-$d_3$)-1H-purine-2,6(3H,7H)-dione (Compound 131(R)) and (S)-1-(5-$d_1$-5-Hydroxyhexyl)-3-methyl-7-(methyl-$d_3$)-1H-purine-2,6(3H,7H)-dione (Compound 131(S))

Separation of Enantiomers of Compound 131.

A portion of racemic Compound 131 obtained from Example 13 above was separated in the same manner as racemic Compound 437 above, to afford separated enantiomers Compound 131(R) (mp 112.2-112.7° C.) (210 mg) and Compound 131(S) (mp 112.0-112.1° C.) (220 mg).

A. (R)-1-(5-$d_1$-5-Hydroxyhexyl)-3-methyl-7-(methyl-$d_3$)-1H-purine-2,6(3H,7H)-dione (Compound 131(R))

$^1$H-NMR (300 MHz, CDCl$_3$): δ 1.19 (s, 3H), 1.39-1.56 (m, 5H), 1.64-1.74 (m, 2H), 3.58 (s, 3H), 4.03 (t, J=7.3, 2H), 7.51 (s, 1H). $^{13}$C-NMR (75 MHz, CDCl$_3$): δ 22.87, 23.40, 27.89, 29.71, 38.64, 41.13, 107.68, 141.40, 148.76, 151.52, 155.39. HPLC (method: Waters Atlantis T3 2.1×50 mm 3 μm C18-RP column—gradient method 5-95% ACN+0.1% formic acid in 14 min (1.0 mL/min) with 4 min hold at 95% ACN+0.1% formic acid; Wavelength: 305 nm): retention time: 3.29 min; 99.9% purity. Chiral HPLC (method: Chiralpak AD 25 cm column—isocratic method 78% hexane/22% isopropanol/0.01% diethylamine for 40 min at 1.00 mL/min; Wavelength: 254 nm): retention time: 25.14 min (major enantiomer); 28.51 min (expected for minor enantiomer): >99.9% ee purity. MS (M+H): 285.3, (M+Na): 307.2. Elemental Analysis ($C_{13}H_{16}D_4N_4O_3$): Calculated: C=54.92, H=7.09, N=19.71. Found: C=54.67, H=7.04, N=19.35.

Notable in the $^1$H-NMR spectrum above was the absence of a peak at around 3.80 ppm indicating an absence of hydrogen at the methinyl hydroxyl position. Due to the presence of a triplet at 4.01 ppm in the above $^1$H-NMR spectrum, determination of the presence or absence of a singlet peak at around 3.99 ppm corresponding to the presence or absence of hydrogens on the N-methyl group at the 7 position ($R^1$) of the purine ring was not possible.

B. (S)-1-(5-$d_1$-5-Hydroxyhexyl)-3-methyl-7-(methyl-$d_3$)-1H-purine-2,6(3H,7H)-dione (Compound 131(S))

$^1$H-NMR (300 MHz, CDCl$_3$): δ 1.18 (s, 3H), 1.39-1.55 (m, 5H), 1.67-1.72 (m, 2H), 3.58 (s, 3H), 4.03 (t, J=7.3, 2H), 7.51 (s, 1H). $^{13}$C-NMR (75 MHz, CDCl$_3$): δ 23.10, 23.63, 28.12, 29.94, 38.87, 41.36, 107.91, 141.63, 148.99, 151.75, 155.62. HPLC (method: Waters Atlantis T3 2.1×50 mm 3 µm C18-RP column—gradient method 5-95% ACN+0.1% formic acid in 14 min (1.0 mL/min) with 4 min hold at 95% ACN+0.1% formic acid; Wavelength: 305 nm): retention time: 3.29 min; 99.9% purity. Chiral HPLC (method: Chiralpak AD 25 cm column—isocratic method 78% hexane/22% isopropanol/0.01% diethylamine for 40 min at 1.00 mL/min; Wavelength: 254 nm): retention time: 28.51 min (major enantiomer); 25.14 min (expected for minor enantiomer): >99.9% ee purity. MS (M+H): 285.3, (M+Na): 307.2. Elemental Analysis (C$_{13}$H$_{16}$D$_4$N$_4$O$_3$): Calculated: C=54.92, H=7.09, N=19.71. Found: C=54.65, H=7.04, N=19.32.

Notable in the $^1$H-NMR spectrum above was the absence of a peak at around 3.80 ppm indicating an absence of hydrogen at the methinyl hydroxyl position. Due to the presence of a triplet at 4.01 ppm in the above $^1$H-NMR spectrum, determination of the presence or absence of a singlet peak at around 3.99 ppm corresponding to the presence or absence of hydrogens on the N-methyl group at the 7 position ($R^1$) of the purine ring was not possible.

Biological Evaluation

Example 15a

Evaluation of Pharmacokinetics in Dogs Following Oral Administration. Comparison of Compound 409 and Pentoxifylline Metabolism of the title compounds were studied following oral administration to male beagle dogs. Blood samples were removed from dosed dogs at various time points and plasma isolated therefrom. The plasma samples were used for the determination of plasma drug levels by LC-MS/MS (liquid chromatography with tandem mass spectrometry) for estimating pharmacokinetic parameters.

Compound 409 and pentoxifylline were dissolved separately in saline to a concentration of 4 mg/mL. A 1:1 (v/v) mixture of the two solutions was prepared to yield a solution having a final concentration of 2 mg/mL of both Compound 409 and pentoxifylline.

Two male beagle dogs were fasted overnight and then orally dosed via gavage with 2.5 mg/kg of Compound 409 and pentoxifylline using the mixture described above. Blood samples (1.5-2 mL) were collected via the femoral vein at 0 min (pre-dose), 15 min, 30 min, 45 min, 1 hr, 1.5 hr, 2 hr, 3 hr, 4 hr, 6 hr, 8 hr, 10 hr, 12 hr, 16 hr and 24 hr post-dose. Blood was stored on ice prior to centrifugation to obtain plasma samples. Centrifugation took place within 1 hour of blood collection to harvest plasma (maximum volume). The plasma was decanted immediately and frozen/stored at −70° C. until analysis.

TABLE 8

Plasma Levels of Compound 409 vs Pentoxifylline in Dogs (Example 15a)

| Compound | Ave. Cmax (ng/mL) | Ave. AUC (hr*ng/mL) |
|---|---|---|
| Pentoxifylline | 784 | 448 |
| Compound 409 | 1230 | 811 |
| % Difference[a] | +57% | +80% |

[a]% Difference = [(deuterated species) − (nondeuterated species)](100)/(nondeuterated species)

Table 8 shows the results of the evaluation described in Example 15a. The average $C_{max}$ and average AUC for Compound 409, a deuterated version of pentoxifylline, were significantly greater than for pentoxifylline. The deuterated compound exhibited greater exposure in the dog plasma than pentoxifylline.

Example 15b

Repeat Evaluation of Pharmacokinetics in Dogs Following Oral Administration. Comparison of Compound 409 and Pentoxifylline with Monitoring of Metabolites Example 15a was repeated with additional monitoring of the pentoxifylline and Compound 409 metabolites. In this experiment Compound 409 and pentoxifylline were dissolved separately in saline to a concentration of 4.4 and 4 mg/mL respectively. A 1:1 (v/v) mixture of the two solutions was prepared to yield a solution having a final concentration of 2.2 mg/mL of Compound 409 and 2 mg/mL pentoxifylline. Post-dosing data analysis included adjustments to account for the 10% difference in dosing concentration between compound 409 and pentoxifylline.

Four beagle dogs (2-3 years of age, and weighed 5 to 8 kg) were fasted overnight and then orally dosed via gavage with 2.75 mg/kg Compound 409 and 2.5 mg/kg pentoxifylline using the mixture described above. Blood samples (approximately 1 mL) were collected via femoral vein at 0 min (pre-dose), 5 min, 15 min, 30 min, 45 min, 1 hr, 1.5 hr, 2 hr, 3 hr, 4 hr, and 6 hr post-dose. Blood was stored on ice prior to centrifugation to obtain plasma samples. Centrifugation took place within 15 minutes of blood collection to harvest plasma (maximum volume). The plasma was decanted immediately and frozen/stored at −20° C. until analysis.

Plasma samples were analyzed by LC-MS/MS for the presence of the administered compound and its corresponding M1 metabolite:

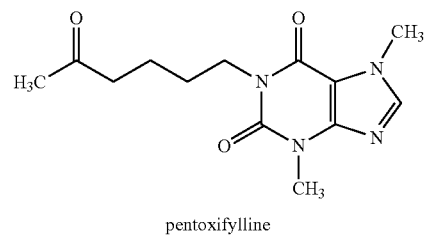
pentoxifylline

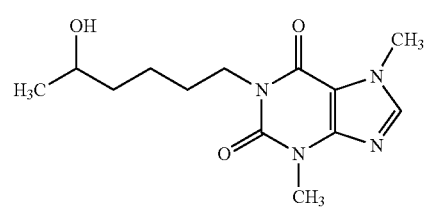
M1

-continued

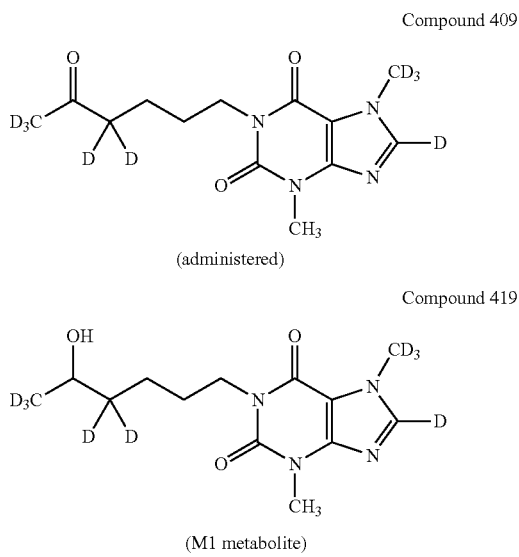

Compound 409 (administered)

Compound 419 (M1 metabolite)

Figure 1B:
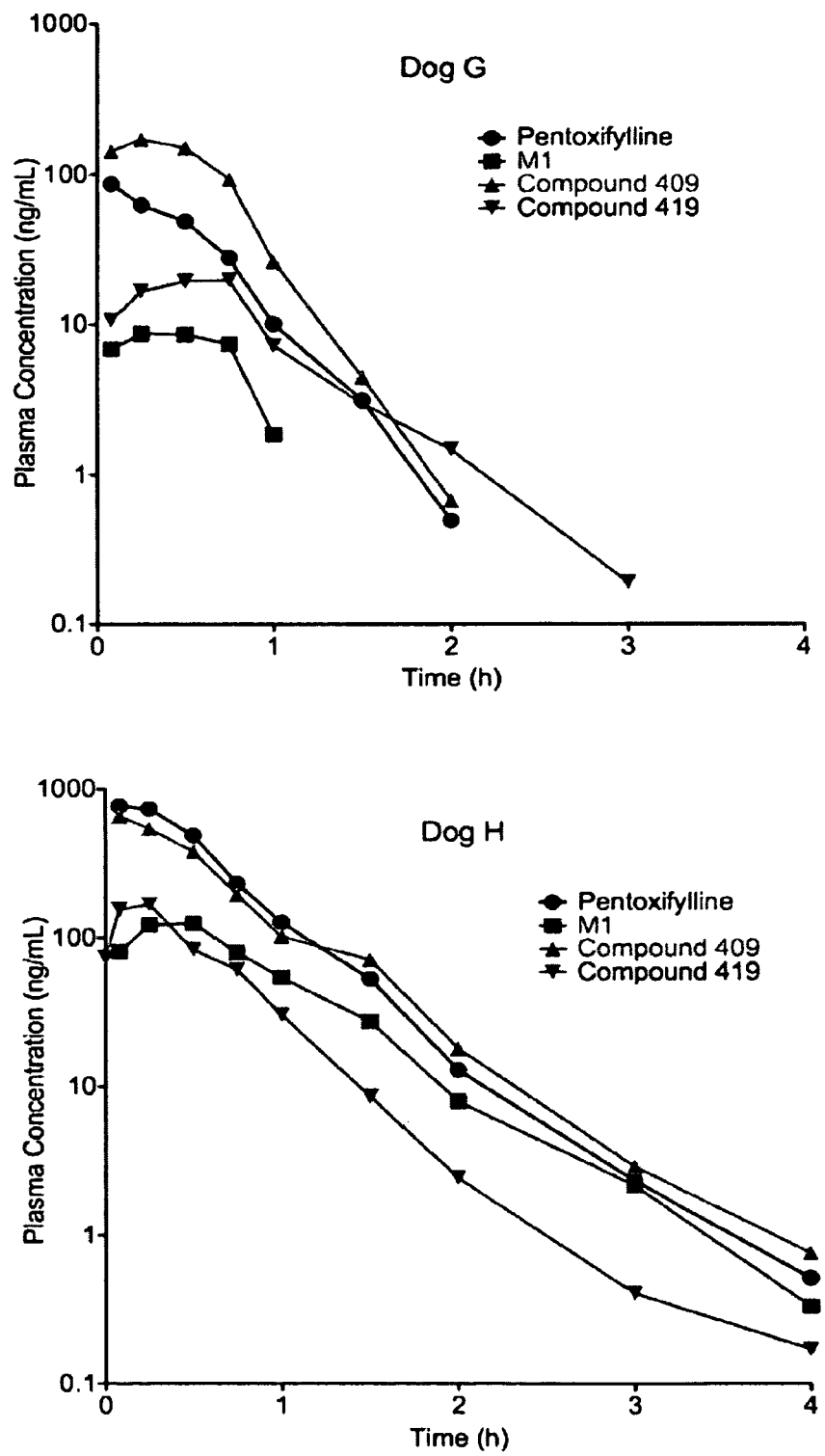

The results from each of the four dogs are shown in FIGS. 1A and 1B. The results from one of the four dogs (Dog H, FIG. 1b) were inconsistent with that of the other three. That dog showed a 10-fold higher plasma concentration of each of the administered compounds and their respective metabolites at 5 minutes post-administration. In addition, that dog did not show a characteristic increase in plasma concentration of the administered compounds between 5 and 15 minutes post-administration. It was concluded that this dog was most likely improperly gavaged and that the compounds were probably administered through the trachea, rather than into the GI tract as would have been desired. Accordingly, the data from this dog was excluded from the analyses. The summary analysis of the three remaining dogs is shown in Table 9.

TABLE 9

Plasma Levels of Compound 409 vs Pentoxifylline in Dogs (Example 15b)

| Compound | Ave. $C_{max}$ (ng/mL) | Ave. AUC (hr*ng/mL) |
|---|---|---|
| Pentoxifylline | 166 | 69 |
| Compound 409[a] | 299 | 136 |
| % Difference[b] | +80% | +97% |

[a]The dosing concentration of compound 409 was 10% higher than that for pentoxifylline and thus the numbers reported here reflect the adjustment for that 10% increase.
[b]% Difference = [(deuterated species) − (nondeuterated species)](100)/(nondeuterated species)

As can be seen in Table 9, higher levels of Compound 409 in terms of $C_{max}$ and AUC were observed when compared to pentoxifylline co-dosed at the same level. FIG. 1 demonstrates that Compound 409 was more slowly cleared from the plasma than pentoxifylline in the three dogs that were orally dosed. FIGS. 1a and 1b demonstrate that Compound 409 was more slowly cleared from the plasma than pentoxifylline in the three dogs that were orally dosed. FIGS. 1a and 1b also show that overall systemic exposure to Compound 419 (the deuterated M1 metabolite of 409) following dosing of Compound 409 was greater than that of the M1 metabolite following dosing of pentoxifylline.

Example 15c

Evaluation of Pharmacokinetics in Dogs Following Oral Administration. Comparison of Compound 413 and Pentoxifylline This study was similar to those described in Examples 15a and 15b, except that Compound 413 was evaluated. Four male beagle dogs were orally dosed by gavage with a mixture containing 2 mg/mL each of pentoxifylline and Compound 413 in saline. Blood samples were taken as in Example 15b.

TABLE 10

Plasma Levels of Compound 413 vs Pentoxifylline in Dogs (Example 15c)

| Compound | Ave. Cmax (ng/mL) | Ave. AUC (hr*ng/mL) |
|---|---|---|
| Pentoxifylline | 369 | 238 |
| Compound 413 | 542 | 415 |
| % Difference[a] | +47% | +74% |

[a]% Difference = [(deuterated species) − (nondeuterated species)](100)/(nondeuterated species)

The results of this study are summarized in Table 10 above. The table depicts the plasma levels of Compound 413 compared to pentoxifylline following oral dosing. Higher levels of Compound 413 in terms of $C_{max}$ and AUC were observed when compared to pentoxifylline co-dosed at the same level.

Example 16

Evaluation of the Stability of Compounds in Rat Whole Blood. Comparison of Compounds 409, 435(S), 435(R) and Pentoxifylline and its M-1 Metabolites This study was performed to evaluate the stability of the title compounds in rat whole blood. Because the ketone (or keto-compound; either pentoxifylline or 409) and its corresponding M-1 alcohol metabolite interconvert, levels of these components were measured after either the keto-compound was added to the blood or the M-1 was added. In other words, in some tests the keto-compound was the starting test compound and in other tests an M-1 metabolite was the starting test compound.

Fresh rat whole blood was obtained from ViviSource Laboratories, Waltham, Mass. Stock solutions (7.5 millimolar (mM)) of test compounds were prepared in dimethyl sulfoxide (DMSO). The 7.5 mM stock solutions were diluted to 500 micromolar (μM) in acetonitrile (ACN). To 990 microliters (μL) of blood pre-warmed to 37° C. for 7 minutes was added 10 μL of 500 μM test compound to a final concentration of 5 μM. The test compounds were pentoxifylline, (S)-M1 metabolite of pentoxifylline, (R)-M1 metabolite of pentoxifylline, Compound 409, Compound 435(S), and Compound 435(R). The latter two test compounds are deuterated (S)-M1 and (R)-M1 metabolites, respectively, of Compound 409. The reaction mixture was incubated at 37° C. Aliquots (50 μL) were removed at 0 min, 5 min, 15 min, 30 min, 1 hour and 2 hours following the addition of test compound and added to 96-well plates containing 150 μL of ice cold acetonitrile with an internal standard to stop the reaction. The plates were stored at −20° C. for 20 minutes after which 100 μL of 50% acetonitrile/water was added to the wells of the plate prior to centrifugation to pellet precipitated proteins. A 200-4 aliquot of each supernatant was transferred to another 96-well plate and analyzed by LC-MS/MS using an Applied Bio-systems API 4000 mass spectrometer for amounts of the administered compound and its specific metabolite listed in Table 11 below.

TABLE 11

Compound-Metabolite Pairs Analyzed in Rat Whole Blood. (Experiments 16 and 17)

| Experiment Pair | Compound Incubated with Blood | Metabolite Analyzed |
| --- | --- | --- |
| A | pentoxifylline | (S)-M1[a] |
| B | Compound 409 | Compound 419(S)[a] |
| C | (S)-M1 | pentoxifylline |
| D | Compound 435(S) | Compound 409 |
| E | (R)-M1 | pentoxifylline |
| F | Compound 435(R) | Compound 409 |

[a]Mass observed via LC-MS/MS. Stereochemistry presumed to be ≥95% (S) based on published pentoxifylline metabolism reports.

Figure 2:
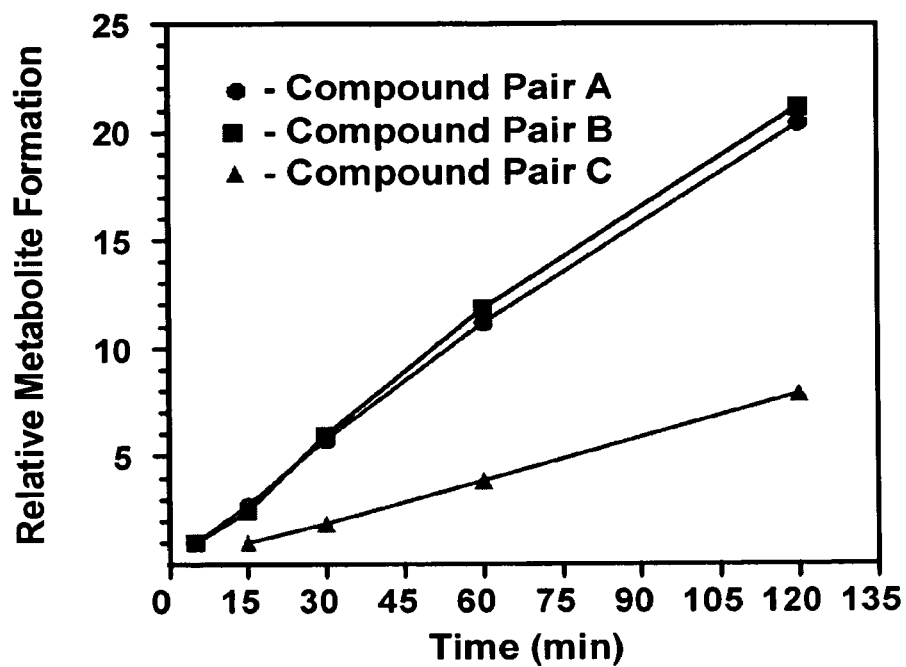
FIG. 2 depicts the time course of the production of the specific metabolites measured in FIG. 3 following incubation of various compounds of this invention, pentoxifylline, (S)-M1 and (R)-M1 with rat whole blood.
Figure 3:
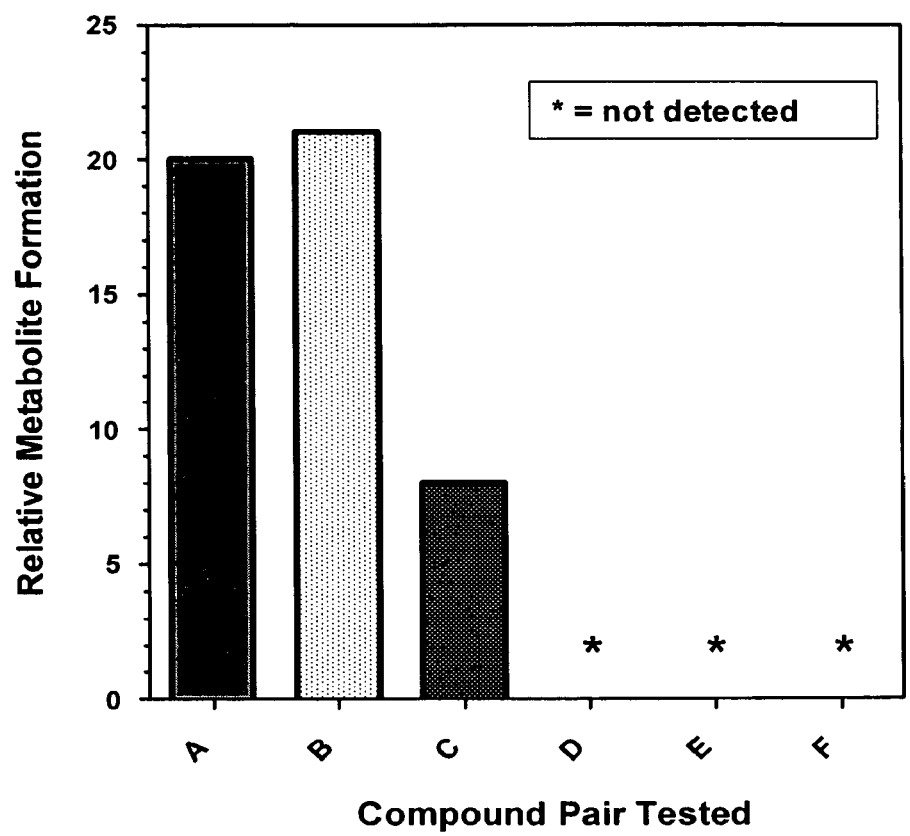
FIG. 3 depicts the relative amount of specific metabolites produced following incubation of various compounds of this invention, pentoxifylline, (S)-M1 and (R)-M1 with rat whole blood.

The results of this study are depicted in FIGS. 2 and 3. The time course of metabolite formation is shown in FIG. 2. The relative amount of metabolite formed, as shown in FIG. 3, was calculated based on the amount present at 2 hr relative to the earliest time point at which it was detected in the incubation mixture, 5 minutes for A and B, and 15 minutes for C.

As seen in FIG. 3, after approximately 2 hours the amount of (5)-M1 formed in rat whole blood incubated with pentoxifylline (FIG. 3, column A) was similar to the amount of Compound 419(S) formed in rat whole blood incubated with Compound 409 (FIG. 3, column B). Thus, the deuterium substitution in Compound 409 had no discernable effect on the relative level of deuterated (S)-M1 metabolite (Compound 419(S)) formed as compared to the relative level of undeuterated (S)-M1 formed from undeuterated pentoxifylline.

For the reverse reaction, (5)-M1 to the keto-compound, deuteration did have a significant effect. Column C in FIG. 3 shows an appreciable amount of pentoxifylline present after addition of (S)-M1. By contrast, 2 hours after addition of Compound 435 (S), Compound 409 was not detected (FIG. 3, column D). Under these conditions, the deuterium substitution in Compound 435 (S) impedes the conversion of this compound to the corresponding ketone. Such an effect is particularly beneficial for enhancing the plasma levels of the desired M-1 metabolite.

No metabolism of (R)-M1 to pentoxifylline was detected in this assay. Similarly, Compound 409 was not detected after addition of Compound 435 (R) to the rat blood. Thus, no conclusions could be made concerning the effect of deuteration on the conversion of (R)-M1 to pentoxifylline. FIG. 2 shows the time course of the specific metabolite produced during incubation of the administered compound with rat whole blood.

Example 17

Evaluation of Compound Stability in Human Liver Microsomes. Comparison of Compounds 409, 435(S), 435(R) and Pentoxifylline Example 17 is similar to Example 16 in design, except that human liver microsomes were used instead of rat whole blood to study the metabolism of the compounds. Table 11 above shows each pair of test compound and metabolite that was analyzed in this Example 17.

Human liver microsomes (20 mg/mL) were obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) were purchased from Sigma-Aldrich.

Stock solutions containing 7.5 mM of test compounds (pentoxifylline, (S)-M1 metabolite, (R)-M1 metabolite, Compound 409, Compound 435(S), and Compound 435(R)) were prepared in DMSO. The 7.5-mM stock solutions were diluted to 250 μM in acetonitrile (ACN). The human liver microsomes were diluted to 2.5 mg/mL in 0.1 M potassium phosphate buffer, pH 7.4, containing 3 mM $MgCl_2$. The diluted microsomes were added to wells of a 96-well deep-well polypropylene plate in triplicate. 10 μL of the 250 μM test compound was added to the microsomes and the mixture was pre-warmed to 37° C. for 10 minutes. Reactions were initiated by addition of pre-warmed NADPH solution. The final reaction volume was 0.5 mL and contained 2.0 mg/mL human liver microsomes, 5 μM test compound, and 2 mM NADPH in 0.1M potassium phosphate buffer, pH 7.4, and 3 mM $MgCl_2$. The reaction mixtures were incubated at 37° C., and 50-μL aliquots were removed at 0, 5, 10, 20, and 30 minutes and added to shallow-well 96-well plates which contained 50 μL of ice-cold acetonitrile with internal standard to stop the reactions. The plates were stored at 4° C. for 20 minutes after which 100 μL of water was added to the wells of the plate before centrifugation to pellet precipitated proteins. Supernatants were transferred to another 96-well plate and analyzed for the amount of the administered compound and its specific metabolite (listed in Table 11 above) by LC-MS/MS using an Applied Bio-systems API 4000 mass spectrometer.

Figure 4:
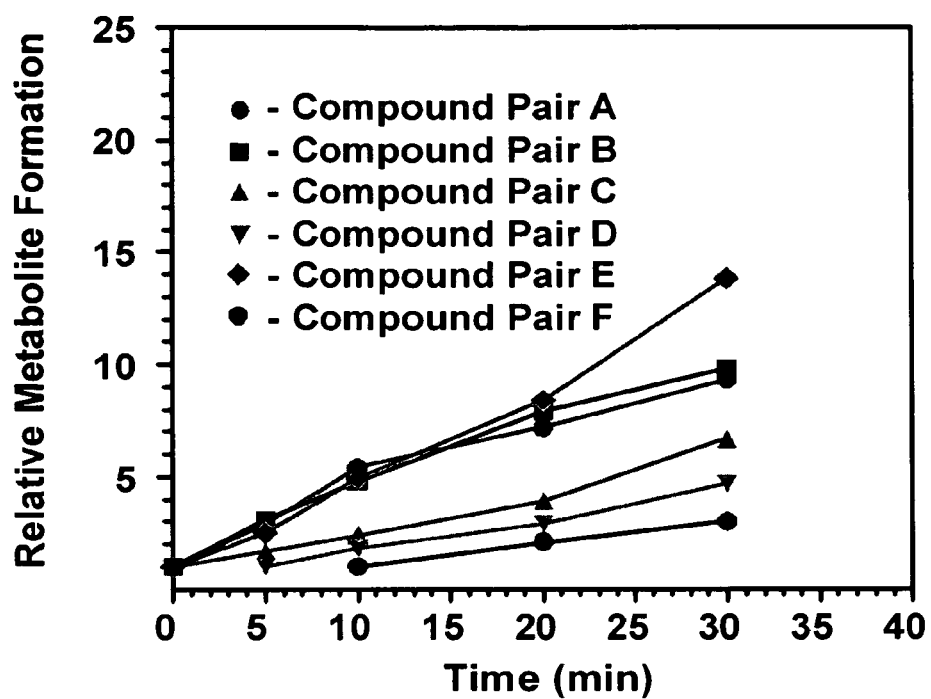
FIG. 4 depicts the time course of the production of the specific metabolites measured in FIG. 5 following incubation of various compounds of this invention, pentoxifylline, (S)-M1 and (R)-M1 with human liver microsomes.
Figure 5:
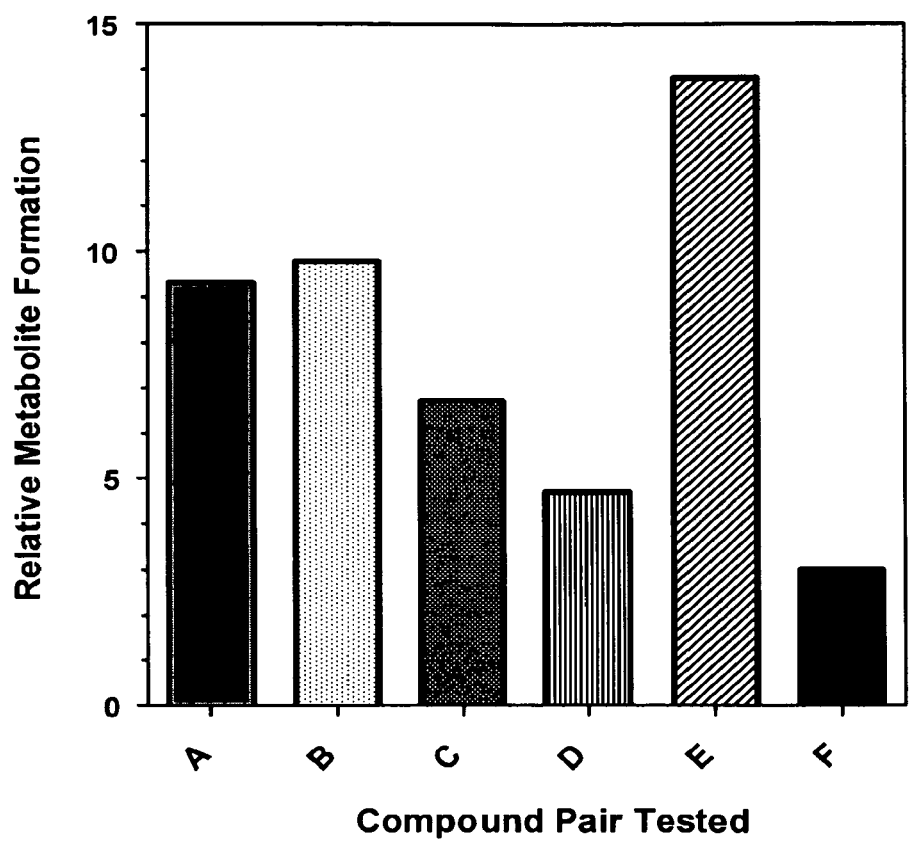
FIG. 5 depicts the relative amount of specific metabolites produced following incubation of various compounds of this invention, pentoxifylline, (S)-M1 and (R)-M1 with human liver microsomes

The results of this study are depicted in FIGS. 4 and 5. The time course of metabolite formation is shown in FIG. 4. The relative amount of metabolite formed, as shown in FIG. 5, was calculated based on the amount present at 30 minutes relative to the earliest time point at which it was detected in the incubation mixture, 0 minutes for A, B, C and E, 5 minutes for D, and 10 minutes for F. The amount of (S)-M1 formed in human liver microsomes incubated with pentoxifylline (FIG. 5, column A) after 30 minutes was similar to the amount Compound 419(5) formed in human liver microsomes incubated with Compound 409 (FIG. 5, column B). Thus, deuteration of pentoxifylline as embodied by Compound 409 had no discernable effect on the relative level of deuterated (S)-M1 metabolite (Compound 419(S)) formed as compared to the relative level of undeuterated (S)-M1 formed from undeuterated pentoxifylline. These results in human liver microsomes were consistent with those seen using rat whole blood.

For the reverse reaction, (S)-M1 to the keto-compound, deuteration did have an appreciable effect. Column C in FIG. 5 shows a significant amount of pentoxifylline present 30 minutes after addition of (S)-M1. By contrast, after addition of Compound 435 (S), the level of Compound 409 that was detected after 30 minutes was less than the level of (S)-M1 (FIG. 5, column D). Approximately 30% more pentoxifylline was produced from (S)-M1 than Compound 409 produced from Compound 435 (S). Under these conditions, the deuterium substitution in Compound 435 (S) impedes the conversion of this compound to the corresponding ketone. While deuterium had a greater effect in rat blood, the results are consistent.

A dramatic deuterium effect on the metabolism of (R)-M1 metabolite was observed in human liver microsomes. Deuteration of (R)-M1 (Compound 435(R)) reduced by almost 5-fold the amount of deuterated pentoxifylline formed (Compound 409) after 30 minute incubation with human liver microsomes as compared to the amount of undeuterated pentoxifylline formed from undeuterated (R)-M1 (comparing columns E and F in FIG. 5). FIG. 4 shows the time course of the specific metabolite produced during incubation of the administered compound with human liver microsomes.

Example 18

Pharmacokinetic Study in Rats of (S)-M1 and Compound 435(S) After Oral and Intravenous Dosing (S)-M1 and Compound 435(S) (a deuterated form of (S)-M1) were separately dissolved in saline at a concentration of 10 mg/mL. A 1:1 mixture of the two compounds was then prepared containing a final concentration of 5 mg/mL of each compound, which was used for intravenous administration. For oral administration the mixture was further diluted in saline to a final concentration of 1 mg/mL for each compound.

Three male Sprague-Dawley rats were used in each of the oral and intravenous studies. Animals were fasted overnight prior to administration of compounds. Intravenous administration was achieved by bolus injection of a single 5 mg/kg dose of the 1:1 combination into the cannulated jugular vein of the rats. Cannulation was achieved the day prior to dosing on rats that had been placed under anesthesia using ketamine (IM 30 mg/kg). Oral administration was achieved by oral gavage of a single 5 mg/kg dose. Blood samples (250 µL) were collected from the dosed rats at various times post-dosing (2 min, 5 min, 10 min, 20 min, 30 min, 1 hr, 2 hr, 3 hr, 4 hr, 5 hr, 6 hr) by retro-orbital sampling of the rats temporarily anesthetized with isoflurane. Blood samples were placed in tubes containing $K_2$-EDTA and stored on ice until centrifuged. Within 30 minutes of collection, plasma was isolated by centrifugation. A 100-µL aliquot was removed, mixed with 200 µL of acetonitrile and stored at −20° C. until further analysis by LC-MS/MS using an Applied Bio-systems API 4000 mass spectrometer.

Samples were analyzed for the presence of the administered compound, the corresponding ketone (pentoxifylline and Compound 409) and the corresponding M5 metabolite. Samples (10 µL) were injected into a Zorbax SB-C8 (Rapid Resolution) column (2.1×30 mm, 3.5 µm). The initial mobile phase condition was 100% A (10 mM ammonium acetate in water) and 0% B (methanol) with a flow rate at 0.5 mL/min. Mobile phase B was allowed to reach 55% in 3 minutes and from 55% to 90% in 1 minute before ramping back to 0% in another minute. The overall run time was 5 minutes. For pentoxifylline and its M1 and M5 metabolites, the precursor/product ion pairs were set at m/z 281/193 (M1), m/z 279/181 (pentoxifylline), and m/z 267/221 (M5).

For Compound 435(S) and Compound 409 more than one ion pair was set up for to detect species that arose from loss of deuterium. It was found that some degree of deuterium loss occurs on those compounds of the invention, such as Compound 409, which have deuterium on the side chain at positions adjacent to the carbonyl carbon. This loss of deuterium appears to occur both in vivo and ex vivo by an unknown mechanism. The addition of acetonitrile to serum samples was used to stop any additional ex vivo deuterium loss prior to analysis. Typically, no more than 2 deuterium atoms were replaced by hydrogen. For Compound 435(S), there is a deuterium at the methinyl position which was lost upon oxidation to the keto-compound 409. Reduction of 409 to an M1 metabolite introduced a proton at the methinyl position. When serum from animals dosed with 435(S) were analyzed to quantitate administered compound and metabolites, compound species were included with one and two less side chain deuteriums in the total amounts (referred to hereinafter as the "-1D" and the "-2D" species). Thus, for Compound 435(S) and Compound 409 separate ion pairs were set up to detect the compound and its corresponding -1D and -2D species. For Compound 435(S) three ion pairs were detected: m/z 291/197, 290/197, and 189/197. For Compound 409 ion pairs of m/z 288/186, 287/186 and 286/186 were monitored. Inclusion of -1D and -2D species in the measurements of Compound 409 and Compound 435(S) more accurately quantitates the total active species and is reasonable based on what is known about the metabolism and activities of pentoxifylline and its M-1 metabolites. Increased plasma exposure to Compound 409 or any M-1 metabolites of 409 would be desirable. This includes the -1D and -2D species.

For the corresponding deuterated M5 metabolite (M5a):

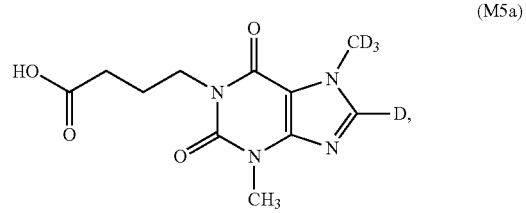

(M5a)

which has no deuterium on its acid side chain, only one ion pair was used at m/z 271/225. The internal standard for the analysis was indiplon.

TABLE 12

Pharmacokinetic Results After Oral Administration of 435(S) and (S)-M1 in Rats.

| Compound(s) Measured[a] | $AUC_{0-\infty}$ (hr*ng/mL) | $C_{max}$ (ng/mL) |
| --- | --- | --- |
| 435(S) | 4507 ± 1015 | 4105 ± 964 |
| (S)-M1 | 1628 ± 272 | 1570 ± 249 |
| % Difference[b] | +177% | +162% |
| 435(S) + 409 | 13464 ± 3502 | 15647 ± 7421 |
| (S)-M1 + pentoxifylline | 4632 ± 437 | 5032 ± 630 |
| % Difference[b] | +191% | +212% |
| Deuterated M5 (M5a) | 1924 ± 183 | |
| M5 | 2985 ± 601 | |
| % Difference[b] | −36% | |

[a]Mass observed via LC-MS/MS. Stereochemistry presumed to be ≥95% (S) based on published pentoxifylline metabolism reports.
[b]% Difference = [(deuterated species) − (nondeuterated species)](100)/(nondeuterated species)

The results of the oral administration in rats are shown in Table 12. The deuterated Compound 435(S) demonstrated a significantly higher $AUC_{0-\infty}$ and $C_{max}$ than its undeuterated counterpart (S)-M1. Because there is a significant serum interconversion between (S)-M1 and pentoxifylline and both species are therapeutically active, we also quantitated $AUC_{0-\infty}$ and $C_{max}$ for (S)-M1 together with pentoxifylline, and for Compound 435(S) together with Compound 409. Compound 435(S) together with Compound 409 demonstrated a significantly higher $AUC_{0-\infty}$ and $C_{max}$ than did (S)-M1 together with pentoxifylline after the oral administration of (S)-M1 and 435(S) respectively.

The $AUC_{0-\infty}$ was also measured for the M-5 and M5a metabolites arising from the oral administration of (S)-M1 and 435(S), respectively. The M-5 metabolite may be associated with toxicity in certain patients and is considered undesirable. Table 12 shows that oral administration of Compound 435(S) provides considerably less M5a compared to the level of M5 obtained after administration of non-deuterated (S)-M1. The ratio of active species to M5 metabolite was much more favorable for the deuterated compounds than for the non-deuterated compounds. The ratio of (Compound 435(S)+Compound 409) to M5a was 7.0, which was much better than the ratio of 1.6 for ((S)-M1+pentoxifylline) to M5.

TABLE 13

Pharmacokinetic Results After Intravenous Administration in Rats.

| Compound(s) Measured[a] | $AUC_{0-\infty}$ (hr*ng/mL) |
|---|---|
| 435(S) | 7127 ± 816 |
| (S)-M1 | 3390 ± 302 |
| % Difference[b] | +110% |
| 435(S) + 409 | 11247 ± 1326 |
| (S)-M1 + pentoxifylline | 6280 ± 460 |
| % Difference[b] | +79% |
| Deuterated M5 (M5a) | 1522 ± 530 |
| M5 | 1795 ± 521 |
| % Difference[b] | −15% |

[a]Mass observed via LC-MS/MS. Stereochemistry presumed to be ≥95% (S) based on published pentoxifylline metabolism reports.
[b]% Difference = [(deuterated species) − (nondeuterated species)](100)/(nondeuterated species)

Table 13 shows the results following intravenous administration in rats. The results for intravenous administration were similar to those for oral administration. Compound 435(S) had an average $AUC_{0-\infty}$ that was 110% greater than its undeuterated counterpart (S)-M1 after intravenous administration. Compound 435(S) together with Compound 409 had an average $AUC_{0-\infty}$ that was 79% greater than (S)-M1 together with pentoxifylline after intravenous administration. Intravenous administration of Compound 435(S) provides an amount of M5a metabolite that is 15% less than the amount of M5 metabolite than is provided by intravenous administration of (S)-M1. The ratio of active species to the corresponding M5 metabolite in rats that were intravenously administered Compound 435(S) was 7.4 as compared to 3.5 for rats that were intravenously administered (S)-M1.

Example 19

Pharmacokinetic Study of Pentoxifylline and Compound 435(S) in Chimps after Oral and Intravenous Dosing Pentoxifylline and Compound 435(S) were separately dissolved in warm (65° C.) saline at a concentration at 10 mg/mL. A 1:1 mixture of the two compounds was then prepared containing a final concentration of 5 mg/mL of each compound and the mixture was then sterile filtered through a 0.2-μm filter.

Two chimps (one male and one female) were used in each of the oral and intravenous studies. Animals were fasted overnight prior to administration of compounds. All animals were sedated with ketamine (approximately 10 mg/kg) and/or telazol (approximately 5 mg/kg) prior to dosing. Intravenous administration was achieved by IV infusion of 75 mg of each compound (15 mL total dosing solution) over 10 minutes. Oral administration was achieved by oral gavage of a single 75 mg dose of each compound (15 mL total dosing solution). Blood samples (6 mL) were collected from the dosed chimps at various times prior to and after dosing. For intravenous administrations blood samples were collected at 0 min (preinfusion), 5 min, 9.5 min (immediately before the end of the infusion), then 6, 15, 30 and 45 min, and 1, 2, 4, 6, 8, 10 and 12 hr after the infusion is stopped. For oral administrations, blood samples were collected at 0 min (predose), 15 and 30 min, and 1, 1.5, 2, 4, 6, 8, 10 and 12 hr postdose.

Blood samples were placed in tubes containing sodium heparin, mixed and stored on ice until centrifuged. Within 30 minutes of collection, plasma was isolated by centrifuging the blood samples and removing an aliquot (200 μL) of the resulting plasma. Each 200-μL aliquot of plasma was mixed with 400 μL acetonitrile and stored at −70° C. until further analysis by LC-MS/MS using an Applied Bio-systems API 4000 mass spectrometer.

The analysis of all samples by LC-MS/MS was performed as described above for the rat plasma samples in Example 18.

TABLE 14

Pharmacokinetic Results Following Oral Administration in Chimps.

| | $AUC_{0-\infty}$ (hr*ng/mL) | |
|---|---|---|
| Compound(s) Measured[a] | Male | Female |
| 435(S) | 829 | 672 |
| (S)-M1 | 300 | 301 |
| % Difference[b] | +176% | +123% |
| 435(S) + 409 | 1097 | 1277 |
| (S)-M1 + pentoxifylline | 414 | 525 |
| % Difference[b] | +165% | +143% |
| Deuterated M5 (M5a) | 462 | 606 |
| M5 | 1456 | 1868 |
| % Difference[b] | −68% | −68% |

[a]Mass observed via LC-MS/MS. Stereochemistry presumed to be ≥95% (S) based on published pentoxifylline metabolism reports.
[b]% Difference = [(deuterated species) − (nondeuterated species)](100)/(nondeuterated species)

Table 14 shows the results of oral administration of 435(S) and pentoxifylline in chimps. Following oral administration of a 1:1 combination of Compound 435(S) and pentoxifylline, both Compound 435(S) and its corresponding ketone Compound 409 demonstrated significantly higher average $AUC_{0-\infty}$ values than the corresponding undeuterated counterparts, (S)-M1 and pentoxifylline. The average $AUC_{0-\infty}$ for Compound 435(S) together with Compound 409 was significantly higher than the average $AUC_{0-\infty}$ for (S)-M1 together with pentoxifylline. In addition, the average $AUC_{0-\infty}$ for the undesired deuterated M-5 metabolite (M5a) was significantly lower than that of the undeuterated M-5. Finally, the ratio of active species to M5 metabolite for the deuterated compounds {(435(S)+409): (deuterated M5)} was approximately 8-fold higher than the corresponding ratio for the undeuterated species {((S)-M1+pentoxifylline): M5}.

TABLE 15

Pharmacokinetic Results Following Intravenous Administration in Chimps.

| | $AUC_{0-\infty}$ (hr*ng/mL) | |
|---|---|---|
| Compound(s) Measured[a] | Male | Female |
| 435(S) | 2522 | 1213 |
| (S)-M1 | 1559 | 657 |
| % Difference[b] | +61% | +84% |

TABLE 15-continued

Pharmacokinetic Results Following Intravenous Administration in Chimps.

| | AUC$_{0-\infty}$ (hr*ng/mL) | |
|---|---|---|
| Compound(s) Measured[a] | Male | Female |
| 435(S) + 409 | 3219 | 1607 |
| (S)-M1 + pentoxifylline | 2285 | 1018 |
| % Difference[b] | +40% | +57% |
| Deuterated M5 | 428 | 632 |
| M5 | 1195 | 1560 |
| % Difference[b] | −65% | −60% |

[a]Mass observed via LC-MS/MS. Stereochemistry presumed to be ≥95% (S) based on published pentoxifylline metabolism reports.
[b]% Difference = [(deuterated species) − (nondeuterated species)](100)/(nondeuterated species)

Table 15 shows the results of intravenous administration of 435(S) and pentoxifylline in chimps. The results following intravenous administration showed favorable differentiation of the deuterated compounds, though not as pronounced as those observed following oral administration. Compared to administration of pentoxifylline, the amounts of active species produced from the administration of Compound 435(S) were between 40 and 57% higher, while the amounts of M5 metabolite produced decreased by between 60 and 65%. The ratio of active species to M5 metabolite in chimps that were intravenously administered Compound 435(S) was approximately 4-fold higher than in chimps administered pentoxifylline.

The above results show that compounds of this invention provide significantly greater plasma exposure of desired active species than the corresponding non-deuterated compounds. Moreover, deuterium substitution in the present compounds was shown to reduce levels of the M5 metabolite, which may be associated with intolerability in renally-impaired patients.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A compound of Formula B:

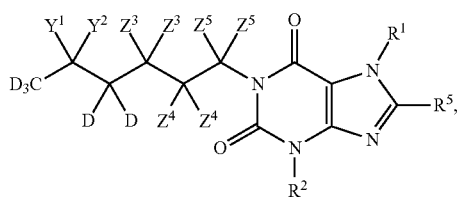

B or a pharmaceutically acceptable salt thereof, wherein:
 each of $R^1$ and $R^2$ is independently selected from —CH$_3$ and —CD$_3$;
 $R^5$ is hydrogen or deuterium;
 each $Z^3$ is hydrogen or deuterium;
 each $Z^4$ is hydrogen or deuterium;
 each $Z^5$ is hydrogen or deuterium;
 either (a) $Y^1$ is OH, and $Y^2$ is hydrogen or deuterium, or (b) $Y^1$ and $Y^2$ are taken together with the carbon to which they are attached to form C=O; and
 the deuterium incorporation at each designated deuterium atom is at least 90%.

2. The compound of claim 1, wherein $R^5$ is deuterium.

3. The compound of claim 2, wherein each $Z^3$, $Z^4$ and $Z^5$ is hydrogen and $R^1$ is —CD$_3$.

4. The compound of claim 1, wherein each $Z^3$, $Z^4$ and $Z^5$ is hydrogen.

5. The compound of claim 1, wherein each $Z^3$, $Z^4$ and $Z^5$ is deuterium.

6. The compound of claim 1, wherein $R^1$ and $R^2$ are each —CD$_3$.

7. The compound of claim 1, wherein $Y^1$ and $Y^2$ are taken together with the carbon to which they are attached to form C=O.

8. The compound of claim 1, wherein $Y^1$ and is OH, and $Y^2$ is hydrogen or deuterium.

9. A compound of Formula I:

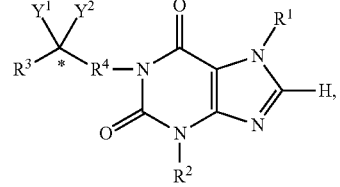

or a pharmaceutically acceptable salt thereof, selected from the following:

| Compound | $R^1$ | $R^2$ | $R^3$ | $R^4$ | $Y^1$ | $Y^2$ |
|---|---|---|---|---|---|---|
| 103 | CD$_3$ | CD$_3$ | CD$_3$ | (CD$_2$)$_4$ | taken together as =O | |
| 104 | CH$_3$ | CH$_3$ | CD$_3$ | (CD$_2$)$_4$ | taken together as =O | |
| 105 | CD$_3$ | CH$_3$ | CD$_3$ | (CD$_2$)$_4$ | taken together as =O | |
| 106 | CH$_3$ | CD$_3$ | CD$_3$ | (CD$_2$)$_4$ | taken together as =O | |
| 107 | CH$_3$ | CH$_3$ | CD$_3$ | †CD$_2$(CH$_2$)$_3$ | taken together as =O | |
| 108 | CH$_3$ | CH$_3$ | CD$_3$ | †(CD$_2$)$_3$CH$_2$ | taken together as =O | |
| 109 | CD$_3$ | CH$_3$ | CD$_3$ | †CD$_2$(CH$_2$)$_3$ | taken together as =O | |
| 110 | CD$_3$ | CH$_3$ | CD$_3$ | †(CD$_2$)$_3$CH$_2$ | taken together as =O | |
| 111 | CH$_3$ | CD$_3$ | CD$_3$ | †CD$_2$(CH$_2$)$_3$ | taken together as =O | |
| 112 | CH$_3$ | CD$_3$ | CD$_3$ | †(CD$_2$)$_3$CH$_2$ | taken together as =O | |
| 113 | CD$_3$ | CD$_3$ | CD$_3$ | †CD$_2$(CH$_2$)$_3$ | taken together as =O | |
| 114 | CD$_3$ | CD$_3$ | CD$_3$ | †(CD$_2$)$_3$CH$_2$ | taken together as =O | |
| 118 | CD$_3$ | CD$_3$ | CD$_3$ | †CD$_2$(CH$_2$)$_3$ | OH | H |
| 119 | CD$_3$ | CH$_3$ | CD$_3$ | †CD$_2$(CH$_2$)$_3$ | OH | H |
| 120 | CH$_3$ | CD$_3$ | CD$_3$ | †CD$_2$(CH$_2$)$_3$ | OH | H |
| 121 | CH$_3$ | CH$_3$ | CD$_3$ | †CD$_2$(CH$_2$)$_3$ | OH | H |
| 122 | CD$_3$ | CD$_3$ | CD$_3$ | (CD$_2$)$_4$ | OH | H |
| 123 | CD$_3$ | CH$_3$ | CD$_3$ | (CD$_2$)$_4$ | OH | H |
| 124 | CH$_3$ | CD$_3$ | CD$_3$ | (CD$_2$)$_4$ | OH | H |
| 125 | CH$_3$ | CH$_3$ | CD$_3$ | (CD$_2$)$_4$ | OH | H |
| 126 | CD$_3$ | CD$_3$ | CD$_3$ | †(CD$_2$)$_3$CH$_2$ | OH | H |
| 127 | CD$_3$ | CH$_3$ | CD$_3$ | †(CD$_2$)$_3$CH$_2$ | OH | H |
| 128 | CH$_3$ | CD$_3$ | CD$_3$ | †(CD$_2$)$_3$CH$_2$ | OH | H |
| 129 | CH$_3$ | CH$_3$ | CD$_3$ | †(CD$_2$)$_3$CH$_2$ | OH | H |
| 130 | CD$_3$ | CD$_3$ | CH$_3$ | (CH$_2$)$_4$ | OH | D |
| 131 | CD$_3$ | CH$_3$ | CH$_3$ | (CH$_2$)$_4$ | OH | D |
| 132 | CH$_3$ | CD$_3$ | CH$_3$ | (CH$_2$)$_4$ | OH | D |
| 133 | CH$_3$ | CH$_3$ | CH$_3$ | (CH$_2$)$_4$ | OH | D |
| 134 | CD$_3$ | CD$_3$ | CD$_3$ | †CD$_2$(CH$_2$)$_3$ | OH | D |
| 135 | CD$_3$ | CH$_3$ | CD$_3$ | †CD$_2$(CH$_2$)$_3$ | OH | D |
| 136 | CH$_3$ | CD$_3$ | CD$_3$ | †CD$_2$(CH$_2$)$_3$ | OH | D |
| 137 | CH$_3$ | CH$_3$ | CD$_3$ | †CD$_2$(CH$_2$)$_3$ | OH | D |
| 138 | CD$_3$ | CD$_3$ | CD$_3$ | (CD$_2$)$_4$ | OH | D |
| 139 | CD$_3$ | CH$_3$ | CD$_3$ | (CD$_2$)$_4$ | OH | D |
| 140 | CH$_3$ | CD$_3$ | CD$_3$ | (CD$_2$)$_4$ | OH | D |
| 141 | CH$_3$ | CH$_3$ | CD$_3$ | (CD$_2$)$_4$ | OH | D |
| 142 | CD$_3$ | CD$_3$ | CD$_3$ | †(CD$_2$)$_3$CH$_2$ | OH | D |

-continued

| Compound | R¹ | R² | R³ | R⁴ | Y¹ | Y² |
|---|---|---|---|---|---|---|
| 143 | CD₃ | CH₃ | CD₃ | †(CD₂)₃CH₂ | OH | D |
| 144 | CH₃ | CD₃ | CD₃ | †(CD₂)₃CH₂ | OH | D |
| 145 | CH₃ | CH₃ | CD₃ | †(CD₂)₃CH₂ | OH | D; | wherein the deuterium incorporation at each designated deuterium atom is at least 90%; and wherein "†" represents the portion of the R⁴ moiety bound to C(Y¹)(Y²) in the compound.

10. A compound of Formula A:

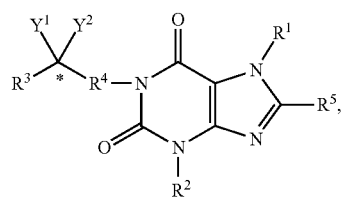

or a pharmaceutically acceptable salt thereof, selected from the following:

| Compound | R¹ | R² | R³ | R⁴ | R⁵ | Y¹ | Y² |
|---|---|---|---|---|---|---|---|
| 400 | CD₃ | CH₃ | CH₃ | (CH₂)₄ | D | Taken together as =O | |
| 401 | CD₃ | CD₃ | CH₃ | (CH₂)₄ | D | Taken together as =O | |
| 402 | CH₃ | CD₃ | CH₃ | (CH₂)₄ | D | Taken together as =O | |
| 403 | CD₃ | CD₃ | CD₃ | (CH₂)₄ | D | Taken together as =O | |
| 404 | CH₃ | CH₃ | CD₃ | (CD₂)₄ | D | Taken together as =O | |
| 405 | CD₃ | CH₃ | CD₃ | (CD₂)₄ | D | Taken together as =O | |
| 406 | CH₃ | CD₃ | CD₃ | (CD₂)₄ | D | Taken together as =O | |
| 407 | CH₃ | CH₃ | CD₃ | †CD₂(CH₂)₃ | D | Taken together as =O | |
| 408 | CH₃ | CH₃ | CD₃ | †(CD₂)₃CH₂ | D | Taken together as =O | |
| 409 | CD₃ | CH₃ | CD₃ | †CD₂(CH₂)₃ | D | Taken together as =O | |
| 410 | CD₃ | CH₃ | CD₃ | †(CD₂)₃CH₂ | D | Taken together as =O | |
| 411 | CH₃ | CD₃ | CD₃ | †CD₂(CH₂)₃ | D | Taken together as =O | |
| 412 | CH₃ | CD₃ | CD₃ | †(CD₂)₃CH₂ | D | Taken together as =O | |
| 413 | CD₃ | CD₃ | CD₃ | †CD₂(CH₂)₃ | D | Taken together as =O | |
| 414 | CD₃ | CD₃ | CD₃ | †(CD₂)₃CH₂ | D | Taken together as =O | |
| 415 | CD₃ | CD₃ | CH₃ | (CH₂)₄ | D | OH | H |
| 416 | CD₃ | CH₃ | CH₃ | (CH₂)₄ | D | OH | H |
| 417 | CH₃ | CD₃ | CH₃ | (CH₂)₄ | D | OH | H |
| 418 | CD₃ | CD₃ | CD₃ | †CD₂(CH₂)₃ | D | OH | H |
| 419 | CD₃ | CH₃ | CD₃ | †CD₂(CH₂)₃ | D | OH | H |
| 420 | CH₃ | CD₃ | CD₃ | †CD₂(CH₂)₃ | D | OH | H |
| 421 | CH₃ | CH₃ | CD₃ | †CD₂(CH₂)₃ | D | OH | H |
| 422 | CD₃ | CD₃ | CD₃ | (CD₂)₄ | D | OH | H |
| 423 | CD₃ | CH₃ | CD₃ | (CD₂)₄ | D | OH | H |
| 424 | CH₃ | CD₃ | CD₃ | (CD₂)₄ | D | OH | H |
| 425 | CH₃ | CH₃ | CD₃ | (CD₂)₄ | D | OH | H |
| 426 | CD₃ | CD₃ | CD₃ | †(CD₂)₃CH₂ | D | OH | H |
| 427 | CD₃ | CH₃ | CD₃ | †(CD₂)₃CH₂ | D | OH | H |
| 428 | CH₃ | CD₃ | CD₃ | †(CD₂)₃CH₂ | D | OH | H |
| 429 | CH₃ | CH₃ | CD₃ | †(CD₂)₃CH₂ | D | OH | H |
| 430 | CD₃ | CD₃ | CH₃ | (CH₂)₄ | D | OH | D |
| 431 | CD₃ | CH₃ | CH₃ | (CH₂)₄ | D | OH | D |
| 432 | CH₃ | CD₃ | CH₃ | (CH₂)₄ | D | OH | D |
| 433 | CH₃ | CH₃ | CH₃ | (CH₂)₄ | D | OH | D |
| 434 | CD₃ | CD₃ | CD₃ | †CD₂(CH₂)₃ | D | OH | D |
| 435 | CD₃ | CH₃ | CD₃ | †CD₂(CH₂)₃ | D | OH | D |
| 436 | CH₃ | CD₃ | CD₃ | †CD₂(CH₂)₃ | D | OH | D |
| 437 | CH₃ | CH₃ | CD₃ | †CD₂(CH₂)₃ | D | OH | D |
| 438 | CD₃ | CD₃ | CD₃ | (CD₂)₄ | D | OH | D |
| 439 | CD₃ | CH₃ | CD₃ | (CD₂)₄ | D | OH | D |
| 440 | CH₃ | CD₃ | CD₃ | (CD₂)₄ | D | OH | D |
| 441 | CH₃ | CH₃ | CD₃ | (CD₂)₄ | D | OH | D |
| 442 | CD₃ | CD₃ | CD₃ | †(CD₂)₃CH₂ | D | OH | D |
| 443 | CD₃ | CH₃ | CD₃ | †(CD₂)₃CH₂ | D | OH | D |
| 444 | CH₃ | CD₃ | CD₃ | †(CD₂)₃CH₂ | D | OH | D |
| 445 | CH₃ | CH₃ | CD₃ | †(CD₂)₃CH₂ | D | OH | D. | wherein the deuterium incorporation at each designated deuterium atom is at least 90%; and wherein "†" represents the portion of the R⁴ moiety bound to C(Y¹)(Y²) in the compound.

11. A compound selected from any one of the following:

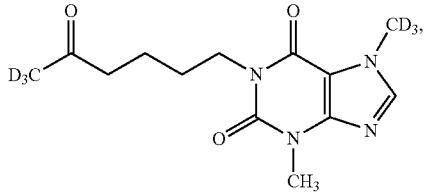

99

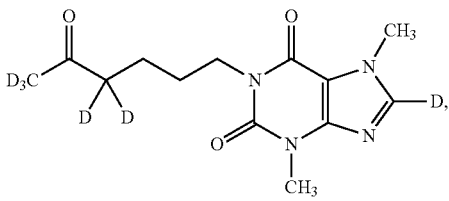

407

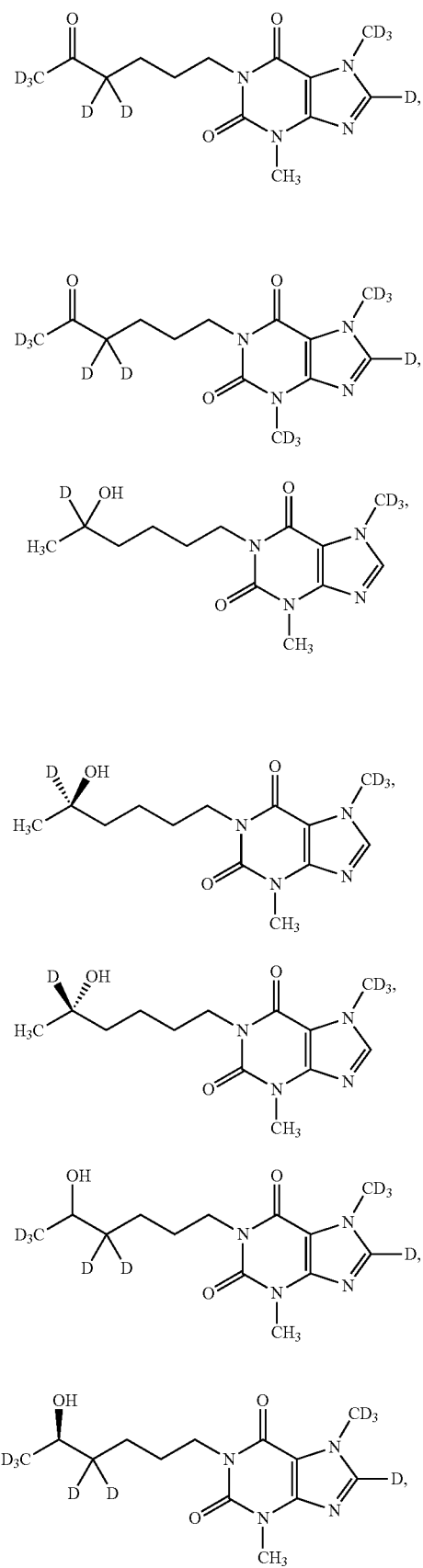
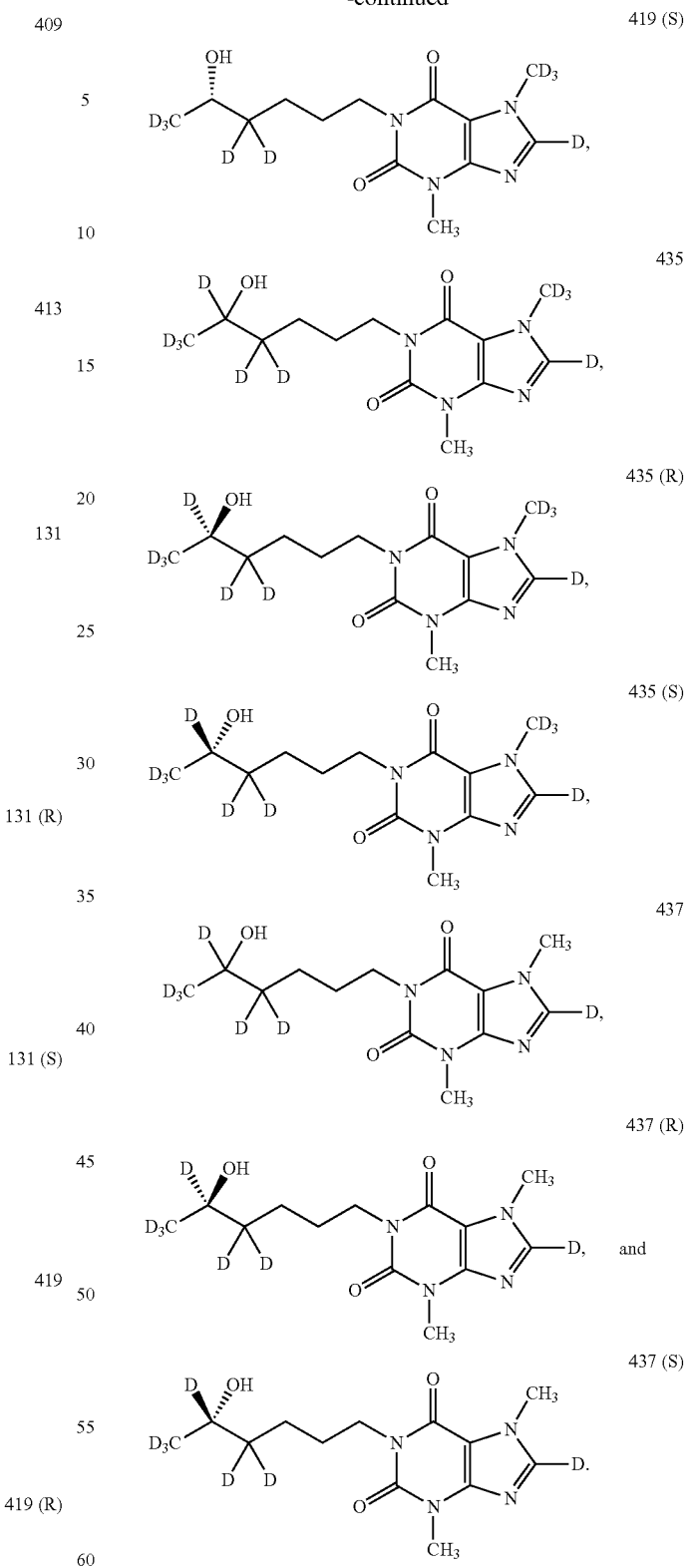
or a pharmaceutically acceptable salt of any of the foregoing; wherein the deuterium incorporation at each designated deuterium atom is at least 90%.
12. The compound of claim 1, wherein any atom not designated as deuterium is present at its natural isotopic abundance.

13. A pharmaceutical composition comprising a compound of claim 1 and a pharmaceutically acceptable carrier.

14. A method of treating a disease or condition in a patient in need thereof, comprising administering to the patient an effective amount of a composition of claim 13, wherein the disease is selected from diabetic nephropathy, hypertensive nephropathy or intermittent claudication on the basis of chronic occlusive arterial disease of the limbs.

15. A method of treating chronic kidney disease in a patient in need thereof, comprising administering to the patient an effective amount of a composition of claim 13.

16. The method of claim 15 wherein the chronic kidney disease is glomerulonephritis, focal segmental glomerulosclerosis, nephrotic syndrome, reflux uropathy, or polycystic kidney disease.

17. A method of treating chronic disease of the liver in a patient in need thereof, comprising administering to the patient an effective amount of a composition of claim 13.

18. The method of claim 17 wherein the chronic disease of the liver is nonalcoholic steatohepatitis, fatty liver degeneration or other diet-induced high fat or alcohol-induced tissue-degenerative conditions, cirrhosis, liver failure, or alcoholic hepatitis.

19. A method of treating a diabetes-related disease or condition in a patient in need thereof, comprising administering to the patient an effective amount of a composition of claim 13, wherein the disease or condition is selected from insulin resistance, retinopathy, diabetic ulcers, radiation-associated necrosis, acute kidney failure or drug-induced nephrotoxicity.

20. A method of treating intermittent claudication in a patient in need thereof, comprising administering to the patient an effective amount of a composition of claim 13.

21. A method of treating a disease or condition in a patient in need thereof, wherein the disease or condition is selected from insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability, comprising administering to the patient an effective amount of a composition of claim 13.

* * * * *

UNITED STATES PATENT AND TRADEMARK OFFICE
CERTIFICATE OF CORRECTION

PATENT NO. : 9,493,463 B2  
APPLICATION NO. : 14/713423  
DATED : November 15, 2016  
INVENTOR(S) : Roger D. Tung et al.

Page 1 of 1

It is certified that error appears in the above-identified patent and that said Letters Patent is hereby corrected as shown below:

In the Claims:

In Claim 10, at Column 79, please delete the following compounds:

| "400 | $CD_3$ | $CH_3$ | $CH_3$ | $(CH_2)_4$ | D | Taken together as =O |
| 401 | $CD_3$ | $CD_3$ | $CH_3$ | $(CH_2)_4$ | D | Taken together as =O |
| 402 | $CH_3$ | $CD_3$ | $CH_3$ | $(CH_2)_4$ | D | Taken together as =O" |

| "415 | $CD_3$ | $CD_3$ | $CH_3$ | $(CH_2)_4$ | D | OH | H |
| 416 | $CD_3$ | $CH_3$ | $CH_3$ | $(CH_2)_4$ | D | OH | H |
| 417 | $CH_3$ | $CD_3$ | $CH_3$ | $(CH_2)_4$ | D | OH | H" |

Signed and Sealed this  
Tenth Day of January, 2017

Michelle K. Lee  
*Director of the United States Patent and Trademark Office*